US008053603B2

(12) United States Patent
Shao et al.

(10) Patent No.: US 8,053,603 B2
(45) Date of Patent: Nov. 8, 2011

(54) TETRALONE-BASED MONOAMINE REUPTAKE INHIBITORS

(75) Inventors: Liming Shao, Lincoln, MA (US); Fengjiang Wang, Northborough, MA (US); Scott Christopher Malcolm, Southborough, MA (US); Michael Charles Hewitt, Somerville, MA (US); Larry R. Bush, Worcester, MA (US); Mark A. Varney, Laguna Niguel, CA (US); Una Campbell, Marlborough, MA (US); Sharon Rae Engel, Hudson, MA (US); Larry Wendell Hardy, Sturbridge, MA (US); Patrick Koch, Marlborough, MA (US); Jianguo Ma, Natick, MA (US)

(73) Assignee: Sunovion Pharmaceuticals Inc., Marlborough, MA (US)

( * ) Notice: Subject to any disclaimer, the term of this patent is extended or adjusted under 35 U.S.C. 154(b) by 995 days.

(21) Appl. No.: 11/643,190

(22) Filed: Dec. 21, 2006

(65) Prior Publication Data

US 2007/0197588 A1    Aug. 23, 2007

Related U.S. Application Data

(60) Provisional application No. 60/756,555, filed on Jan. 6, 2006.

(51) Int. Cl.
*C07C 211/42* (2006.01)
*A61K 31/133* (2006.01)
*A61K 31/135* (2006.01)

(52) U.S. Cl. ........ 564/308; 564/428; 564/454; 564/456; 560/28; 514/510; 514/647; 514/657

(58) Field of Classification Search .......... None
See application file for complete search history.

(56) References Cited

U.S. PATENT DOCUMENTS

| | | | |
|---|---|---|---|
| 3,663,608 A * | 5/1972 | Holava et al. ............ | 564/428 |
| 4,540,690 A | 9/1985 | Szmuszkovicz | |
| 4,587,258 A | 5/1986 | Gold et al. | |
| 4,738,709 A | 4/1988 | Nielsen | |
| 4,751,231 A | 6/1988 | Halczenko et al. | |
| 4,981,870 A | 1/1991 | Koe | |
| 5,091,429 A | 2/1992 | Begue et al. | |
| 5,225,596 A | 7/1993 | Carlsson et al. | |
| 5,373,018 A | 12/1994 | Cugola et al. | |
| 5,374,649 A | 12/1994 | Cugola et al. | |
| 5,523,278 A | 6/1996 | Wepplo | |
| 5,550,255 A | 8/1996 | Urbach et al. | |
| 5,578,627 A | 11/1996 | Takeda et al. | |
| 5,620,997 A | 4/1997 | Bolton et al. | |
| 5,668,162 A | 9/1997 | Domagala et al. | |
| 5,686,461 A | 11/1997 | Cugola et al. | |
| 5,859,042 A | 1/1999 | Lee et al. | |
| 5,962,496 A | 10/1999 | Cugola et al. | |
| 5,965,591 A | 10/1999 | Kojima et al. | |
| 6,096,771 A | 8/2000 | Kojima et al. | |
| 6,100,289 A | 8/2000 | Cugola et al. | |
| 6,331,636 B1 | 12/2001 | Romero et al. | |
| 6,372,919 B1 | 4/2002 | Lippa et al. | |
| 6,399,601 B1 | 6/2002 | Du Bois | |
| 6,479,527 B1 | 11/2002 | Barker et al. | |
| 6,576,653 B2 | 6/2003 | Du Bois | |
| 6,589,949 B1 | 7/2003 | Moriwaki et al. | |
| 6,603,000 B2 | 8/2003 | Yee et al. | |
| 6,828,460 B2 | 12/2004 | Browning et al. | |
| 6,995,144 B2 | 2/2006 | Ozaki et al. | |
| 7,166,725 B2 | 1/2007 | Fang et al. | |
| 7,226,938 B2 | 6/2007 | Cai et al. | |
| 7,488,747 B2 | 2/2009 | Fang et al. | |
| 7,579,370 B2 | 8/2009 | Heffernan et al. | |
| 7,615,572 B2 | 11/2009 | Fang et al. | |
| 2002/0010198 A1 | 1/2002 | Jerussi et al. | |
| 2002/0085976 A1 | 7/2002 | Elomari | |
| 2002/0123490 A1 | 9/2002 | Howard, Jr. | |
| 2002/0183369 A1 | 12/2002 | Du Bois | |
| 2003/0087803 A1 | 5/2003 | Yatvin et al. | |
| 2003/0171440 A1 | 9/2003 | Senanayake et al. | |
| 2003/0195361 A1 | 10/2003 | Du Bois | |
| 2003/0215523 A1 | 11/2003 | Ozawa et al. | |
| 2004/0048878 A1 | 3/2004 | Cai et al. | |
| 2004/0092605 A1 | 5/2004 | Jerussi et al. | |
| 2004/0106681 A1 | 6/2004 | Rao et al. | |
| 2004/0220229 A1 | 11/2004 | Bussolotti et al. | |
| 2005/0020645 A1 | 1/2005 | Ohta et al. | |
| 2005/0089935 A1 | 4/2005 | Cai et al. | |
| 2005/0143434 A1 | 6/2005 | Fang et al. | |

(Continued)

FOREIGN PATENT DOCUMENTS

BE    616646    5/1962

(Continued)

OTHER PUBLICATIONS

Database CAPLUS on STN, Acc. No. 1977:83511, KOE, Journal of Pharmacology and Experimental Therapeutics (1976), 199(3), p. 649-661 (abstract).*
Braga et al., Chem. Commun. (2005), 29, p. 3635-3645.*
Database CAPLUS on STN, Acc. No. 1993:233604, Bertolini et al., European Journal of Medicinal Chemistry (1992), 27(7), p. 663-672 (abstract).*
Database CAPLUS on STN, Acc. No. 1955:28047, Mikhailov et al., Sbornik Statei po Obshchei Khimii (1953), 2, p. 1085-1086 (abstract).*
Abarbri et al., "Les beta-cétonitriles groupes protecteurs de la fonction amine. Préparation d'amino-alcools", Helv. Chim. Acta 1995, 78(1), 109-121.

(Continued)

*Primary Examiner* — Brian J Davis

(57) ABSTRACT

The invention relates to novel tetralone based amines and their use in the treatment of central nervous system (CNS) disorders, such as depression, attention deficit hyperactivity disorder (ADHD) and Parkinson's disease. The invention further relates to pharmaceutical compositions containing the compounds and compositions of the invention as well as methods of inhibiting reuptake of one or more monoamine, such as such as dopamine and norepinephrine, from the synaptic cleft, and methods of modulating one or more monoamine transporter.

23 Claims, No Drawings

U.S. PATENT DOCUMENTS

| | | |
|---|---|---|
| 2005/0143443 A1 | 6/2005 | Fang et al. |
| 2006/0019944 A1 | 1/2006 | Wu et al. |
| 2006/0229286 A1 | 10/2006 | Kakigami et al. |
| 2006/0235002 A1 | 10/2006 | Nagai et al. |
| 2007/0100135 A1 | 5/2007 | Riggs et al. |
| 2007/0142452 A1 | 6/2007 | Banner et al. |
| 2007/0203111 A1 | 8/2007 | Shao et al. |
| 2008/0004327 A1 | 1/2008 | Heffernan et al. |
| 2008/0004328 A1 | 1/2008 | Dorsey et al. |
| 2008/0058395 A1 | 3/2008 | Heffernan et al. |
| 2009/0005456 A1 | 1/2009 | Shao et al. |
| 2009/0099248 A1 | 4/2009 | Heffernan et al. |
| 2009/0149549 A1 | 6/2009 | Zhao et al. |
| 2010/0016397 A1 | 1/2010 | Fang et al. |
| 2010/0022612 A1 | 1/2010 | Dorsey et al. |
| 2010/0029737 A1 | 2/2010 | Heffernan et al. |
| 2010/0029741 A1 | 2/2010 | Dorsey et al. |
| 2010/0120740 A1 | 5/2010 | Heffernan et al. |

FOREIGN PATENT DOCUMENTS

| | | |
|---|---|---|
| CA | 2033323 | 1/1991 |
| CA | 2066593 A1 | 2/1992 |
| CA | 2410077 A1 | 11/2001 |
| CA | 2474451 A1 | 8/2003 |
| CA | 2498152 A1 | 3/2004 |
| CA | 2498175 A1 | 3/2004 |
| CA | 2565852 A1 | 11/2005 |
| CA | 2566094 A1 | 12/2005 |
| CN | 1106386 A | 8/1995 |
| CN | 1709871 A | 12/2005 |
| CN | 1962656 A | 5/2007 |
| DE | 1124485 A | 3/1962 |
| DE | 3431541 A1 | 3/1986 |
| EP | 0101786 A1 | 3/1984 |
| EP | 0 399 982 | 11/1990 |
| EP | 0396124 A2 | 11/1990 |
| EP | 1136071 A2 | 9/2001 |
| EP | 1219603 A2 | 7/2002 |
| EP | 1262181 A1 | 12/2002 |
| EP | 1362864 A1 | 11/2003 |
| EP | 1088824 B1 | 1/2004 |
| EP | 1391460 A1 | 2/2004 |
| EP | 1420028 A2 | 5/2004 |
| ES | 2081747 A1 | 3/1996 |
| JP | S54-059269 A | 5/1979 |
| JP | H01-016786 A | 1/1989 |
| JP | H01-172388 A | 7/1989 |
| JP | H04-077476 A | 3/1992 |
| WO | WO 86/00896 A1 | 2/1986 |
| WO | WO 90/15047 | 12/1990 |
| WO | WO 92/06967 | 4/1992 |
| WO | WO 95/17381 A1 | 6/1995 |
| WO | WO 98/42709 A1 | 10/1998 |
| WO | WO 99/10343 A1 | 3/1999 |
| WO | WO 99/18065 A1 | 4/1999 |
| WO | WO 99/40913 A1 | 8/1999 |
| WO | WO 99/40914 A1 | 8/1999 |
| WO | WO 99/48868 A2 | 9/1999 |
| WO | WO 99/58490 | 11/1999 |
| WO | WO 00/07978 | 2/2000 |
| WO | WO 00/25770 A1 | 5/2000 |
| WO | WO 01/02427 A1 | 1/2001 |
| WO | WO 01/27103 A1 | 4/2001 |
| WO | WO 01/79208 A1 | 10/2001 |
| WO | WO 02/12249 A2 | 2/2002 |
| WO | WO 02/20530 A1 | 3/2002 |
| WO | WO 02/31128 A1 | 4/2002 |
| WO | WO 03/016302 A1 | 2/2003 |
| WO | WO 03/039540 A2 | 5/2003 |
| WO | WO 03/063797 A2 | 8/2003 |
| WO | WO 03/074531 A1 | 9/2003 |
| WO | WO 03/074532 A1 | 9/2003 |
| WO | WO 03/091213 A1 | 11/2003 |
| WO | WO 03/092670 A1 | 11/2003 |
| WO | WO 2004/022537 A2 | 3/2004 |
| WO | WO 2004/031193 A1 | 4/2004 |
| WO | WO 2004/031194 A1 | 4/2004 |
| WO | WO 2004/039787 A1 | 5/2004 |
| WO | WO 2004/041780 A2 | 5/2004 |
| WO | WO 2004/089470 A2 | 10/2004 |
| WO | WO 2004/113345 A1 | 12/2004 |
| WO | WO 2005/013981 A1 | 2/2005 |
| WO | WO 2005/018637 A1 | 3/2005 |
| WO | WO 2005/020986 A1 | 3/2005 |
| WO | WO 2005/020987 A1 | 3/2005 |
| WO | WO 2005/046575 A2 | 5/2005 |
| WO | WO 2005/066135 A2 | 7/2005 |
| WO | WO 2005/066143 A2 | 7/2005 |
| WO | WO 2005/089753 A2 | 9/2005 |
| WO | WO 2005/123677 A1 | 12/2005 |
| WO | WO 2006/001958 A2 | 1/2006 |
| WO | WO 2006/004040 A1 | 1/2006 |
| WO | WO 2006/021000 A2 | 2/2006 |
| WO | WO 2006/077412 A1 | 7/2006 |
| WO | WO 2007/039773 A1 | 4/2007 |
| WO | WO 2007/068621 A1 | 6/2007 |
| WO | WO 2007/081542 A2 | 7/2007 |
| WO | WO 2007/081857 A2 | 7/2007 |
| WO | WO 2007/115185 A2 | 10/2007 |
| WO | WO 2008/005456 A2 | 1/2008 |
| WO | WO 2008/089453 A2 | 7/2008 |
| WO | WO 2008/151156 A1 | 12/2008 |
| WO | WO 2009/020814 A2 | 2/2009 |
| WO | WO 2010/017418 A1 | 2/2010 |

OTHER PUBLICATIONS

Aboul-Enein et al., "Synthesis and Antiemetic Profile of N-[1-[(diethylamino)methyl]cyclohexyl]amides", Sci. Pharm. 1990, 58(3), 273-280.

Alvaro et al., "Preparation and photolysis of diaryl esters of acetylenedicarboxylic acid", Tetrahedron 1992, 48(16), 3437-3444.

Ando et al., "3-(Arylacetylamino)-N-methylbenzamides: A Novel Class of Selective Anti-Helicobacter pylori Agents", J. Med. Chem. 2001, 44(25), 4468-4474.

Arya et al., "Synthesis of New Heterocycles: Part XV. Synthesis of Novel Cyclic and Acyclic Sulfamides", Indian J. Chem., Sec. B, 1976, 14B(10), 766-769.

Ashton et al., "Nonpeptide angiotensin II antagonists derived from 1H-pyrazole-5-carboxylates and 4-aryl-1H-imidazole-5-carboxylates", J. Med. Chem. 1993, 36(23), 3595-3605.

Associated Press, "FDA mulls drug to slow late-stage Alzheimer's", CNN.com, Sep. 24, 2003, URL: <http://www.cnn.com/2003/HEALTH/conditions/09/24/alzheimers.drug.ap/index.html>.

Aubert et al., "New cyclopenta[b]-pyrroles and -pyridines by reaction of 2-azido- and 2-phosphoranylideneaminocyclopent-1-ene-1-carbaldehydes with aliphatic esters", J. Chem. Soc. Perkin Trans. 1 1989(8), 1369-1373.

Azéma et al., "Efficient approach to acyloxymethyl esters of nalidixic acid and in vitro evaluation as intra-ocular prodrugs", Bioorg. Med. Chem. 2006, 14(8), 2569-2580.

Baba et al., "Structure-Based Design of a Highly Selective Catalytic Site-Directed Inhibitor of Ser/Thr Protein Phosphatase 2B (Calcineurin)", J. Am. Chem. Soc. 2003, 125(32), 9740-9749.

Babu et al., "Simple and facile oxidation of aldehydes to carboxylic acids", Org. Prep. Proced. Int. 1994, 26(1), 123-125.

Bagal et al.,"Radicals from Aldehydes: A Convergent Access to Dienes and δ-Lactones", Synlett 2006(10), 1485-1490.

Balsamini et al., "(E)-3-(2-(N-phenylcarbamoyl)vinyl)pyrrole-2-carboxylic acid derivatives. A novel class of glycine site antagonists", J. Med. Chem. 1998, 41(6), 808-820.

Balsamini et al., "An improved route to cycloalka[b]pyrrole 2-carboxylates", Org. Prep. Proced. Int. 1997, 29(4), 471-473.

Bambury et al., "Trifluoromethylfurans II", J. Heterocycl. Chem. 1970, 7(2), 269-273.

Banekovich et al., "Synthesis and biological activities of novel dexibuprofen tetraacetylriboflavin conjugates", Bioorg. Med. Chem. Lett. 2007, 17(3), 683-687.

Banfi et al., "Synthesis of New Imidazole Derivatives as Potential Inhibitors of Thromboxane Synthetase", J. Heterocycl. Chem. 1990, 27, 215-219.

Bardakos et al., "Enhydrazine, 10. Einige aliphatische Enhydrazone", Chem. Ber. 1975, 108(7), 2161-2170.

Bartlett et al., "Evaluation of alternative approaches for the synthesis of macrocyclic bisindolylmaleimides", Org. Biomol. Chem. 2004, 2(19), 2874-2883.

BASF Corp., "Borane-tetrahydrofuran Complex (BTHF)" Product Bulletin, 2002, pp. 1-14.

Baumes et al., "No. 227.—Recherches sur les enehydrazines. VI.—Condensation de methylhydrazones de cetones sur les esters acetyleniques: synthese de carbomethoxypyrroles", Bull. Soc. Chim. Fr. 1974(5-6), 1147-1150.

Beaumont et al., "Design of Ester Prodrugs to Enhance Oral Absorption of Poorly Permeable Compounds: Challenges to the Discovery Scientist", Curr. Drug Metab. 2003, 4(6), 461-485.

Bedford et al., "Quaternary salts of 2-[(hydroxyimino)methyl]imidazole. 2. Preparation and in vitro and in vivo evaluaton of 1-(alkoxymethyl)-2-[(hydroxyimino)methyl]-3-methylimidazolium halides for reactivation of organophosphorus-inhibited acetylcholinesterases", J. Med. Chem. 1989, 32(2), 493-503.

Benson et al., "Aliphatic β-Chlorovinyl Aldoximes", J. Org. Chem. 1965, 30(4), 1126-1129.

Bergauer et al., "Practical ex-chiral-pool methodology for the synthesis of dopaminergic tetrahydroindoles", Tetrahedron 2004, 60(5), 1197-1204.

Bialer et al., "Pharmacokinetic analysis and antiepileptic activity of tetra-methylcyclopropane analogues of valpromide", Pharm. Res. 1996, 13(2), 284-289.

Biggadike et al., "Selective plasma hydrolysis of glucocorticoid gamma-lactones and cyclic carbonates by the enzyme paraoxonase: an ideal plasma inactivation mechanism." J. Med. Chem. 2000, 43(1), 19-21.

Birkofer et al., "The Use of Silylation in Organic Syntheses", Angew. Chem. Int. Ed. 1965, 4(5), 417-429.

Black, D., "Product Class 13: 1H-Pyrroles" in "Science of Synthesis: Houben-Weyl Methods of Molecular Transformations", vol. 9; Maas, G., ed.; Thieme Medical Publishers: Stuttgart, 2001; pp. 441-552.

Blanchfield et al., "The stability of lipidic analogues of GnRH in plasma and kidney preparations: the stereoselective release of the parent peptide", Bioorg. Med. Chem. Lett. 2005, 15(6), 1609-1612.

Bobbitt et al., "Organic Nitrosonium Salts. II. Stability Studies and Oxidations of Some Indole Derivatives", Heterocycles 1990, 30(2), 1131-1140.

Bobosik et al., "Synthesis of N-Phenylsulfonyl Protected Furo[3,2-b]pyrroles", Collect. Czech. Chem. Commun. 1994, 59(2), 499-502.

Boeshagen et al., "Ueber 3-Acylimino-3H-1.2-benzodithiole", Chem. Ber. 1968, 101(7), 2472-2484.

Borza et al., "Selective NR1/2B N-Methyl-d-aspartate Receptor Antagonists among Indole-2-carboxamides and Benzimidazole-2-carboxamides" J. Med. Chem. 2007, 50(5), 901-914.

Bregant et al., "Orthogonally Protected Lanthionines: Synthesis and Use for the Solid-Phase Synthesis of an Analogue of Nisin Ring C", J. Org. Chem. 2005, 70(7), 2430-2438.

Brunner et al., "Asymmetrische Hydrierung von (Z)-α-(Acetylamino)-zimtsäure mit einem Rh/norphos-Katalysator", Angew. Chem. 1979, 91(8), 655-656.

Brunner-Guenat et al., "Esters of L-dopa: structure-hydrolysis relationships and ability to induce circling behaviour in an experimental model of hemiparkinsonism", J. Pharm. Pharmacol. 1995, 47(10), 861-869.

Bueno et al., "Dipeptides as effective prodrugs of the unnatural amino acid (+)-2-aminobicyclo[3.1.0]hexane-2,6-dicarboxylic acid (LY354740), a selective group II metabotropic glutamate receptor agonist." J. Med. Chem. 2005, 48(16), 5305-5320.

Bundgaard et al., "Esters of N,N-disubstituted 2-hydroxyacetamides as a novel highly biolabile prodrug type for carboxylic acid agents", J. Med. Chem 1987, 30(3), 451-454.

Byrn et al., "Solid-State Chemistry of Drugs", 2nd ed.; SSCI, Inc.: West Lafayette, Indiana, 1999; pp. 232-247.

Cai et al., "Synthesis of 2,4,5-Trisubstituted Oxazoles", Synthesis 2005(10), 1569-1571.

Calderon et al., "Novel 1-Phenylcycloalkanecarboxylic Acid Derivatives Are Potent and Selective .sigma.1 Ligands", J. Med. Chem. 1994, 37(15), 2285-2291.

Callis et al., "A Tandem Horner—Emmons Olefination—Conjugate Addition Approach to the Synthesis of 1,5-Disubstituted-6-azabicyclo[3.2.1]octanes Based on the AE Ring Structure of the Norditerpenoid Alkaloid Methyllycaconitine", J. Org. Chem. 1996, 61(14), 4634-4640.

Cartoon et al., "Lithiation reactions of 1-(2'-bromophenyl)pyrrole and related compounds", J. Organomet. Chem. 1981, 212(1), 1-9.

Chakraborty et al., "Synthesis and characterization of Boc-protected 4-amino- and 5-amino-pyrrole-2-carboxylic acid methyl esters", Tetrahedron Lett. 2006, 47(27), 4631-4634.

Chapman et al., "The Analytical Reduction of Porphyrins to Pyrroles", Can. J. Chem. 1971, 49(21), 3544-3564.

Chaubey et al., "Kinetics of the Oxidation of Heterocyclic Aldehydes by Quinolinium Dichromate", Bull. Chem. Soc. Jpn. 2002, 75(10), 2215-2220.

Chen et al., "4,4-Difluoro-4-bora-3a,4a-diaza-s-indacene (BODIPY) Dyes Modified for Extended Conjugation and Restricted Bond Rotations", J. Org. Chem. 2000, 65(10), 2900-2906.

Chen et al., "Studies on the SAR and pharmacophore of milnacipran derivatives as monoamine transporter inhibitors", Bioorg. Med. Chem. Lett. 2008, 18(4), 1346-1349.

Chimichi et al., "New 5-(2-ethenylsubstituted)-3(2H)-furanones with in vitro antiproliferative activity", Tetrahedron 2003, 59(28), 5215-5223.

Cottineau et al., "Synthesis and hypoglycemic evaluation of substituted pyrazole-4-carboxylic acids", Bioorg. Med. Chem. Lett. 2002, 12(16), 2105-2108.

Crane et al., "A Novel Enantioselective Synthetic Route to Omuralide Analogues with the Potential for Species Selectivity in Proteasome Inhibition", Org. Lett. 2001, 3(9), 1395-1397.

Cuevas-Yañez et al., "Rhodium(II) catalyzed intramolecular insertion of carbenoids derived from 2-pyrrolyl and 3-indolyl α-diazo-β-ketoesters and α-diazoketones", Tetrahedron 2004, 60(7), 1505-1511.

Cyranski et al., "Aromaticity of dihetero analogues of pentalene dianion. X-Ray and ab initio studies of eight methyl furo[3,2-b]pyrrole-5-carboxylate derivatives and five methyl furo[2,3-b]pyrrole-5-carboxylate derivatives", Tetrahedon 2001, 57(42), 8867-8873.

Damaslo, A. R., "Alzheimer's Disease and Related Dementias" in "Cecil Textbook of Medicine", 20th ed., vol. 2; W.B. Saunders Co.: Philadelphia, 1996; pp. 1992-1996.

Dandarova et al., "13C NMR spectra of some substituted furo[3,2-b] pyrroles", Magn. Reson. Chem. 1990, 28(9), 830-831.

Das et al., "Synthesis of some N-substituted carbazoles and their larvicidal studies", J. Indian Chem. Soc. 2005, 82, 158-160.

Database Beilstein, Beilstein Institute for Organic Chemistry, Frankfurt-Main, DE; Database Accession No. BRN: 10196160 Abstract; and Eur. J. Org. Chem. 2005(21), 4670-4679.

Database Beilstein, Beilstein Institute for Organic Chemistry, Frankfurt-Main, DE; Database Accession No. BRN: 1074598 Abstract; and Can. J. Chem. 1978, 56(10), 1429-1434.

Database Beilstein, Beilstein Institute for Organic Chemistry, Frankfurt-Main, DE; Database Accession No. BRN: 4185621 Abstract; and Collect. Czech. Chem. Commun. 1986, 51(1), 106-111.

Database Beilstein, Beilstein Institute for Organic Chemistry, Frankfurt-Main, DE; Database Accession No. BRN: 4429388 Abstract; and Collect. Czech. Chem. Commun. 1984, 49(1), 65-70.

Database Beilstein, Beilstein Institute for Organic Chemistry, Frankfurt-Main, DE; Database Accession No. BRN: 7812555 Abstract; and Collect. Czech. Chem. Commun. 1997, 62(10), 1612-1622.

De Luca et al., "A New, Simple Procedure for the Synthesis of Formyl Amides", Synlett 2004(14), 2570-2572.

Denmark et al., "Chiral fluoro ketones for catalytic asymmetric epoxidation of alkenes with oxone", J. Org. Chem. 2002, 67(10), 3479-3486.

Denmark et al., "Organocerium additions to SAMP-hydrazones: general synthesis of chiral amines", J. Am. Chem. Soc. 1987, 109(7), 2224-2225.

Dhanak et al., "Studies in the protection of pyrrole and indole derivatives", J. Chem. Soc., Perkin Trans. 1, 1986, 2181-2186.

Durrer et al., "Structure-metabolism relationships in the hydrolysis of nicotinate esters by rat liver and brain subcellular fractions", Pharm. Res. 1991, 8(7), 832-839.

Elghamry, "Synthesis of ethyl pyrrole-2-carboxylates: a regioselective cyclization of enaminones under knorr-type conditions", Synth. Commun. 2002, 32(6), 897-902.

Eliel, "Infelicitous stereochemical nomenclature", Chirality 1997, 9(5-6), 428-430.

El-Nagger et al., "Synthesis and Biological Activity of Some New Aminoacylcarbazole Derivatives. Part I", J. Heterocycl. Chem. 1982, 19, 1025-1028.

English et al., "Orally effective acid prodrugs of the beta-lactamase inhibitor sulbactam", J. Med. Chem. 1990, 33(1), 344-347.

Eras et al., "Reactivity of thienopyrroles. Synthesis of isomeric nitro and bromothienopyrroles", J. Heterocycl. Chem. 1984, 21(1), 215-217.

Estep, "An Efficient Synthesis of 4-Hydroxy-1H-indole-2-carbonitrile and Its Conversion to DPI 201-106", Synth. Commun. 1995, 25(4), 507-514.

Fagan et al., "A new approach to the core of roseophilin", Tetrahedron Lett. 1999, 40(33), 6117-6120.

Ferguson et al., "N-Acetyl-5,6-dihydrofuro[3,2-b]pyrid-2-one, C9H9NO3", Cryst. Struct. Comm. 1976, 5, 911-914.

Fischer et al., "On Benzisothiazolones: A Series with a Wide Range of Bacteriostatic and Fungistatic Activity", Arzneimittel-Forschung 1964, 14(12), 1301-1306.

Fischer et al., "Synthese einiger Pyrrole und ihre Umsetzungen", Justus Liebigs Ann. Chem. 1932, 492(1), 128-155.

Fischer et al., "Synthesen der Opso- und Hämopyrrolcarbonsäure. Neue Synthese von Koproporphyrin. II", Justus Liebigs Ann. Chem. 1928, 462(1), 240-250.

Fischer et al., "Synthesen von Koproporphyrin I und II, sowie Mesoporphyrin II, V und XII", Justus Liebigs Ann. Chem. 1928, 466(1), 147-178.

Fisera et al., "Correlation of Kinetic Data of 1,3-Dipolar Cycloadditions of C-Benzoyl-N-phenylnitrones with the Homo Energies of Furan Derivatives", Collect. Czech. Chem. Commun. 1981, 46, 1504-1512.

Fisera et al., "Cycloadditions of C-Benzoyl-N-phenylnitrone with Furocondensed Derivatives", Collect. Czech. Chem. Commun. 1981, 46, 2421-2427.

Flaugh et al., "Synthesis of porphyrins. Deoxophylloerythroetioporphyrin", J. Am. Chem. Soc. 1968, 90(24), 6877-6879.

Foucaud et al., "The [1+4] cycloaddition of isocyanides with 1-aryl-2-nitro-1-propenes. Methyl 2-nitro-3-arylpropenoates and methyl 2-nitro-2,4-pentadienoates. Synthesis of 1-hydroxyindoles and 1-hydroxypyrroles", J. Org. Chem. 1983, 48(21), 3639-3644.

Fraga-Dubreuil et al., "Grafted ionic liquid-phase-supported synthesis of small organic molecules", Tetrahedron Lett. 2001, 42(35), 6097-6100.

Franciò et al., "Asymmetric Catalysis with Chiral Phosphane/Phosphoramidite Ligands Derived from Quinoline (QUINAPHOS)", Angew. Chem. Int. Ed. 2000, 39(8), 1428-1430.

Frisell et al., "Flavoenzyme Catalysis. Substrate-Competitive Inhibition of D-Amino Acid Oxidase", J. Biol. Chem. 1956, 223, 75-83.

Fu et al., "Design and synthesis of novel bis(I-amino acid) ester prodrugs of 9-[2-(phosphonomethoxy)ethyl]adenine (PMEA) with improved anti-HBV activity", Bioorg. Med. Chem. Lett. 2007, 17(2), 465-470.

Fukuda et al., "Tensidols, New Potentiators of Antifungal Miconazole Activity, Produced by *Aspergillus niger* FKI-2342", J. Antibiot. 2006, 59(8), 480-485.

Gabbutt et al., "A Facile Synthesis of Some Benzothiopyrano[4,3-b]pyrroles", J. Chem. Res. (S) 1997(3), 102-103.

Gale et al., "Preparation and Reactions of 5-Carbethoxythieno[3,2-b]pyrrole and Some of Its Derivatives", J. Org. Chem. 1964, 29(8), 2160-2165.

Garg et al., "Development of an Enantiodivergent Strategy for the Total Synthesis of (+)- and (−)-Dragmacidin F from a Single Enantiomer of Quinic Acid", J. Am. Chem. Soc. 2005, 127(16), 5970-5978.

Gelas-Mialhe et al., "Photochemical heterocyclization of functionalized dienamines", J. Org. Chem. 1987, 52(24), 5395-5400.

Gelas-Mialhe et al., "Réactivité des N-vinylaziridines fonctionnalisées. Synthèse de dérivés des α,βdéhydro α-amino acides", Can. J. Chem. 1982, 60(22), 2830-2851.

Geraldine et al., "How an increase in the carbon chain length of the ester moiety affects the stability of a homologous series of oxprenolol esters in the presence of biological enzymes", J. Pharm. Sci. 1998, 87(7), 880-885.

Gross et al., "Direct observation of 1-azafulven-6-one and annelated derivatives", J. Chem. Soc., Chem. Commun. 1982(6), 360-361.

Grygorenko et al., "Stereoselective synthesis of 2,4-methanoproline homologues", Tetrahedron Asymmetry 2006, 17(2), 252-258.

Guan et al., "Design and synthesis of aminopropyl tetrahydroindole-based indolin-2-ones as selective and potent inhibitors of Src and Yes tyrosine kinase", Bioorg. Med. Chem. Lett. 2004, 14(1), 187-190.

Haginoya et al., "Synthesis and conformational analysis of a non-amidine factor Xa inhibitor that incorporates 5-methyl-4,5,6,7-tetrahydrothiazolo[5,4-c]pyridine as S4 binding element", J. Med. Chem. 2004, 47(21), 5167-5182.

Haj-Yehia et al., "Pharmacokinetic analysis of the structural requirements for forming "stable" analogues of valpromide", Pharm. Res. 1992, 9(8), 1058-1063.

Haj-Yehia et al., "Structure-pharmacokinetic relationships in a series of valpromide derivatives with antiepileptic activity", Pharm. Res. 1989, 6(8), 683-689.

Harada et al., "A Simple Preparation of Chloromethyl Esters of the Blocked Amino Acids", Synth. Commun. 1994, 24(6), 767-772.

Harrak et al.,"PtCI2-Catalyzed Cycloisomerizations of 5-En-1-yn-3-ol Systems", J. Am. Chem. Soc. 2004, 126(28), 8656-8657.

Harrison et al., "Cyclopenta[b]indoles. Part 2. Model studies towards the tremorgenic mycotoxins", J. Chem. Soc. Perkin Trans. 1 1995(9), 1131-1136.

Harwood et al., "Tandem generation and intramolecular trapping of chiral stabilised azomethine ylids with alkyne dipolarophiles", Tetrahedron Lett. 1993, 34(41), 6603-6606.

Hauptmann et al., "Beiträge zum Reaktionsverhalten von 2-Aminovinylcarbonylverbindungen", Journal für Praktische Chemie 1972, 314(2), 353-364.

Hauptmann et al., "Eine neue Synthese substituierter Thiophene und Pyrrole", Tetrahedron Lett. 1968, 9(11), 1317-1319.

Hemetsberger et al., "Synthese und Thermolyse von α-Azidoacrylestern", Monatsh. Chem. 1972, 103(1), 194-204.

Hillenweck et al., "Chlorothalonil Biotransformation by Gastrointestinal Microflora: In Vitro Comparative Approach in Rat, Dog, and Human", Pestic. Biochem. Physiol. 1997, 58(1), 34-48.

Hilton et al., "Observations on the reactivity of thiyl radicals derived from 3,6-epidithiodiketopiperazine-2,5-diones and related congeners", Bioorg. Med. Chem. Lett. 2005, 15(9), 2239-2242.

Hoffman, R. V., "Organic Chemistry: An Intermediate Text, Second Edition"; Wiley: Hoboken, 2004; pp. 124 and 138-144.

Holmes et al., "Reactions of N-Benzylthieno[3,2-b]pyrrole. I. Metalation and an Electrophilic Substitution", J. Org. Chem. 1964, 29(8), 2155-2160.

Hori, M., "Syntheses of Analgesics. XIV. Aminocyclohexane Derivatives. 8.", Yakugaku Zasshi 1958, 78, 11-14.

Howarth et al., "Pyrroles and related compounds. Part XXVI. Pyrrole beta-keto-esters", J. Chem. Soc. Perkin Trans. 1 1974, 490-501.

Hu et al., "Synthesis of a Porphyrin with Fused Five- and Seven-membered Exocyclic Rings from a Cross-conjugated Tetracyclic Dipyrrole", Synlett 1994(11), 909-910.

Ikegami et al., "Synthesis and pharmacological activity of O-(5-isoxazolyl)-L-serine", Chem. Pharm. Bull. 2000, 48(2), 278-280.

Ilyin et al., "Synthesis of Annelated Azaheterocycles Containing a 5-Carbamoylpyrazin-3-one Fragment by a Modification of the Four-Component Ugi Reaction", Eur. J. Org. Chem. 2005(21), 4670-4679.

Ingram et al., "Investigation of enzyme activity by SERRS using poly-functionalised benzotriazole derivatives as enzyme substrates", Org. Biomol. Chem. 2006, 4(15), 2869-2873.

Inukai et al., "ortho-Disubstituted F-Benzenes. III. Preparation of (F-Benzo)heterocyclic Compounds from F-Benzoic Acid and F-Phenol, and the Reactions of Some Intermediary F-Benzoyl- and F-Phenoxy Compounds", Bull. Chem. Soc. Jpn. 1981, 54(11), 3447-3452.

Iranpoor et al., "A Rapid and Facile Conversion of Primary Amides and Aldoximes to Nitriles and Ketoximes to Amides with Triphenylphosphine and N-Chlorosuccinimide", Synth. Commun. 2002, 32(16), 2535-2541.

Isoherranen et al., "New CNS-active drugs which are second-generation valproic acid: can they lead to the development of a magic bullet?", Curr. Opin. Neurol. 2003, 16(2), 203-211.

Jacob et al., "Gamma-Aminobutyric acid esters. 2. Synthesis, brain uptake, and pharmacological properties of lipid esters of gamma-aminobutyric acid", J. Med. Chem. 1985, 28(1), 106-110.

Java et al., "Chimie Organique.—Synthese de selenolo, furo et pyrrolopyrroles", C. R. Acad. Sc. Paris 1975, 281 Serie C (19), 793-795.

Jolicoeur et al., "Pyrrole protection", Tetrahedron 2006, 62(50), 11531-11563.

Katritzky et al., "Efficient Conversion of Carboxylic Acids into N-Acylbenzotriazoles", Synthesis 2003(18), 2795-2798.

Katritzky et al., "Novel Synthesis of Bicycles with Fused Pyrrole, Indole, Oxazole, and Imidazole Rings", J. Org. Chem. 2004, 69(26), 9313-9315.

Katritzky et al., "Regiospecific C-Acylation of Pyrroles and Indoles Using N-Acylbenzotriazoles", J. Org. Chem. 2003, 68(14), 5720-5723.

Katterle et al., "A Heck-Type Coupling for the Synthesis of Novel Bridged Metallochlorin-Fullerene C60 Dyads", European J. Org. Chem. 2006(2), 414-422.

Keener et al., "Synthesis of 6-substituted thieno[3,2-b]pyrroles", J. Org. Chem. 1968, 33(4), 1355-1359.

Kesel, "Synthesis of Novel Test Compounds for Antiviral Chemotherapy of Severe Acute Respiratory Syndrome (SARS)", Curr. Med. Chem. 2005, 12(18), 2095-2162.

Khanna et al., "Evaluation of glycolamide esters of indomethacin as potential cyclooxygenase-2 (COX-2) inhibitors", Bioorg. Med. Chem. 2006, 14(14), 4820-4833.

Kittredge et al., "Alpha-Helical Polypeptide Films Grown From Sulfide or Thiol Linkers on Gold Surfaces", Helv. Chim. Acta 2002, 85(3), 788-798.

Kleinspehn et al., "The Synthesis of Some β,β-Dipyrrylpropionic Esters", J. Am. Chem. Soc. 1954, 76(22), 5641-5646.

Kralovicova et al., "Electrophilic Substitution Reactions of Furo[3,2-b]pyrrole Derivatives", Collect. Czech. Chem. Commun. 1986, 51(1), 106-111.

Krayushkin et al., "Synthesis of Photochromic 1,2-Dihetarylethene Using Regioselective Acylation of Thienopyrroles", Org. Lett. 2002, 4(22), 3879-3881.

Kren et al., "Clustered ergot alkaloids modulate cell-mediated cytotoxicity", Bioorg. Med. Chem. 2002, 10(2), 415-424.

Krutosikova et al., "Addition and Cycloaddition Reactions of Furo[3,2-b]pyrroles and Their Benzo[b] Analogues: An NMR Study of Structure of Products", Collect. Czech. Chem. Commun. 1988, 53(5), 1770-1778.

Krutosikova et al., "Effect of microwave irradiation on reaction of furo[3,2-b]pyrrole and furo[2,3-b]pyrrole-2-carbaldehydes with some active methylene compounds", ARKIVOC 2000(iii), 409-420.

Krutosikova et al., "Reactions of Ethyl 2-(4-chlorophenyl)-4H-furo[3,2-b]pyrrole-5-carboxylate", Collect. Czech. Chem. Commun. 1980, 45(III), 2949-2957.

Krutosikova et al., "Reactions of furo[3,2-b]pyrroles and their benzo[b] analogues", Chem. Papers 1988, 42(1), 89-95.

Krutosikova et al., "Reactions of Methyl 2-Formylfuro[3,2-b]pyrrole-5-carboxylates", Chem. Papers 1996, 50(2), 72-76.

Krutosikova et al., "Substituted 4-Benzylfuro[3,2-b]pyrroles", Collect. Czech. Chem. Commun. 1992, 57(5), 1487-1494.

Krutosikova et al., "Substituted Vinyl Azides in the Synthesis of Condensed Nitrogen Heterocycles", Chem. Papers 1994, 48(4), 268-273.

Krutosikova et al., "Synthesis and Reactions of 4-Oxiranylmethylfuro[3,2-b]pyrroles and Their Benzo Derivatives", Chemistry of Heterocyclic Compounds 2001, 37(12), 1511-1517.

Krutosikova et al., "Synthesis and Reactions of 8-Hydrazinofuro[2',3':4,5]pyrrolo-[1,2-d][1,2,4]triazines", Collect. Czech. Chem. Commun. 1997, 62(10), 1612-1622.

Krutosikova et al., "Synthesis and Reactions of Furo[2,3-b]pyrroles", Molecules 1997, 2(4), 69-79.

Krutosikova et al., "Synthesis and Reactions of Furocondensed Derivatives", Collect. Czech. Chem. Commun. 1984, 49(1), 65-70.

Krutosikova et al., "Synthesis and Reactions of Substituted Furo[3,2-b]pyrrole Derivatives", Collect. Czech. Chem. Commun. 1981, 46, 2564-2572.

Kukolja et al., "Orally absorbable cephalosporin antibiotics. 2. Structure-activity studies of bicyclic glycine derivatives of 7-aminodeacetoxycephalosporanic acid", J. Med. Chem. 1985, 28(12), 1896-1903.

Kumar et al., "Synthesis and biological evaluation of thiophene [3,2-b] pyrrole derivatives as potential anti-inflammatory agents", Bioorg. Med. Chem. 2004, 12(5), 1221-1230.

Kuo et al., "G-protein coupled receptors: SAR analyses of neurotransmitters and antagonists", J. Clin. Pharm. Ther. 2004, 29(3), 279-298.

Lamboley et al., "Synthesis and Properties of Conformationally Constrained Analogues of Floral-Type Odorants", Helv. Chim. Acta 2004, 87(7), 1767-1793.

Lash et al., "Influence of carbocyclic rings on porphyrin cyclizations: synthesis of geochemically significant cycloalkanoporphyrins", Energy Fuels 1990, 4(6), 668-674.

Lash et al., "Normal and Abnormal Heme Biosynthesis. 2.1 Synthesis and Metabolism of Type-III Pentacarboxylic Porphyrinogens: Further Experimental Evidence for the Enzymic Clockwise Decarboxylation of Uroporphyrinogen-III", J. Org. Chem. 1999, 64(2), 478-487.

Lash et al., "Porphyrins with exocyclic rings. 1. Chemistry of 4,5,6,7-tetrahydro-1H-indoles: synthesis of acetoxy derivatives, dihydroindoles, and novel porphyrins with four exocyclic rings", J. Org. Chem. 1992, 57(18), 4809-4820.

Lash et al., "Porphyrins with exocyclic rings. Part 3. A reassessment on the utility of cyclopenta[b]pyrroles in the synthesis of porphyrin molecular fossils. Preparation of three type II porphyrins related to deoxophylloerythroetioporphyrin (DPEP)", Tetrahedron 1993, 49(20), 4159-4172.

Lash et al., "Recent advances in the synthesis of porphyrins with five-membered exocyclic rings", Energy Fuels 1993, 7(2), 172-178.

Law et al., "The synthesis and chemistry of azolenines. Part 2. A general synthesis of pyrrole-2-carboxylic acid derivatives by the reaction of 2H-azirines with enamines, and the crystal and molecular structure of ethyl 3-phenyl-4,5,6,7-tetrahydroindole-2-carboxylate", J. Chem. Soc. Perkin Trans. 1 1984, 111-118.

Layzer, R. B., "Section Five—Degenerative Diseases of the Nervous System" in "Cecil Textbook of Medicine", 20th ed., vol. 2; W.B. Saunders Co.: Philadelphia, 1996; pp. 2050-2057.

Lee at al., "Amphiphilic amino acid copolymers as stabilizers for the preparation of nanocrystal dispersion", Eur. J. Pharm. Sci. 2005, 24(5), 441-449.

Lee et al., "An Effective and Convenient Esterification of Cephalosporin Derivatives by Using Quarternary Ammonium Salts as Catalysts", Synth. Commun. 1998, 28(23), 4345-4354.

Lerche et al., "Umsetzungen mit Monohydrazonen von Dicarbonylverbindungen, V: Umsetzungen von Hydrazonoethylidenammonium-Salzen und Hydrazonoaldehyden mit Grignard-Verbindungen", Chem. Ber. 1978, 111(3), 1195-1209.

Li et al., "Synthesis of deoxophylloerythroetioporphyrin (DPEP) and three ring homologs by an improved b-bilene methodology", Tetrahedron Lett. 1998, 39(47), 8571-8574.

Liederer et al., "Enzymes involved in the bioconversion of ester-based prodrugs", J. Pharm. Sci. 2006, 95(6), 1177-1195.

Liederer et al., "Stability of oxymethyl-modified coumarinic acid cyclic prodrugs of diastereomeric opioid peptides in biological media from various animal species including human", J. Pharm. Sci. 2005, 94(10), 2198-2206.

Liu et al., "Facile construction of the pentacyclic framework of subincanadine B. Synthesis of 20-deethylenylated subincanadine B and 19,20-dihydrosubincanadine B", Org. Lett. 2006, 8(1), 115-118.

Liu et al., "Indole-5-phenylcarbamate derivatives as human non-pancreatic secretory phospholipase A2 inhibitor", Bioorg. Med. Chem. Lett. 2005, 15(20), 4540-4542.

Liu et al., "The synthesis of camostat intermediate", Huaxue Shiji, 2006, 28(6), 371-372.

Ma et al., "Hydrolysis of angiotensin II receptor blocker prodrug olmesartan medoxomil by human serum albumin and identification of its catalytic active sites", Drug Metab. Dispos. 2005, 33(12), 1911-1919.

Majumdar et al., "α-(1H-Imidazol-1-yl)alkyl (IMIDA) carboxylic acid esters as prodrugs of carboxylic acid containing drugs", Tetrahedron Lett. 2007, 48(26), 4609-4611.

Mal et al., "Regioselective synthesis of 1-hydroxycarbazoles via anionic [4+2] cycloaddition of furoindolones: a short synthesis of murrayafoline-A", Tetrahedron Lett. 2006, 47(7), 1071-1075.

Mamber et al., "Tubulin polymerization by paclitaxel (taxol) phosphate prodrugs after metabolic activation with alkaline phosphatase", J. Pharmacol. Exp. Ther. 1995, 274(2), 877-883.

Mandel et al., "Neuroprotective Strategies in Parkinson's Disease: An Update on Progress", CNS Drugs 2003, 17(10), 729-762.

Marrel et al., "L-Dopa esters as potential prodrugs 1. Physicochemical properties", Eur. J. Med. Chem. 1985, 20(5), 459-465.

Marrel et al., "L-Dopa esters as potential prodrugs 2. Chemical and enzymatic-hydrolysis", Eur. J. Med. Chem. 1985, 20(5), 467-470.

Martin et al., "Das Diazo-chinon von PQQ als mögliches Reagenz für die Kartierung von Chinoproteinen mittels Photoaffinitätsmarkierung", Helv. Chim. Acta 1993, 76(4), 1674-1677.

Martin et al., "Do structurally similar molecules have similar biological activity?", J. Med. Chem. 2002, 45(19), 4350-4358.

McConnaughie et al., "Novel Acridine-Triazenes as Prototype Combilexins: Synthesis, DNA Binding, and Biological Activity" J. Med. Chem. 1995, 38(18), 3488-3501.

McLaughlin, "Suzuki-Miyaura Cross-Coupling of Benzylic Phosphates with Arylboronic Acids", Org. Lett. 2005, 7(22), 4875-4878.

Medforth et al., "Nonplanar distortion modes for highly substituted porphyrins", J. Am. Chem. Soc. 1992, 114(25), 9859-9869.

Meltzer et al., "The synthesis of bivalent 2β-carbomethoxy-3β-(3,4-dichlorophenyl)-8-heterobicyclo[3.2.1]octanes as probes for proximal binding sites on the dopamine and serotonin transporters", Bioorg. Med. Chem. 2008, 16(4), 1832-1841.

Mergen et al., "Antiepileptic activity of 1,3-dihexadecanoylamino-2-valproyl-propan-2-ol, a prodrug of valproic acid endowed with a tropism for the central nervous system", J. Pharm. Pharmacol. 1991, 43(11), 815-816.

Merisor et al., "Synthesis of New Derivatives in the Izoxazole Class with Potential Antimicrobial Activity", Rev. Chim. (Bucharest, Romania) 2001, 52(4), 206-209.

Miao et al., "Benzamide derivatives as blockers of Kv1.3 ion channel", Bioorg. Med. Chem. Lett. 2003, 13(6), 1161-1164.

Mikhaleva et al., "Expedient synthesis of 1-vinylpyrrole-2-carbaldehydes", Tetrahedron Lett. 2006, 47(22), 3693-3696.

Miki et al., "Synthesis of 3-Methoxyellipticine and Ellipticine by Friedel-Crafts Reaction of Indole-2,3-dicarboxylic Anhydride and Selective Demethylation", Heterocycles 2005, 65(11), 2693-2703.

Milkiewicz et al., "Synthesis of a novel series of tetra-substituted furan[3,2-b]pyrroles", Tetrahedron Lett. 2003, 44(22), 4257-4260.

Mishra et al., "Synthesis, characterization and pharmacological evaluation of amide prodrugs of ketorolac", Eur. J. Med. Chem. 2008, 43(11), 2464-2472.

Mokhallalati et al., "A single-pot synthesis of 1,1,2-trisubstituted 1,2-dihydronaphthalenes in high enantiomeric purity",Tetrahedron Lett. 1994, 35(25), 4267-4270.

Montero et al., "Solid-Phase Combinatorial Synthesis of Peptide-Biphenyl Hybrids as Calpain Inhibitors", Org. Lett. 2004, 6(22), 4089-4092.

Morgan et al., "Synthesis of hydrocarbon-strapped porphyrins containing quinone and phenolic groups", J. Org. Chem. 1987, 52(24), 5364-5374.

Morissette et al., "High-throughput crystallization: polymorphs, salts, co-crystals and solvates of pharmaceutical solids", Adv. Drug Deliv. Rev. 2004, 56(3), 275-300.

Mork et al., "Stereoselective enzymatic hydrolysis of various ester prodrugs of ibuprofen and flurbiprofen in human plasma", Pharm. Res. 1992, 9(4), 492-496.

Muchowski et al., "Protecting groups for the pyrrole and indole nitrogen atom. The [2-(trimethylsilyl)ethoxy]methyl moiety. Lithiation of 1-[[2-(trimethylsilyl)ethoxy]methyl]pyrrole", J. Org. Chem. 1984, 49(1), 203-205.

Murakami et al., "The Friedel-Crafts Acylation of Ethyl Pyrrole-2-carboxylate. Scope, Limitations, and Application to Synthesis of 7-Substituted Indoles", Heterocycles 1988, 27(8), 1855-1860.

Nacci et al., "Polycondensed Heterocycles. I. Synthesis of 11-Oxo-5H,11H-pyrrolo[2,1-c][1,4]benzothiazepine, Derivative of a Novel Ring System", J. Heterocycl. Chem. 1985, 22(2), 259-263.

Nacci et al., "Polycondensed Heterocycles. II. A New Preparative Route to 11-Oxo-5H,11H-pyrrolo[2,1-c][1,4]benzothiazepine", J. Heterocycl. Chem. 1986, 23(3), 769-773.

Nagarathnam et al., "Design and Synthesis of Novel α1a Adrenoceptor-Selective Dihydropyridine Antagonists for the Treatment of Benign Prostatic Hyperplasia", J. Med. Chem. 1998, 41(26), 5320-5333.

Nagel et al., "Enantioselektive Katalyse, 4. Synthese N-substituierter (R,R)-3,4-Bis(diphenylphosphino)-pyrrolidine und Anwendung ihrer Rhodiumkomplexe zur asymmetrischen Hydrierung von α-(Acylamino)acrylsäure-Derivaten", Chem. Ber. 1986, 119(11), 3326-3343.

Narasimhan et al., "A QSAR approach for the prediction of stability of benzoglycolamide ester prodrugs", Chem. Pharm. Bull. 2006, 54(8), 1067-1071.

Nelson et al., "Stereoselective Synthesis of a Potent Thrombin Inhibitor by a Novel P2-P3 Lactone Ring Opening", J. Org. Chem. 2004, 69(11), 3620-3627.

New et al., "The thieno[3,2-c]pyridine and furo[3,2-c]pyridine rings: new pharmacophores with potential antipsychotic activity", J. Med. Chem. 1989, 32(6), 1147-1156.

Newman-Evans et al., "The influence of intramolecular dynamics on branching ratios in thermal rearrangements", J. Org. Chem. 1990, 55(2), 695-711.

Nielsen et al., "Bioreversible quaternary N-acyloxymethyl derivatives of the tertiary amines bupivacaine and lidocaine—synthesis, aqueous solubility and stability in buffer, human plasma and simulated intestinal fluid", Eur. J. Pharm. Sci. 2005, 24(5), 433-440.

Nielsen et al., "Glycolamide esters as biolabile prodrugs of carboxylic acid agents: Synthesis, stability, bioconversion, and physicochemical properties", J. Pharm. Sci. 1988, 77(4), 285-298.

Nudelman et al., "Novel anticancer prodrugs of butyric acid. 2.", J. Med. Chem. 1992, 35(4), 687-694.

Nudelman et al., "The role of intracellularly released formaldehyde and butyric acid in the anticancer activity of acyloxyalkyl esters." J. Med. Chem. 2005, 48(4), 1042-1054.

Ogawa et al., "Preparation of oxygen-bridged aza[15]- and aza[17]annulene dicarboxylates by intramolecular azide cyclization", Tetrahedron Lett. 1988, 29(2), 219-222.

Ojida et al., "Highly Enantioselective Reformatsky Reaction of Ketones: Chelation-Assisted Enantioface Discrimination", Org. Lett. 2002, 4(18), 3051-3054.

Ouyang et al., "Steric hindrance is a key factor in the coupling reaction of (acyloxy) alkyl-α-halides with phenols to make a new promoiety for prodrugs", Tetrahedron Lett. 2002, 43(4), 577-579.

Paine et al., "Regioselectivity of pyrrole synthesis from diethyl aminomalonate and 1,3-diketones: further observations", J. Org. Chem. 1987, 52(18), 3986-3993.

Parikh et al., "The Use of Amino Acid Oxidases for the Small-scale Preparation of the Optical Isomers of Amino Acids", J. Am. Chem. Soc. 1958, 80(4), 953-958.

Paxéus et al., "Screening for non-regulated organic compounds in municipal wastewater in Göteborg, Sweden", Water Sci. Technol. 1996, 33(6), 9-15.

Pérez-Balderas et al., "Synthesis of multivalent neoglycoconjugates by 1,3 dipolar cycloaddition of nitrile oxides and alkynes and evaluation of their lectin-binding affinities", Tetrahedron 2005, 61(39), 9338-9348.

Pfeiffer et al., "Synthesen und Eigenschaften von Pyrrolindigo-Verbindungen", Liebigs Ann. Chem. 1980(4), 564-589.

Poszavacz et al., "New Synthesis of Naratriptan", Heterocycles 2006, 68(4), 713-719.

Puterova et al., "Reaction of Substituted Furan-2-carboxaldehydes and Furo[b]pyrrole Type Aldehydes with Hippuric Acid", Molecules 2004, 9(1), 11-21.

Puterova et al., "Reactions of Substituted Furan-2-carboxaldehydes and Furo[b]pyrrole Type Aldehydes with Benzothiazolium Salts", Molecules 2004, 9(4), 241-255.

Quizon-Colquitt et al., "Porphyrins with exocyclic rings. Part 4. An improved one step synthesis of cyclopenta[b]pyrroles", J. Heterocycl. Chem. 1993, 30(2), 477-482.

Rautio et al., "Synthesis and in Vitro Evaluation of Novel Morpholinyl- and Methylpiperazinylacyloxyalkyl Prodrugs of 2-(6-Methoxy-2-naphthyl)propionic Acid (Naproxen) for Topical Drug Delivery", J. Med. Chem. 2000, 43(8), 1489-1494.

Rodriguez et al., "Conformational and molecular study of the 4-(2-carboxyethyl)-1,2,3,4-tetrahydrocyclopent[b]indole", Tetrahedron 1985, 41(18), 3813-3823.

Romanova et al., "DC Polarographic and UV Spectrometric Studies of Substituted Furo[3,2-b]- and Furo[2,3-b]pyrroles", Collect. Czech. Chem. Commun. 2001, 66(11), 1615-1622.

Rosati et al., "Cephalosporins to carbapenems: 1-oxygenated carbapenems and carbapenams.", J. Med. Chem. 1990, 33(1), 291-297.

Rose et al., "Preclinical antitumor activity of water-soluble paclitaxel derivatives", Cancer Chemother. Pharmacol. 1997, 39(6), 486-492.

Salim et al., "Pharmacokinetic analysis of esteric prodrugs of valproic acid", Pharm. Res. 1990, 7(9), S222.

Sambasivarao et al., "Synthetic approach to pentaleno[2,1-b:5,4-b']diindoles", J. Org. Chem. 1990, 55(12), 3858-3866.

Sandham et al., "Synthesis and biological properties of novel glucocorticoid androstene C-17 furoate esters", Bioorg. Med. Chem. 2004, 12(19), 5213-5224.

Sandler et al., "Organic Functional Group Preparations", vol. 3; Academic Press: New York, 1972; pp. 372-381.

Satake et al., "The Reaction of Electron Excess Aromatic Heterocycle, 1,4-Dihydropyrrolo[3,2-b]pyrrole and Some Related Compounds with Chlorosulfonyl Isocyanate (CSI)", Heterocycles 1996, 43(11), 2361-2365.

Scott et al., "Preparation and Reductive Cyclization of Some Carbon-Alkylated Derivatives of Ethyl 3-Nitro-2-thienylpyruvate", J. Org. Chem. 1964, 29(8), 2165-2168.

Sergievskaya et al., "N-Bis(chloroethyl)amines with Alicyclic and Aromatic Radicals in the Molecules. II.", Zhurnal Obshchei Khimii 1958, 28, 1845-1849. [translation].

Severin et al., "Umsetzungen von Ketonen mit azavinylogen Säureamiden", Chem. Ber. 1975, 108(5), 1756-1767.

Sewald et al., "Synthesis of homochiral camphor annulated pyrrole derivatives", Tetrahedron Asymmetry 1996, 7(5), 1269-1272.

Sha et al., "Synthesis of 2,4-Dihydropyrrolo[3,4-b]pyrroles and 4,6-Dihydro-2H-dipyrrolo[3,4-b:3',4'-d]pyrroles", Heterocycles 1990, 31(4), 603-609.

Shaaya et al., "Anhydride prodrugs for nonsteroidal anti-inflammatory drugs", Pharm. Res. 2003, 20(2), 205-211.

Shek, "Chemical delivery systems and prodrugs of anticonvulsive drugs", Adv. Drug Deliv. Rev. 1994, 14(2-3), 227-241.

Shirai et al., "Reduction of 1-(m-methoxyphenyl)-4-oxocycloalkanecarbonitriles with lithium aluminum hydride", Nagoya-shiritsu Daigaku Yakugakubu Kenkyu Nenpo 1969, 17, 33-37.

Shirai et al., "Synthesis of spiro[4-hydroxycyclohexane-1,4,2',3'-dihydro-6'-methoxy-1'-substituted-2'-methyl-1'H-isoquinoline]", Chem. Pharm. Bull. 1972, 20(1), 41-46.

Shvedov et al., "Monoarylhydrazones of di- and tricarbonyl compounds in the Knorr synthesis of pyrroles", Khimiya Geterotsiklicheskikh Soedinenii 1972(3), 342-344. [translation].

Silvestri et al., "Simple, short peptide derivatives of a sulfonylindolecarboxamide (L-737,126) active in vitro against HIV-1 wild type and variants carrying non-nucleoside reverse transcriptase inhibitor resistance mutations.", J. Med. Chem. 2004, 47(15), 3892-3896.

Sivy et al., "Structure of a furo[3,2-b]pyrrole derivative", Acta Crystallogr. 1988, C44(11), 2032-2033.

Skolnick et al., "Antidepressant-like actions of DOV 21,947: a "triple" reuptake inhibitor", Eur. J. Pharmacol. 2003, 461(2-3), 99-104.

Slawik et al., "Lipophilicity of a series of 1,2-benzisothiazol-3(2H)-ones determined by reversed-phase thin-layer chromatography", J. Chromatogr. A 2002, 952(1-2), 295-299.

Sleath et al., "Synthesis of 7,9-didecarboxymethoxatin (4,5-dihydro-4,5-dioxo-1H-pyrrolo[2,3-f]quinoline-2-carboxylic acid) and comparison of its chemical properties with those of methoxatin and analogous o-quinones. Model studies directed toward the action of PQQ requiring bacterial oxidoreductases and mammalian plasma amine oxidase", J. Am. Chem. Soc. 1985, 107(11), 3328-3338.

Sleziak et al., "Furo[2,3-b]pyrrole Derivatives. Syntheses and Reactions in the Furan and Pyrrole Ring", Pol. J. Chem. 2000, 74(2), 207-217.

Sleziak et al., "Reactions of Furo[2,3-b]pyrrole and Furo[3,2-b]pyrrole-Type Aldehydes", Collect. Czech. Chem. Commun. 1999, 64(7), 1135-1146.

Smith et al., "Deacylation and deformylation of pyrroles", J. Org. Chem. 1983, 48(24), 4779-4781.

Snyder et al., "Synthesis of the Thieno [3,2-b]pyrrole System", J. Am. Chem. Soc. 1957, 79(10), 2556-2559.

Sohma et al., "Controlled Drug Release: Design and Application of New Water-soluble Prodrugs" in "Peptide Science 2001"; Aoyagi, H., Ed.; The Japanese Peptide Society, 2002; pp. 249-252.

Sorotskaya et al., "The Series of Substituted Butanolides and Butenolides. IV. 4-Arylidene(heteroarylidene)-2-butenolides", Zhurnal Organicheskoi Khimii 1989, 25(1), 175-182. [translation].

Soth et al., "Recherches en série hétérocyclique. XXIX. Sur des voies d'accès à des thiéno, sélénolo, furo et pyrrolopyrroles", Can. J. Chem. 1978, 56(10), 1429-1434.

Sparey et al., "The discovery of fused pyrrole carboxylic acids as novel, potent d-amino acid oxidase (DAO) inhibitors", Bioorg. Med. Chem. Lett. 2008, 18(11), 3386-3391.

STN Registry File No. 67268-37-5. Registry File. Retrieved from STN Mar. 17, 2008. One page.

Stuart et al., "Cobalt-mediated Alkylation of Siloxy Furans", Heterocycles 1991, 32(5), 949-963.

Svahn et al., "Tranexamic acid derivatives with enhanced absorption", J. Med. Chem. 1986, 29(4), 448-453.

Takahashi et al., "Asymmetric α-Substituted Phenethylamines. I. Synthesis of Optically Pure 1-Aryl-N-(2'-hydroxy-1'-isopropylethyl)-2-phenylethylamines", Chem. Pharm. Bull. 1982, 30(9), 3160-3166.

Tammara et al., "Morpholinoalkyl ester prodrugs of diclofenac: synthesis, in vitro and in vivo evaluation", J. Pharm. Sci. 1994, 83(5), 644-648.

Treibs et al., "Über einige Pyrrolderivate mit angegliedertem isocyclischem Ring. Bz-Tetrahydrindole und Cyclopentenopyrrole", Justus Liebigs Ann. Chem. 1935, 517, 152-169.

Trost et al., "Palladium-Catalyzed Enantioselective C-3 Allylation of 3-Substituted-1H-Indoles Using Trialkylboranes", J. Am. Chem. Soc. 2006, 128(19), 6314-6315.

Ueda et al., "Novel water soluble phosphate prodrugs of taxol® possessing in vivo antitumor activity", Bioorg. Med. Chem. Lett. 1993, 3(8), 1761-1766.

Ueda et al., "Novel, water-soluble phosphate derivatives of 2'-ethoxy carbonylpaclitaxel as potential prodrugs of paclitaxel: Synthesis and antitumor evaluation", Bioorg. Med. Chem. Lett. 1995, 5(3), 247-252.

Urbach et al., "Eine einfache diastereoselektive Synthese von (1SR,3SR,5SR)-2-Azabicyclo [3.3.0] octan-3-carbonsäure", Tetrahedron Lett. 1985, 26(15), 1839-1842.

van Herk et al., "Pyrazole Derivatives as Partial Agonists for the Nicotinic Acid Receptor", J. Med. Chem. 2003, 46(18), 3945-3951.

Vicini et al., "Biological studies on 1,2-benzisothiazole derivatives. I. Evaluation of antibacterial, antifungal and DNA-damaging activity", Farmaco 1989, 44(5), 511-517.

Vicini et al., "Sintesi e proprieta antiflogistiche antipiretiche ed analgesiche di 5-(1,2-benzisotiazolil)tetrazoli", Farmaco Sci. 1986, 41(2), 111-118.

Vicini et al., "Sintesi e proprieta antiflogistiche antipiretiche ed analgesiche di acidi 5-benzisotiazolilalcanoici e di loro derivati funzionali", Farmaco Sci. 1984, 39(10), 817-829.

Vippagunta et al., "Crystalline solids", Adv. Drug Deliv. Rev. 2001, 48(1), 3-26.

Viswanathan et al., "Free Radical-Mediated Aryl Amination and Its Use in a Convergent [3+2] Strategy for Enantioselective Indoline α-Amino Acid Synthesis", J. Am. Chem. Soc. 2003, 125(1), 163-168.
Vitali et al., "Ricerche nella classe dei fitocidi 3-benzisotiazolacetici", Farmaco Sci. 1973, 28(1), 8-18.
Vogel et al., "Cycloalkano-2H-pyrrole als stabile Zwischenstufen bei der Umwandlung von β-Cycloalkenyl-α-azidoacrylestern in Cycloalkano-1H-pyrrole", Angew. Chem. 1993, 105(7), 1116-1117.
Vogel et al., "Cycloalkano-2H-pyrrole as a Stable Intermediate in the Conversion of beta-Cycloalkenyl-alpha-azidoacrylates to Cycloalkano-1H pyrroles", Angew. Chem. Int. Ed. Engl. 1993, 32(7), 1051-1052. [translation of Angew. Chem. 1993, 105(7), 1116-1117.].
Wang et al., "Synthesis of ethyl cyclopenteno- or cyclohexeno[b]pyrrolyl-2-carboxylates", Youji Huaxue 1997, 17(6), 524-528.
Watanabe et al., "Enantioselective addition of chirally modified allylboranes to N-(trimethylsilyl)benzaldehyde imine", Tetrahedron Asymmetry 1995, 6(7), 1531-1534.
Welch et al., "Improved Syntheses of [3,2-b]- and [2,3-b]-fused Selenolo- and Thienopyrroles, and of Furo[3,2-b]pyrrole", Heterocycl. Comm. 1999, 5(4), 305-310.
Wen et al., "Cell differentiation enhancement by hydrophilic derivatives of 4,8-Dihydrobenzo[1,2-b:5,4-b']dithiophene-4,8-diones in HL-60 leukemia cells", Bioorg. Med. Chem. Lett. 2007, 17(10), 2908-2912.
Wensbo et al., "Indole-3-Acetic Acids and Hetero Analogues by One Pot Synthesis including Heck Cyclisation", Tetrahedron 1995, 51(37), 10323-10342.
Wensbo et al., "Indole-3-pyruvic acid oxime ethers and thieno analogues by Heck cyclisation. Application to the synthesis of thia-tryptophans", Tetrahedron 1996, 52(47), 14975-14988.
Wernly-Chung et al., "Structure-reactivity relationships in the chemical hydrolysis of prodrug esters of nicotinic acid", Int. J. Pharm. 1990, 63(2), 129-134.
West, A. R., "Solid State Chemistry and Its Applications"; Wiley: New York, 1988; pp. 358 and 365.
Wright et al., "Derivatives of 11-(1-piperazinyl)-5H-pyrrolo[2,1-c][1,4]benzodiazepine as central nervous system agents", J. Med. Chem. 1980, 23(4), 462-465.
Xue et al., "An Efficient Synthesis of Glycoprotein IIb/IIIa Inhibitor DMP728. A Novel Synthesis of N.alpha.-Methylarginine-Containing Peptide", J. Org. Chem. 1995, 60(4), 946-952.
Yardley et al., "2-Phenyl-2-(1-hydroxycycloalkyl)ethylamine derivatives: synthesis and antidepressant activity", J. Med. Chem. 1990, 33(10), 2899-2905.
Yarovenko et al., "Regioselective acylation of methyl 2-methyl-4H-thieno[3,2-b]pyrrole-5-carboxylate", Russ. Chem. Bull., Int. Ed., 2003, 52(2), 451-456.
Yasuhara et al., "Prodrugs of 3-(3,4-dichlorobenzyloxy)-2-amino-6-fluorobicyclo[3.1.0]hexane-2,6-dicarboxylic acid (MGS0039): A potent and orally active group II mGluR antagonist with antidepressant-like potential", Bioorg. Med. Chem. 2006, 14(12), 4193-4207.
Yevich et al., "Synthesis and biological evaluation of 1-(1,2-benzisothiazol-3-yl)- and (1,2-benzisoxazol-3-yl)piperazine derivatives as potential antipsychotic agents", J. Med. Chem. 1986, 29(3), 359-369.
Yu et al., "The regiospecific C-4 lithiation of 2-(tert-butyldimethylsilyl)-3-furoic acid", J. Chem. Soc., Perkin Trans. 1, 1991(10), 2600-2601.

Yudina et al., "Synthesis and alkylation of indolo[3,2-b]carbazoles", Tetrahedron 2003, 59(8), 1265-1275.
Zani et al., "Biological studies on 1,2-benzisothiazole derivatives. VI. Antimicrobial activity of 1,2-benzisothiazole and 1,2-benzisothiazolin-3-one derivatives and of some corresponding 1,2-benzisoxazoles", Farmaco 1996, 51(11), 707-713.
Zaragoza Dörwald, F., "Side Reactions in Organic Synthesis"; Wiley-VCH: Weinheim, 2005; pp. IX and 41.
Zhang et al., "Synthesize the china 3-pyridyl ester analogs of anaddicted analgesic Epibatidine", Journal of Shangqiu Teachers College (Shangqiu Shifan Xueyuan Xuebao) 2004, 20(5), 90-94.
Zhang et al., "Total synthesis of the porphyrin mineral abelsonite and related petroporphyrins with five-membered exocyclic rings", Tetrahedron Lett. 2003, 44(39), 7253-7256.
Zinoune et al., "Aminoalkylation of Aldehydes with Glyoxal N,N-Dimethlmonohydrazone Yields Stable 4-Substituted Pyrrolin-3-ones", Heterocycles 1989, 28(2), 1077-1084.
Zong et al., "A new and efficient synthetic route toward 3,4-alkylenedioxypyrrole (XDOP) derivatives via Mitsunobu chemistry", Tetrahedron Lett. 2006, 47(21), 3521-3523.
STN—Registry file [RN 132857-67-1 (Mar. 29, 1991), RN 109252-80-4 (Jul. 18, 1987), RN 93144-92-4 (Dec. 18, 1984), RN 92321-04-5 (Dec. 17, 1984), RN 83957-46-4 (Nov. 16, 1984), RN 83957-32-8 (Nov. 16, 1984), RN 69740-90-5 (Nov. 16, 1984), RN 69640-94-4 (Nov. 16, 1984), RN 69640-90-0 (Nov. 16 1984), RN 69640-89-7 (Nov. 16, 1984), RN 69640-88-6 (Nov. 16, 1984), RN 69640-87-5 (Nov. 16, 1984), RN 69640-86-4 (Nov. 16, 1984), RN 69640-85-3 (Nov. 16, 1984), RN 69640-84-2 (Nov. 16, 1984), RN 69640-83-1 (Nov. 16, 1984), RN 69640-82-0 (Nov. 16, 1984), RN 69640-80-8 (Nov. 16, 1984), RN 67313-00-2 (Nov. 16, 1984), RN 67312-99-6 (Nov. 16, 1984), RN 67312-98-5 (Nov. 16, 1984), RN 60068-34-0 (Nov. 16, 1984), RN 60068-33-9 (Nov. 16, 1984), RN 60068-32-8 (Nov. 16, 1984), RN 58379-13-8 (Nov. 16, 1984), RN 57955-60-9 (Nov. 16, 1984), RN 57955-59-6 (Nov. 16, 1984), RN 51074-73-8 (Nov. 16, 1984), RN 51074-72-7 (Nov. 16, 1984), RN 51074-71-6 (Nov. 16, 1984), RN 51074-69-2 (Nov. 16, 1984), RN 36373-65-6 (Nov. 16, 1984), RN 36373-63-4 (Nov. 16, 1984), RN 34779-69-6 (Nov. 16, 1984), RN 34779-67-4 (Nov. 16, 1984), RN 33317-36-1 (Nov. 16, 1984), RN 33317-33-8 (Nov. 16, 1984)].
Agrawal et al., 2002, "QSAR Study on Competition Binding of Rodenticides (PATs) to H1 Receptor in Rat and Guinea Pig Brain," Bioorg. Med. Chem., 10(9), 2913-18.
Agrawal et al., 2003, "Topological Modelling of Binding Affinity of 1-Phenyl-3-Amino-1,2,3,4-Tetrahydronaphthalenes as Ligands for Histamine H1 Receptors," Proc. Natl. Acad. Sci. India, Sec. A, Physical Sciences, 73(3), 283-96.
Asano et al., 2001, "The First Asymmetric Synthesis of a Dopamine D1 Agonist, Dihydrexidine, Employing Asymmetric Conjugate Addition Technology," Tetrahedron Lett., 42(48), 8493-95.
Morrison et al., 1950, "Synthetic Analgesics. Part X. Tertiary Carbinols and Derivatives from Mannich Bases," J. Chem. Soc., 1510-13.
Welch, et al., "Nontricyclic Antidepressant Agents Derived from cis- and trans-1-Amino-4-aryltetralines," J. Med. Chem., 1984, 27, 1508-1515.

* cited by examiner

TETRALONE-BASED MONOAMINE REUPTAKE INHIBITORS

CROSS REFERENCE TO RELATED APPLICATIONS

This application claims priority under 35 U.S.C. §119(e) to U.S. Provisional Patent Application No. 60/756,555, filed Jan. 5, 2005, which application is incorporated herein by reference in its entirety for all purposes.

FIELD OF THE INVENTION

The invention relates to compounds and compositions for the treatment of central nervous system (CNS) disorders.

BACKGROUND OF THE INVENTION

Psychiatric disorders are pathological conditions of the brain characterized by identifiable symptoms that result in abnormalities in cognition, emotion, mood, or affect. These disorders may vary in severity of symptoms, duration, and functional impairment. Psychiatric disorders afflict millions of people worldwide resulting in tremendous human suffering and economic burden due to lost productivity and dependent care.

Over the past several decades, the use of pharmacological agents to treat psychiatric disorders has greatly increased, largely due to research advances in both neuroscience and molecular biology. In addition, chemists have become increasingly sophisticated at creating chemical compounds that are more effective therapeutic agents with fewer side effects, targeted to correct the biochemical alterations that accompany mental disorders.

Yet, despite the many advances that have occurred, many psychiatric diseases remain untreated or inadequately treated with current pharmaceutical agents. In addition, many of the current agents interact with molecular targets not involved with the psychiatric disease. This indiscriminate binding can result in side effects that can greatly influence the overall outcome of therapy. In some cases the side effects are so severe that discontinuation of therapy is required.

Depression is an affective disorder, the pathogenesis of which cannot be explained by any single cause or theory. It is characterized by a persistently low mood or diminished interests in one's surroundings, accompanied by at least several of the following symptoms: reduced energy and motivation, difficulty concentrating, altered sleep and appetite, and at times, suicidal ideation (American Psychiatric Association: *Diagnostic and Statistical Manual of Mental Disorders*, ed. 4. Washington, American Psychiatric Association, 1994). Major depression is associated with high rates of morbidity and mortality, with suicide rates of 10-25% (Kaplan H I, Sadock B J (eds): *Synopsis of Psychiatry*. Baltimore, Williams & Wilkins, 1998, p. 866).

Depression is believed to result from dysfunction in the noradrenergic or serotonergic systems, more specifically, from a deficiency of certain neurotransmitters (NTs) at functionally important adrenergic or serotonergic receptors.

Neurotransmitters produce their effects as a consequence of interactions with specific receptors. Neurotransmitters, including norepinephrine (NE) and/or serotonin (5-hydroxytryptamine, or 5-HT), are synthesized in brain neurons and stored in vesicles. Upon a nerve impulse, NTs are released into the synaptic cleft, where they interact with various postsynaptic receptors. Regional deficiencies in the synaptic levels of 5-HT and/or NE are believed to be involved in the etiology of depression, wakefulness, and attention.

Norepinephrine is involved in regulating arousal, dreaming, and moods. Norepinephrine can also contribute to the regulation of blood pressure, by constricting blood vessels and increasing heart rate.

Serotonin (5-HT) is implicated in the etiology or treatment of various disorders. The most widely studied effects of 5-HT are those on the CNS. The functions of 5-HT are numerous and include control of appetite, sleep, memory and learning, temperature regulation, mood, behavior (including sexual and hallucinogenic behavior), cardiovascular function, smooth muscle contraction, and endocrine regulation. Peripherally, 5-HT appears to play a major role in platelet homeostasis and motility of the GI tract. The actions of 5-HT are terminated by three major mechanisms: diffusion; metabolism; and reuptake. The major mechanism by which the action of 5-HT is terminated is by reuptake through presynaptic membranes. After 5-HT acts on its various postsynaptic receptors, it is removed from the synaptic cleft back into the nerve terminal through an uptake mechanism involving a specific membrane transporter in a manner similar to that of other biogenic amines. Agents that selectively inhibit this uptake increase the concentration of 5-HT at the postsynaptic receptors and have been found to be useful in treating various psychiatric disorders, particularly depression.

Approaches to the treatment of depression over the years have involved the use of agents that increase the levels of NE and 5-HT, either by inhibiting their metabolism (e.g., monoamine oxidase inhibitors) or reuptake (e.g., tricyclic antidepressants or selective serotonin reuptake inhibitors (SSRIs)).

There are more than twenty (20) approved antidepressant drugs available in the United States. The classical tricyclic antidepressants (TCAs) currently available block primarily the uptake of NE and also, to varying degrees, the uptake of 5-HT, depending on whether they are secondary or tertiary amines. Tertiary amines such as imipramine and amitriptyline are more selective inhibitors of the uptake of 5-HT than of catecholamines, compared with secondary amines such as desipramine.

Selective serotonin reuptake inhibitors have been investigated as potential antidepressants. Fluoxetine (PROZAC®), sertraline (ZOLOFT®), and paroxetine (PAXIL®) are three examples of SSRIs currently on the U.S. market. These agents do not appear to possess greater efficacy than the TCAs, nor do they generally possess a faster onset of action; however, they do have the advantage of causing less side-effects. Of these three SSRIs, paroxetine is the most potent inhibitor of 5-HT uptake, fluoxetine the least. Sertaline is the most selective for 5-HT versus NE uptake, fluoxetine the least selective. Fluoxetine and sertraline produce active metabolites, while paroxetine is metabolized to inactive metabolites. The SSRIs, in general, affect only the uptake of serotonin and display little or no affinity for various receptor systems including muscarinic, adrenergic, dopamine, and histamine receptors.

In addition to treating depression, several other potential therapeutic applications for SSRIs have been investigated. They include treatment of Alzheimer's disease, aggressive behavior, premenstrual syndrome, diabetic neuropathy, chronic pain, fibromyalgia, and alcohol abuse. For example, fluoxetine is approved for the treatment of obsessive-compulsive disorder (OCD). Of particular significance is the observation that 5-HT reduces food consumption by increasing meal-induced satiety and reducing hunger, without producing the behavioral effects of abuse liability associated with amphetamine-like drugs. Thus, there is interest in the use of SSRIs in the treatment of obesity.

Venlafaxine (EFFEXOR®) is a dual-reuptake antidepressant that differs from the classical TCAs and the SSRIs chemically and pharmacologically in that it acts as a potent inhibitor of both 5-HT and NE uptake. Neither venlafaxine nor its major metabolite have a significant affinity for adrenergic alpha-1 receptors. Venlafaxine possesses an efficacy equivalent to that of the TCAs, and a benign side effect profile similar to those of the SSRIs.

Dopamine is hypothesized to play a major role in psychosis and certain neurodegenerative diseases, such as Parkinson's disease, where a deficiency in dopaminergic neurons is believed to be the underlying pathology. Dopamine affects brain processes that control movement, emotional response, and ability to experience pleasure and pain. Regulation of DA plays a crucial role in our mental and physical health. Certain drugs increase DA concentrations by preventing DA reuptake, leaving more DA in the synapse. An example is methylphenidate (RITALIN®), used therapeutically to treat childhood hyperkinesias and symptoms of schizophrenia. Dopamine abnormalities are believed to underlie some of the core attentional abnormalities seen in acute schizophrenics.

A therapeutic lag is associated with the use of these drugs. Patients must take a drug for at least three (3) weeks before achieving clinically meaningful symptom relief. Furthermore, a significant number of patients do not respond to current therapies at all. For example, it is currently estimated that up to thirty percent (30%) of clinically diagnosed cases of depression are resistant to all forms of drug therapy.

SUMMARY OF THE INVENTION

The present invention relates to novel tetralone-based amines and salts thereof. It further relates to novel pharmaceutical compositions, and their use in the treatment of CNS disorders such as depression (e.g., major depressive disorder, bipolar disorder), fibromyalgia, pain (e.g., neuropathic pain), sleep apnea, attention deficit disorder (ADD), attention deficit hyperactivity disorder (ADHD), restless leg syndrome, schizophrenia, anxiety, obsessive compulsive disorder, post-traumatic stress disorder, seasonal affective disorder (SAD), premenstrual dysphoria as well as neurodegenerative disease (e.g., Parkinson's disease, Alzheimer's disease).

Hence, in a first aspect the invention provides a compound having a structure according to Formula (I):

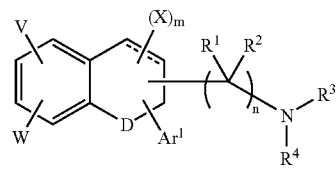

(I)

In Formula (I), n is an integer selected from 0 to 2. D is a member selected from the group consisting of $CX_2$, $CX-Ar^1$, $CX-(CR^1R^2)_nNR^3R^4$, $N-Ar^1$ and $N-(CR^1R^2)_nNR^3R^4$. The integer m is selected from 0 to 6, with the proviso that when D is $N-Ar^1$ or $N-(CR^1R^2)_nNR^3R^4$, then m is not greater than 5. Each X is a member independently selected from the group consisting of H, halogen, CN, $CF_3$, $OR^5$, $SR^5$, $S(O)_2R^5$, $NR^6R^7$, $NR^6S(O)_2R^5$, $NR^6C(O)R^5$, acyl, $=X^1$, substituted or unsubstituted alkyl, substituted or unsubstituted heteroalkyl, substituted or unsubstituted aryl, substituted or unsubstituted heteroaryl, and substituted or unsubstituted heterocycloalkyl. $X^1$ is a member selected from the group consisting of O, S, and $NOR^{5'}$ wherein $R^{5'}$ is a member selected from the group consisting of H, substituted or unsubstituted alkyl and substituted or unsubstituted heteroalkyl. Each $R^5$, $R^6$ and $R^7$ is a member independently selected from the group consisting of H, acyl, substituted or unsubstituted alkyl, substituted or unsubstituted heteroalkyl, substituted or unsubstituted aryl and substituted or unsubstituted heteroaryl, wherein $R^6$ and $R^7$, together with the atoms to which they are attached, are optionally joined to form a 3- to 7-membered ring.

$Ar^1$ in Formula (I) is a member selected from the group consisting of substituted or unsubstituted aryl, substituted or unsubstituted heteroaryl and a fused ring system. V and W are members independently selected from the group consisting of H, halogen, $CF_3$, CN, $OR^9$, $SR^9$, $S(O)_2R^9$, $NR^{10}R^{11}$, $NR^{10}S(O)_2R^9$, $NR^{10}C(O)R^9$, acyl, substituted or unsubstituted alkyl, substituted or unsubstituted heteroalkyl, substituted or unsubstituted aryl, substituted or unsubstituted heteroaryl, and substituted or unsubstituted heterocycloalkyl, wherein V and W, together with the atoms to which they are attached, are optionally joined to form a 5- to 7-membered ring. Each $R^9$, $R^{10}$ and $R^{11}$ is a member independently selected from the group consisting of H, substituted or unsubstituted alkyl, substituted or unsubstituted heteroalkyl, substituted or unsubstituted aryl, substituted or unsubstituted heteroaryl, substituted or unsubstituted heterocycloalkyl, wherein $R^{10}$ and $R^{11}$, together with the atoms to which they are attached, are optionally joined to form a 3- to 7-membered ring.

In Formula (I), each $R^1$ and $R^2$ is a member independently selected from the group consisting of H, halogen, CN, $CF_3$, $OR^{12}$, substituted or unsubstituted alkyl, substituted or unsubstituted heteroalkyl, substituted or unsubstituted aryl, substituted or unsubstituted heteroaryl and substituted or unsubstituted heterocycloalkyl, wherein $R^{12}$ is a member selected from the group consisting of H, substituted or unsubstituted alkyl, substituted or unsubstituted heteroalkyl, substituted or unsubstituted aryl, substituted or unsubstituted heteroaryl and substituted or unsubstituted heterocycloalkyl.

$R^3$ and $R^4$ are members independently selected from the group consisting of H, $OR^{13}$, acyl, $S(O)_2R^{14}$, substituted or unsubstituted alkyl, substituted or unsubstituted heteroalkyl, substituted or unsubstituted aryl, substituted or unsubstituted heteroaryl and substituted or unsubstituted heterocycloalkyl, wherein $R^{13}$ is a member selected from the group consisting of H, substituted or unsubstituted alkyl, substituted or unsubstituted heteroalkyl, substituted or unsubstituted aryl, substituted or unsubstituted heteroaryl and substituted or unsubstituted heterocycloalkyl. $R^{14}$ is a member selected from the group consisting of substituted or unsubstituted alkyl, substituted or unsubstituted heteroalkyl, substituted or unsubstituted aryl, substituted or unsubstituted heteroaryl and substituted or unsubstituted heterocycloalkyl.

At least two of $R^1$, $R^2$, $R^3$ and $R^4$, together with the atoms to which they are attached, are optionally joined to form a 3- to 7-membered ring.

The compound of the invention can be chiral, racemic or be present in a composition including one or more stereoisomer, such as an enantiomerically or diastereomerically enriched mixture.

In a second aspect, the invention provides a pharmaceutical composition including a compound of the invention or a pharmaceutically acceptable salt or solvate thereof, and a pharmaceutically acceptable carrier, vehicle, diluent or combination thereof.

In a third aspect, the invention provides a method for treating a central nervous system disorder. The method includes administering to a subject in need thereof a therapeutically effective amount of a compound of the invention or a pharmaceutically acceptable salt or solvate thereof.

In another aspect, the invention relates to a method of inhibiting reuptake of one or more monoamine from the synaptic cleft. The method includes administering to a mammalian subject a compound of the invention or a pharmaceutically acceptable salt or solvate thereof.

In yet another aspect, the invention provides a method of modulating one or more monoamine transporter. The method includes administering to a mammalian subject a compound of the invention, or a pharmaceutically acceptable salt or solvate thereof.

DETAILED DESCRIPTION OF THE INVENTION

I. Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O——Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2$R'— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, S, Si and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g, aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted alkyl, substituted or unsubstituted heteroalkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: substituted or unsubstituted alkyl, substituted or unsubstituted heteroalkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$-D-, wherein A and D are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X"—(CR"R"')$_d$—, where s and d are independently integers of from 0 to 3, and X" is —O—, —NR'—, —S—, —S(O)—, —S(O)$_2$—, or —S(O)$_2$NR'—. The substituents R, R', R" and R"' are preferably independently selected from hydrogen or substituted or unsubstituted (C$_1$-C$_6$)alkyl.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si) and boron (B).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocycloalkyl groups.

The phrase "therapeutically effective amount" as used herein means that amount of a compound, or composition comprising a compound of the present invention which is effective for producing some desired therapeutic effect (e.g., by inhibiting reuptake of a monoamine from the synaptic cleft of a mammal, thereby modulating the biological consequences of that pathway in the treated organism) at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, sulfamate, bisulfate, phosphate, nitrate, acetate, valerate, oleate, palmitate, stearate, laurate, benzoate, lactate, tosylate, citrate, maleate, ascorbate, palmitate, fumarate, succinate, tartrate, napthylate, mesylate, hydroxymaleate, phenylacetate, glutamate, glucoheptonate, salicyclate, sulfanilate, 2-acetoxybenzoate, methanesulfonate, ethane disulfonate, oxalate, isothionate, lactobionate, and laurylsulphonate salts and the like. See, for example, Berge et al. (1977) "Pharmaceutical Salts", *J Pharm. Sci.* 66:1-19.

The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science,* 66: 1-19 (1977)). Certain specific compounds of the present invention contain both basic and acidic finctionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention. "Compound or a pharmaceutically acceptable salt or solvate of a compound" intends the inclusive meaning of "or", in that a material that is both a salt and a solvate is encompassed.

Certain compounds of the present invention possess asymmetric carbon atoms (optical centers) or double bonds; the racemates, diastereomers, geometric isomers and individual isomers are encompassed within the scope of the present invention. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr, *J Chem. Ed.,* 62: 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but not implying any absolute stereochemistry; and wedge outlines and dotted or broken lines denote enantiomerically pure compounds of indeterminate absolute configuration.

The terms "enantiomeric excess" and "diastereomeric excess" are used interchangeably herein. Compounds with a single stereocenter are referred to as being present in "enantiomeric excess," those with at least two stereocenters are referred to as being present in "diastereomeric excess."

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The term "central nervous system disorder" refers to any abnormal condition of the central nervous system of a mammal. Central nervous system disorder includes neurodegenerative diseases such Alzheimer's disease and Parkinson's disease, neuropsychiatric diseases (e.g. schizophrenia), anxieties, sleep disorders, depression, dementias, movement disorders, psychoses, alcoholism, post-traumatic stress disorder and the like. "Central nervous system disorder" also includes any condition associated with the disorder, such as loss of memory and/or loss of cognition. For instance, a method of treating a neurodegenerative disease would also include treating or preventing loss of neuronal function characteristic of such disease. "Central nervous system disorder" also includes any disease or condition that is implicated, at least in part, in monoamine (e.g., norepinephrine) signaling pathways (e.g., cardiovascular disease).

The term "pain" refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic neuropathy (see, e.g., Harrison's Principles of Internal Medicine, pp. 93-98 (Wilson et al., eds., 12th ed. 1991); Williams et al., *J of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia.

II. Introduction

One strategy to develop effective therapies is the use of broad spectrum antidepressants that simultaneously inhibit the reuptake of more than one biogenic amine, such as serotonin (5-HT), norepinephrine (NE) and dopamnine (DA). The rationale for this approach is based upon clinical and preclinical evidence showing that deficiencies in dopaminergic function can be correlated with anhedonia, which is a core symptom of depression. Baldessarini, R. J., "Drugs and the Treatment of Psychiatric Disorders: Depression and Mania, in Goodman and Gilman's The Pharmacological Basis of Therapeutics 431-459 (9$^{th}$ ed 1996) Hardman et. al. eds.

An advantage of the compounds and compositions of the present invention is their ability to increase synaptic availability of three neurotransmitters, NE, 5-HT and DA by inhibiting their reuptake from the synaptic cleft. Skolnick and coworkers report on a body of preclinical evidence suggesting that the therapeutic profile of an antidepressant concurrently increasing the synaptic availability of DA, NE and 5-HT will differ from a compound inhibiting only NE and/or 5-HT. Skolnick, P.; Popik, P.; Janowsky, A.; Beer, B.; Lippa, A. S. "Antidepressant-like actions of DOV-21,947: a "triple" reuptake inhibitor," *Eur. J. Pharm.* 2003, 461, 103.

For example, Skolnick and coworkers have reported that a compound, DOV 21,947 ((+)-1-(3,4-dichlorophenyl)-3-azabicyclo[3.1.0]hexane), inhibits the reuptake of serotonin, norepinephrine, and dopamine in human embryonic kidney (HEK293) cells expressing the corresponding human recombinant transporters (IC$_{50}$ values of 12, 23 and 96 nM, respectively). Skolnick, P.; Popik, P.; Janowsky, A.; Beer, B.; Lippa, A. S. "Antidepressant-like actions of DOV-21,947: a "triple" reuptake inhibitor," *Eur. J. Pharm.* 2003, 461, 99. In addition, DOV 21,947 reduces the duration of immobility in the forced swim test (in rats) and also produces a dose-dependent reduction in immobility in the tail suspension test. Skolnick, P.; Popik, P.; Janowsky, A.; Beer, B.; Lippa, A. S., *Eur. J. Pharm.* 2003, 461, 99. Additional evidence can be found in preclinical data for new triple reuptake inhibitors such as DOV 21,947 in, e.g., U.S. Pat. No. 6,372,919, wherein DOV 21,947 was disclosed as having a significantly greater affinity for the norepinephrine and serotonin uptake sites than the racemic compound, (+)-1-(3,4-dichlorophenyl)-3-azabicyclo[3.1.0]hexane.

Taken together, the preclinical data for compounds such as DOV 21,947 indicate that dual or triple reuptake inhibitors may hold potential as novel treatments for depression in the clinic.

III. Compositions

A. Tetralone Based Amines

In a first aspect, the invention provides a compound having a structure according to Formula (I):

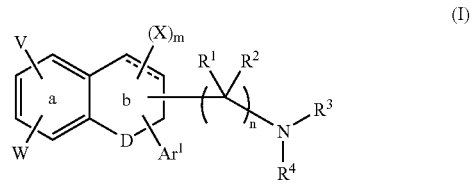

Each compound of Formula (I) includes at least one substituent —Ar$^1$ and at least one nitrogen-containing substituent:

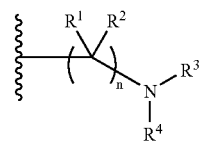

attached to ring b.

In Formula (I), n is an integer selected from 0 to 2. D is a member selected from the group consisting of CX$_2$, CX—Ar$^1$, CX—(CR$^1$R$^2$)$_n$NR$^3$R$^4$, N—Ar$^1$ and N—(CR$^1$R$^2$)$_n$NR$^3$R$^4$. The 6-membered, non-aromatic ring b of Formula (I) can be mono- or disubstituted at each of the positions of the ring, which is not part of ring a. In an exemplary embodiment, ring b includes up to 6 substituents X, preferably up to 4 substituents X, and more preferably up to 2 substituents X, wherein each X is independently selected. Thus, m is an integer selected from 0 to 6, with the proviso that when D is N—Ar$^1$ or N—(CR$^1$R$^2$)$_n$NR$^3$R$^4$, then m is not greater than 5.

Each X is a member independently selected from the group consisting of H, halogen, CN, CF$_3$, OR$^5$, SR$^5$, S(O)$_2$R$^5$, NR$^6$R$^7$, NR$^6$S(O)$_2$R$^5$, NR$^6$C(O)R$^5$, acyl, =X$^1$, substituted or unsubstituted alkyl, substituted or unsubstituted heteroalkyl, substituted or unsubstituted aryl, substituted or unsubstituted heteroaryl, and substituted or unsubstituted heterocycloalkyl. X$^1$ is a member selected from the group consisting of O, S, and NOR$^{5'}$ wherein R$^{5'}$ is a member selected from the group consisting of H, substituted or unsubstituted alkyl and substituted or unsubstituted heteroalkyl. Each R$^5$, R$^6$ and R$^7$ is a member independently selected from the group consisting of H, acyl, substituted or unsubstituted alkyl, substituted or unsubstituted heteroalkyl, substituted or unsubstituted aryl and substituted or unsubstituted heteroaryl, wherein R$^6$ and R$^7$, together with the atoms to which they are attached, are optionally joined to form a 3- to 7-membered ring. In one embodiment, two of R$^5$, R$^6$, and R$^7$, together with the atoms to which they are attached, are optionalally joined to form a 3- to 7-membered ring.

Ar¹ in Formula (I) is a member selected from the group consisting of substituted or unsubstituted aryl, substituted or unsubstituted heteroaryl and a fused ring system. V and W are aryl group substituents. In an exemplary embodiment V and W are members independently selected from the group consisting of H, halogen, $CF_3$, CN, $OR^9$, $SR^9$, $S(O)_2R^9$, $NR^{10}R^{11}$, $NR^{10}S(O)_2R^9$, $NR^{10}C(O)R^9$, acyl, substituted or unsubstituted alkyl, substituted or unsubstituted heteroalkyl, substituted or unsubstituted aryl, substituted or unsubstituted heteroaryl, and substituted or unsubstituted heterocycloalkyl, wherein V and W, together with the atoms to which they are attached, are optionally joined to form a 5- to 7-membered ring. Each $R^9$, $R^{10}$ and $R^{11}$ is a member independently selected from the group consisting of H, substituted or unsubstituted alkyl, substituted or unsubstituted heteroalkyl, substituted or unsubstituted aryl, substituted or unsubstituted heteroaryl, substituted or unsubstituted heterocycloalkyl, wherein $R^{10}$ and $R^{11}$, together with the atoms to which they are attached, are optionally joined to form a 3- to 7-membered ring. In one embodiment, two of $R^9$, $R^{10}$, and $R^{11}$, together with the atoms to which with the atoms to which they are attached, are optionalally joined to form a 3- to 7-membered ring.

In Formula (I), each $R^1$ and $R^2$ is a member independently selected from the group consisting of H, halogen, CN, $CF_3$, $OR^{12}$, substituted or unsubstituted alkyl, substituted or unsubstituted heteroalkyl, substituted or unsubstituted aryl, substituted or unsubstituted heteroaryl and substituted or unsubstituted heterocycloalkyl, wherein $R^{12}$ is a member selected from the group consisting of H, substituted or unsubstituted alkyl, substituted or unsubstituted heteroalkyl, substituted or unsubstituted aryl, substituted or unsubstituted heteroaryl and substituted or unsubstituted heterocycloalkyl.

$R^3$ and $R^4$ are members independently selected from the group consisting of H, $OR^{13}$, acyl, $S(O)_2R^{14}$, substituted or unsubstituted alkyl, substituted or unsubstituted heteroalkyl, substituted or unsubstituted aryl, substituted or unsubstituted heteroaryl and substituted or unsubstituted heterocycloalkyl, wherein $R^{13}$ is a member selected from the group consisting of H, substituted or unsubstituted alkyl, substituted or unsubstituted heteroalkyl, substituted or unsubstituted aryl, substituted or unsubstituted heteroaryl and substituted or unsubstituted heterocycloalkyl. $R^{14}$ is a member selected from the group consisting of substituted or unsubstituted alkyl, substituted or unsubstituted heteroalkyl, substituted or unsubstituted aryl, substituted or unsubstituted heteroaryl and substituted or unsubstituted heterocycloalkyl.

At least two of $R^1$, $R^2$, $R^3$ and $R^4$, together with the atoms to which they are attached, are optionally joined to form a 3- to 7-membered ring.

The compound of the invention can be chiral, racemic or be present in a composition including one or more stereoisomer.

In an exemplary embodiment, the compound of the invention has a structure, which is a member selected from Formula (II), Formula (III), Formula (IV) and Formula (V):

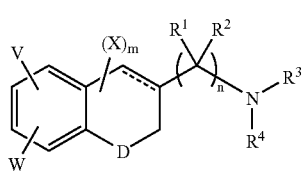
(II)

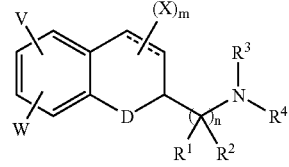
(III)

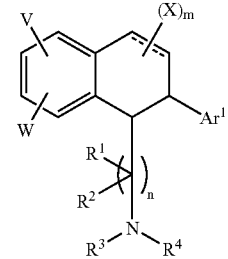
(IV)

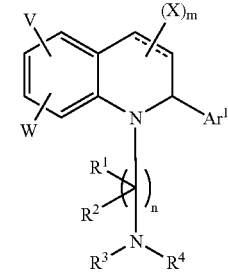
(V)

wherein D is CX—Ar¹ or N—Ar¹. In Formulae (II) to (V), Ar¹, X, V, W, D, $R^1$, $R^2$, $R^3$, $R^4$ and the integers m and n are as defined above.

In a preferred embodiment, Ar¹ in Formulae (I) to (V) is a member selected from substituted or unsubstituted phenyl and substituted or unsubstituted naphthyl. Particularly preferred are those compounds of the invention in which Ar¹ has the structure:

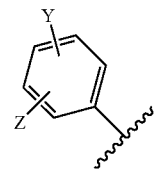

wherein Y and Z are aryl group substituents. In one embodiment, Y and Z are members independently selected from the group consisting of H, halogen, $CF_3$, CN, $OR^{16}$, $NR^{17}R^{18}$, $NR^{17}S(O)_2R^{16}$, $NR^{17}C(O)R^{16}$, $S(O)_2R^{16}$, acyl, substituted or unsubstituted alkyl, substituted or unsubstituted heteroalkyl, substituted or unsubstituted aryl, substituted or unsubstituted heteroaryl, and substituted or unsubstituted heterocycloalkyl, wherein Y and Z, together with the atoms to which they are attached, are optionally joined to form a 5- to 7-membered ring. In one embodiment, Y and Z are members independently selected from the group consisting of H, halogen, $CF_3$, CN, $OR^{16}$, $NR^{17}R^{18}$, $NR^{17}S(O)_2R^{16}$, $NR^{17}C(O)R^{16}$, acyl, substituted or unsubstituted alkyl, substituted or unsubstituted heteroalkyl, substituted or unsubstituted aryl, substituted or unsubstituted heteroaryl, and substituted or unsubstituted heterocycloalkyl, wherein Y and Z, together with the atoms to which they are attached, are optionally joined to form a 5- to 7-membered ring.

Each $R^{16}$, $R^{17}$ and $R^{18}$ is a member independently selected from the group consisting of H, substituted or unsubstituted alkyl, substituted or unsubstituted heteroalkyl, substituted or unsubstituted aryl, substituted or unsubstituted heteroaryl, and substituted or unsubstituted heterocycloalkyl. $R^{17}$ and $R^{18}$, together with the atoms to which they are attached, are optionally joined to form a 3- to 7-membered ring. In an exemplary embodiment, Y and Z are members independently selected from the group consisting of H, halogen, CN and $CF_3$.

In another exemplary embodiment, $Ar^1$ is a 4,3-substituted phenyl moiety having the structure:

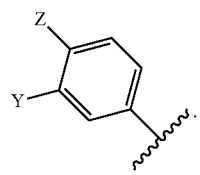

Exemplary compounds according to this embodiment are provided below:

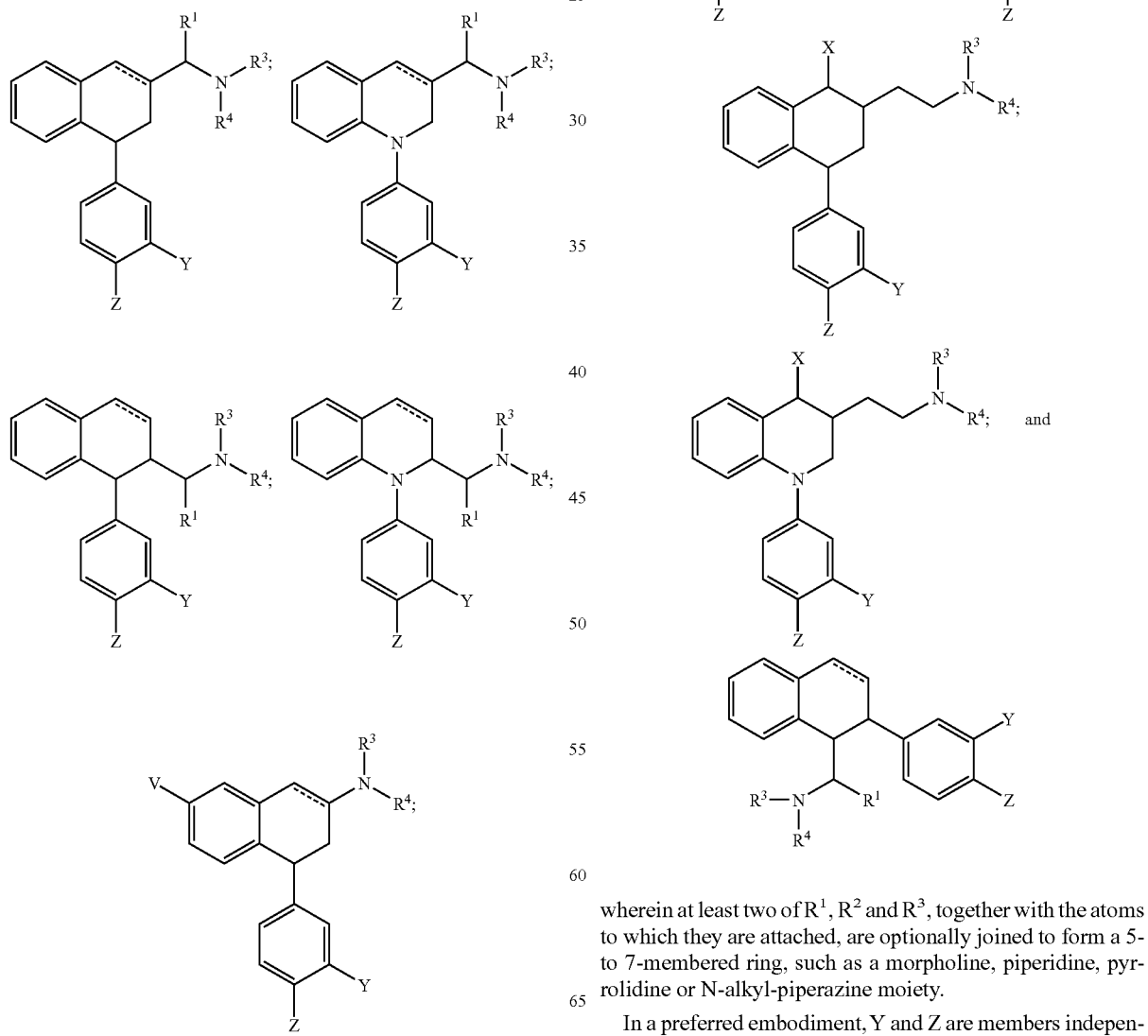

wherein at least two of $R^1$, $R^2$ and $R^3$, together with the atoms to which they are attached, are optionally joined to form a 5- to 7-membered ring, such as a morpholine, piperidine, pyrrolidine or N-alkyl-piperazine moiety.

In a preferred embodiment, Y and Z are members independently selected from H, halogen, CN, $CF_3$ and $OR^6$. In a particular preferred embodiment, Y and Z are both halogen. In an exemplary embodiment, Ar$^1$ in Formulae (I) to (V) is 3,4-dichlorophenyl.

In another preferred embodiment, m in Formulae (I) to (V) is 1; X is H or OR$^5$ (e.g., OH). In an exemplary embodiment, R$^3$ and R$^4$ are independently H or substituted or unsubstituted C$_1$-C$_4$ alkyl or C$_1$-C$_4$ heteroalkyl.

B. Compositions Including Stereoisomers

Compounds of the invention may exist in particular geometric or stereoisomeric forms. The invention contemplates all such compounds, including cis- and trans-isomers, (−)- and (+)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts may be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

As used herein, the term "enantiomerically enriched" or "diastereomerically enriched" refers to a compound having an enantiomeric excess (ee) or a diastereomeric excess (de) greater than about 50%, preferably greater than about 70% and more preferably greater than about 90%. In general, higher than about 90% enantiomeric or diastereomeric purity is particularly preferred, e.g., those compositions with greater than about 95%, greater than about 97% and greater than about 99% ee or de.

The terms "enantiomeric excess" and "diastereomeric excess" are used interchangeably herein. Compounds with a single stereocenter are referred to as being present in "enantiomeric excess", those with at least two stereocenters are referred to as being present in "diastereomeric excess".

For example, the term "enantiomeric excess" is well known in the art and is defined as:

$$ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racemic and 100 being enantiomerically pure. A compound which in the past might have been called 98% optically pure is now more precisely characterized by 96% ee. A 90% ee reflects the presence of 95% of one enantiomer and 5% of the other(s) in the material in question.

Hence, in one embodiment, the invention provides a composition including a first stereoisomer and at least one additional stereoisomer of a compound of the invention. The first stereoisomer may be present in a diastereomeric or enantiomeric excess of at least about 80%, preferably at least about 90% and more preferably at least about 95%. In a particularly preferred embodiment, the first stereoisomer is present in a diastereomeric or enantiomeric excess of at least about 96%, at least about 97%, at least about 98%, at least about 99% or at least about 99.5%. Enantiomeric or diastereomeric excess may be determined relative to exactly one other stereoisomer, or may be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

C. Synthesis of the Compounds

Compounds of the invention may be synthesized according to Schemes 1 to 11, below. It is within the abilities of a person skilled in the art to select appropriate alternative reagents replacing the exemplary reagents shown in Schemes 1-11 in order to synthesize a desired compound of the invention. It is also within the abilities of a skilled artisan to omit or add synthetic steps when necessary. As a non-limiting example, Ar in Schemes 1 to 11 is 3,4-dichlorophenyl. Exemplary compound numbers are based on Ar being 3,4-dichlorophenyl.

Scheme 1: Exemplary synthetic routes useful for the preparation of compounds of the invention

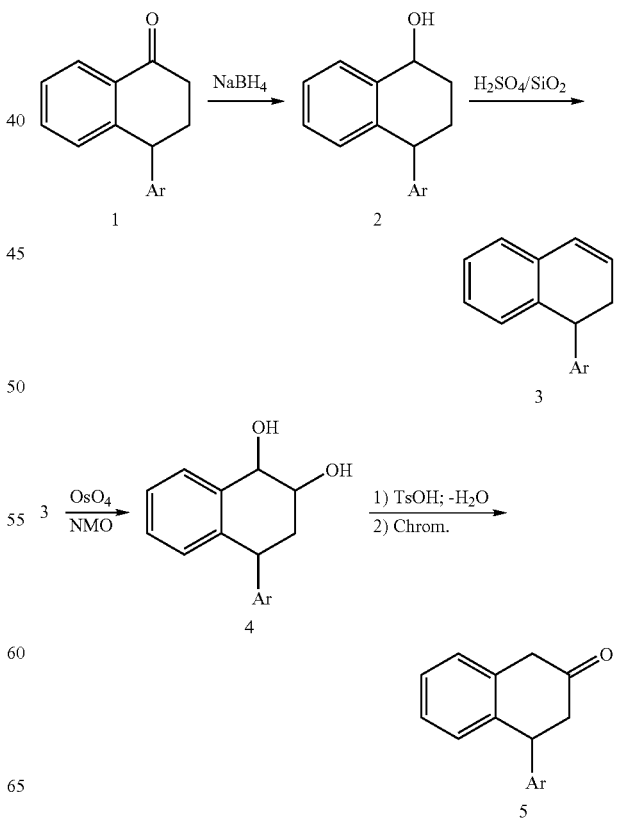

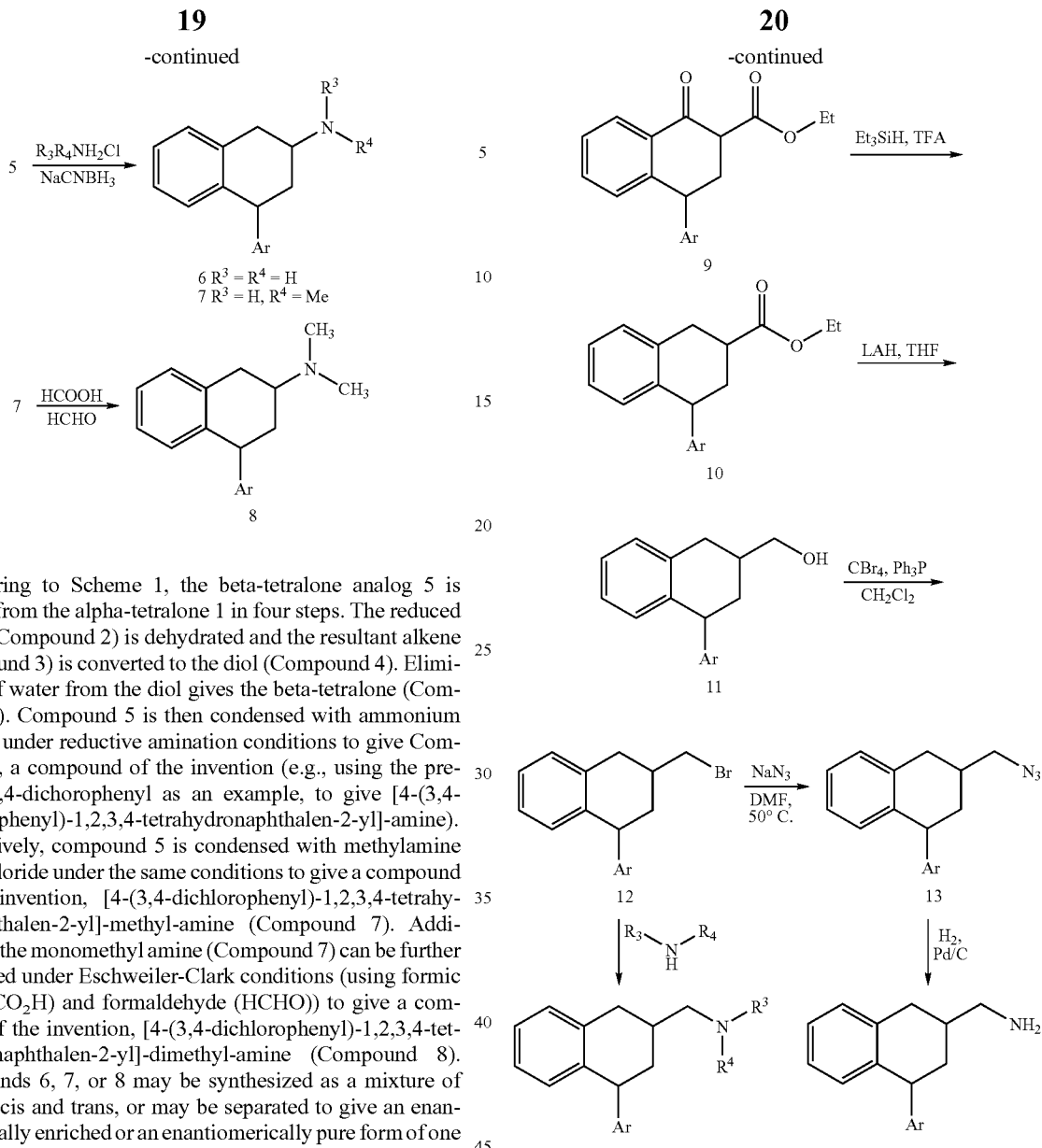

Referring to Scheme 1, the beta-tetralone analog 5 is derived from the alpha-tetralone 1 in four steps. The reduced ketone (Compound 2) is dehydrated and the resultant alkene (Compound 3) is converted to the diol (Compound 4). Elimination of water from the diol gives the beta-tetralone (Compound 5). Compound 5 is then condensed with ammonium chloride under reductive amination conditions to give Compound 6, a compound of the invention (e.g., using the preferred 3,4-dichorophenyl as an example, to give [4-(3,4-dichlorophenyl)-1,2,3,4-tetrahydronaphthalen-2-yl]-amine). Alternatively, compound 5 is condensed with methylamine hydrochloride under the same conditions to give a compound of the invention, [4-(3,4-dichlorophenyl)-1,2,3,4-tetrahydronaphthalen-2-yl]-methyl-amine (Compound 7). Additionally, the monomethyl amine (Compound 7) can be further elaborated under Eschweiler-Clark conditions (using formic acid ($HCO_2H$) and formaldehyde (HCHO)) to give a compound of the invention, [4-(3,4-dichlorophenyl)-1,2,3,4-tetrahydronaphthalen-2-yl]-dimethyl-amine (Compound 8). Compounds 6, 7, or 8 may be synthesized as a mixture of racemic cis and trans, or may be separated to give an enantiomerically enriched or an enantiomerically pure form of one of its four isomers. Cis and trans assignments may be made using methods known in the art (e.g., on the basis of NMR coupling patterns). The absolute configuration can, for instance, be determined by synthesis from a precursor of known configuration, or by X-ray crystallographic determination using a suitable crystal of the compound.

In another exemplary embodiment, compounds of the invention may be synthesized according to Scheme 2 below:

Scheme 2: Exemplary synthetic routes useful for the preparation of compounds of the invention

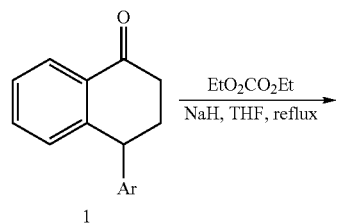

Referring to Scheme 2, acylation of the alpha-tetralone 4-(3,4-dichlorophenyl)-3,4-dihydro-2H-naphthalen-1-one (Compound 1) with diethylcarbonate was followed by reduction with triethylsilane to give 4-(3,4-dichlorophenyl)-1,2,3,4-tetrahydronaphthalene-2-carboxylic acid ethyl ester (Compound 10). Reduction and conversion to 3-bromomethyl-1-(3,4-dichlorophenyl)-1,2,3,4-tetrahydronaphthalene (Compound 12) is followed by alkylation with sodium azide in DMF to give 3-azidomethyl-1-(3,4-dichlorophenyl)-1,2,3,4-tetrahydronaphthalene (Compound 13). Chiral separation of Compound 13 is followed by hydrogenation to give a compound of the invention, C-[4-(3,4-dichlorophenyl)-1,2,3,4-tetrahydronaphthalen-2-yl]-methylamine (Compound 14). Alternatively, reduction and conversion to 3-bromomethyl-1-(3,4-dichlorophenyl)-1,2,3,4-tetrahydronaphthalene (Compound 12) is followed by alkylation with substituted amines to give 1-phenyl-3-aminoalkyl-1,2,3,4-tetrahydronaphthalenes (Compound 15).

In yet another exemplary embodiment, compounds of the invention may be synthesized according to Scheme 3 below:

Scheme 3: Exemplary synthetic route useful for the preparation of compounds of the invention

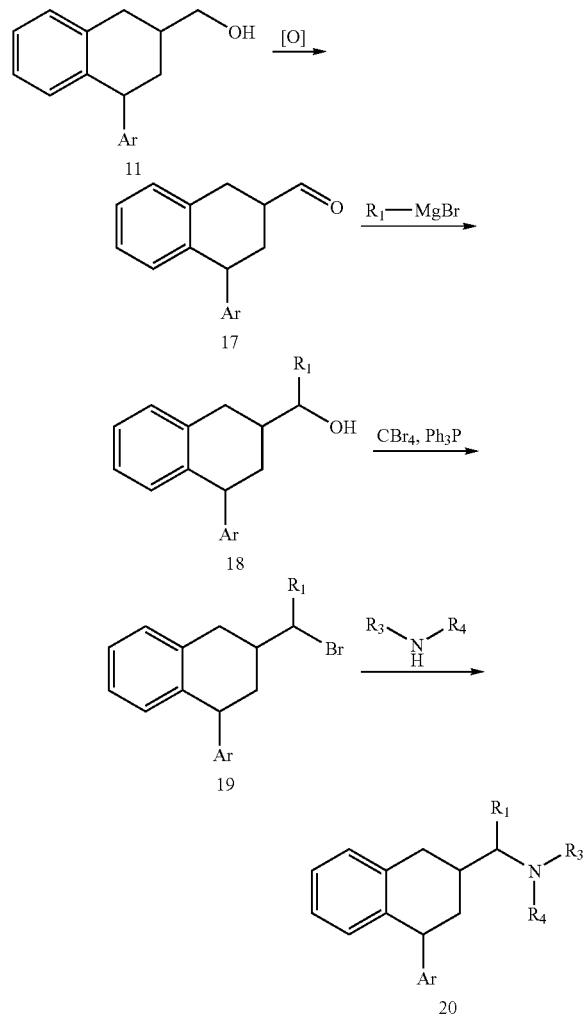

Referring to Scheme 3, oxidation of [4-(3,4-dichloro-phenyl)-1,2,3,4-tetrahydro-naphthalen-2-yl]-methanol (Compound 11 in Scheme 2) is followed by addition of alkyl Grignard agents and bromination to give substituted 3-bromomethyl-1-(3,4-dichlorophenyl)-1,2,3,4-tetrahydronaphthalenes (Compound 19). Displacement with substituted amines gives the desired alpha-substituted amines (Compound 20).

Alternatively, the compounds of the invention may be synthesized according to Scheme 4 below:

Scheme 4: Exemplary synthetic route useful for the preparation of compounds of the invention

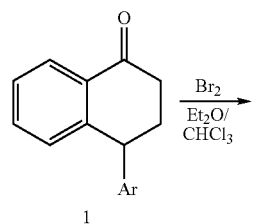

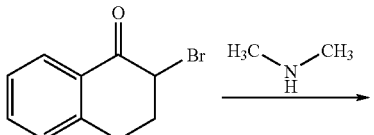

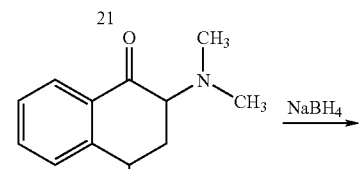

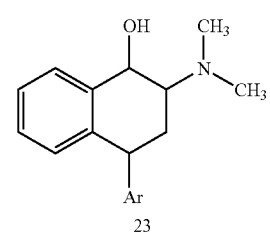

Referring to Scheme 4, synthesis of the amino alcohol starts from Compound 1. Exposure of the ketone to bromine gives the bromoketone (Compound 21) in quantitative yield. The bromoketone is reacted with dimethylamine to afford Compound 22, which is reduced with sodium borohydride to give a mixture of diastereomers of the amino alcohol (Compound 23). In one embodiment, separation of the diastereomers is accomplished using a combination of silicagel and chiral column chromatography.

Alternatively, the compounds of the invention may be synthesized according to Scheme 5 below:

Scheme 5: Exemplary synthetic route useful for the preparation of compounds of the invention

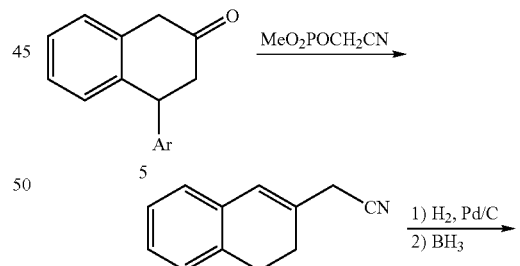

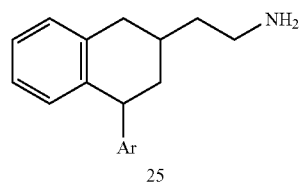

Referring to Scheme 5, the beta-tetralone 5 is alkylated and reduced to give 2-(1,3-cis)-1-(3,4-dichlorophenyl)-1,2,3,4-tetrahydronaphthalen-3-yl)ethanamine (Compound 25). The two diastereomers of Compound 25 can be separated, for instance, as their BOC derivatives using a chiral column.

In yet another example, the compounds of the invention may be synthesized according to Scheme 6 below:

Scheme 6: Exemplary synthetic routes useful for the preparation of compounds of the invention

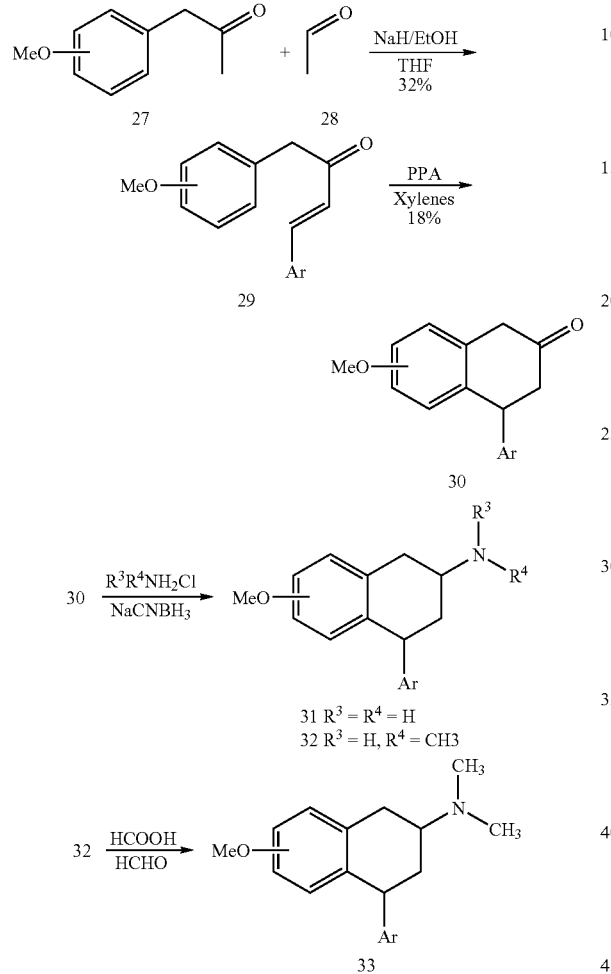

Referring to Scheme 6, the methoxybenzophenone is condensed with the aryl aldehyde and the resultant enone is cyclized by the action of PPA. The substituted beta-tetralone 30 may be treated with ammonium chloride or methylamine hydrochloride under reductive-amination conditions to give the amines 31 and 32. The dimethylamine 33 can be prepared by methylation of the methylamine using Eschweiler-Clark conditions.

Alternatively, the compounds of the invention may be synthesized according to Scheme 7 below:

Scheme 7: Exemplary synthetic route useful for the preparation of compounds of the invention

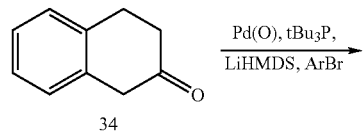

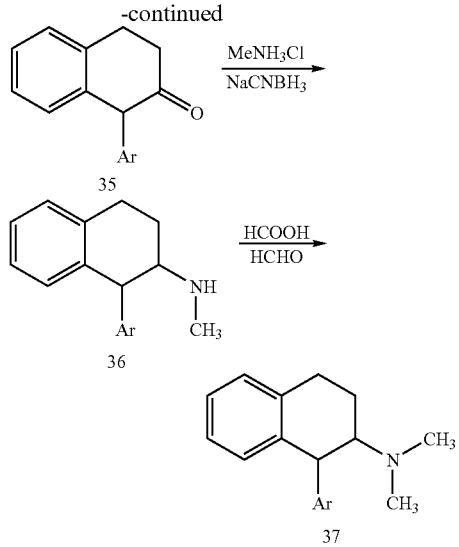

Referring to Scheme 7, beta-tetralone 34 is condensed with the aryl bromide. The substituted beta-tetralone so produced may be treated with ammonium chloride or methylamine hydrochloride under reductive-amination conditions to give the amine 36. The dimethylamine 37 is prepared by methylation of the methylamine using Eschweiler-Clark conditions.

Alternatively, the compounds of the invention may be synthesized according to Scheme 8 below:

Scheme 8: Exemplary synthetic procedures useful for the preparation of compounds of the invention

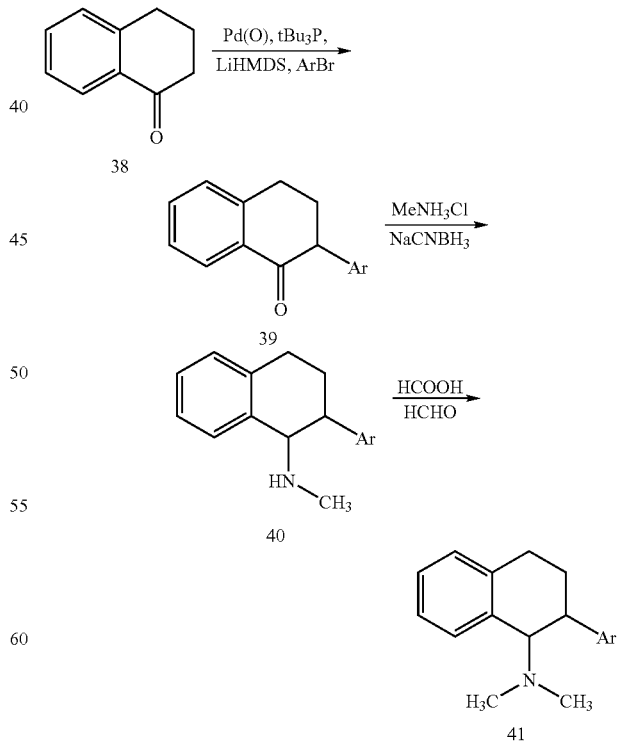

Referring to Scheme 8, alpha-tetralone 38 is condensed with the aryl bromide. The substituted alpha-tetralone so produced may be treated with ammonium chloride or methylamine hydrochloride under reductive-amination conditions to give the amine 40. The dimethylamine 41 is prepared by methylation of the methylamine using Eschweiler-Clark conditions.

In another embodiment, the compounds of the invention may be synthesized according to Scheme 9 below:

Scheme 9: Exemplary synthetic route useful for the preparation of compounds of the invention

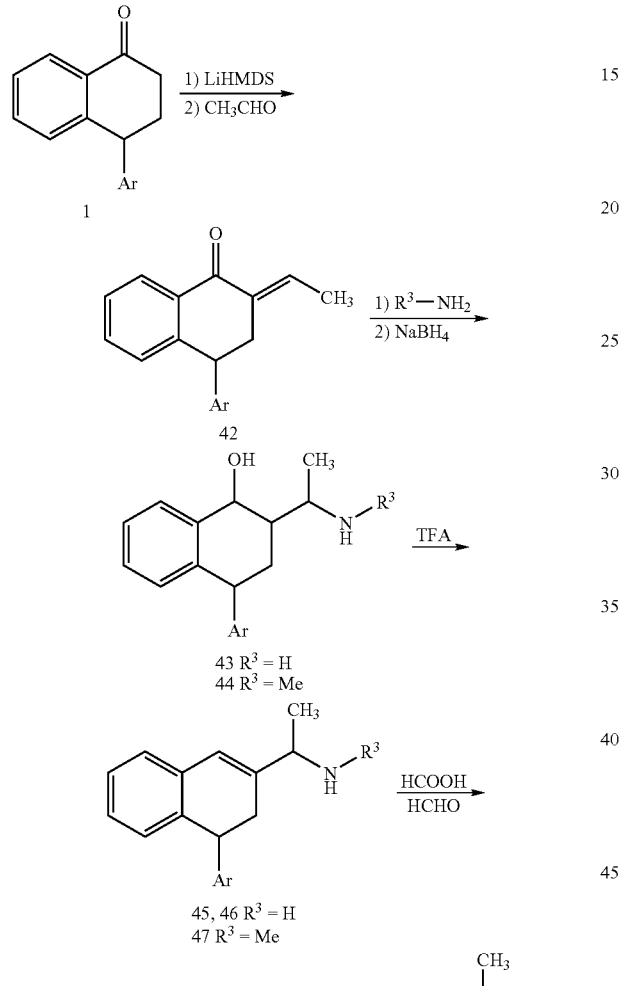

Alternatively, the compounds of the invention may be synthesized according to Scheme 10 below:

Scheme 10: Exemplary synthetic route useful for the preparation of compounds of the invention

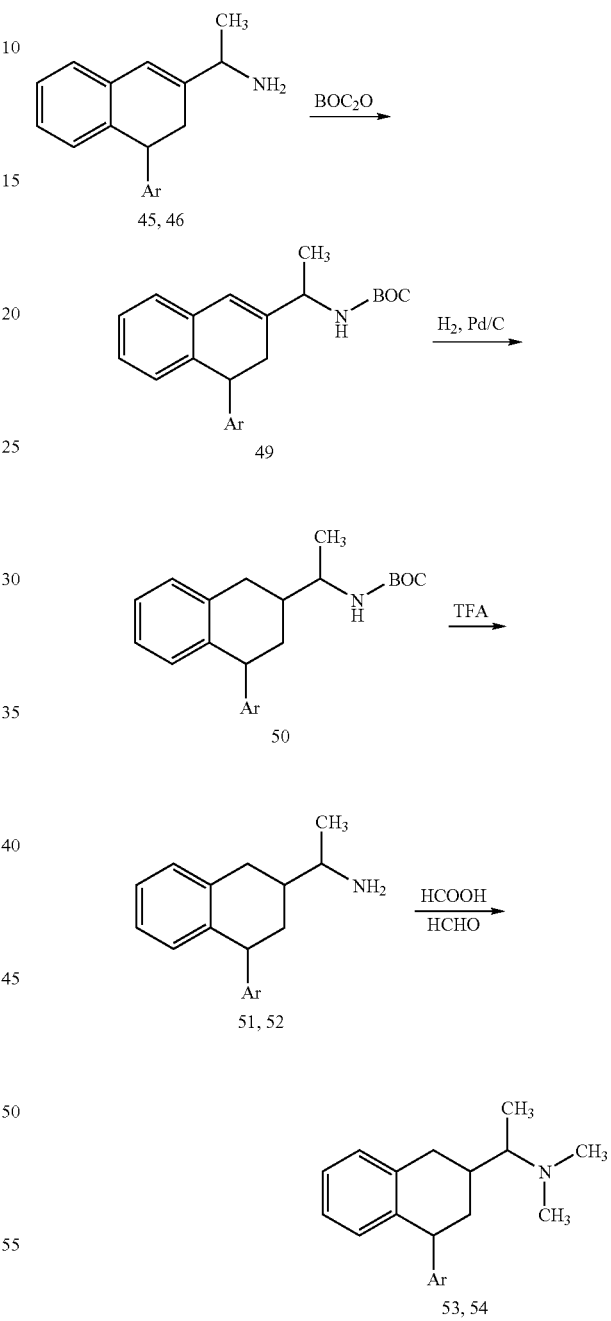

Referring to Scheme 9, the alpha-tetralone analog 1 is condensed with acetaldehyde to produce the substituted alpha-tetralone 42, which may be treated with ammonium chloride or methylamine hydrochloride and subsequently reduced to give the amino-alcohols 43 and 44. The benzylic alcohol can be eliminated to form the unsaturated amines 45/46 and 47. The dimethylamine 48 is prepared by methylation of the methylamine using Eschweiler-Clark conditions.

Referring to Scheme 10, the primary amines 45 and 46 are condensed with Boc-anhydride. The double bond is then hydrogenated and the Boc group is removed with TFA to give the saturated amines 51 and 52. The dimethylamines 53 and 54 are prepared by methylation of the methylamine using Eschweiler-Clark conditions.

Alternatively, the compounds of the invention may be synthesized according to Scheme 11 below:

Scheme 11: Exemplary ssynthetic routes useful for the preparation of compounds of the invention

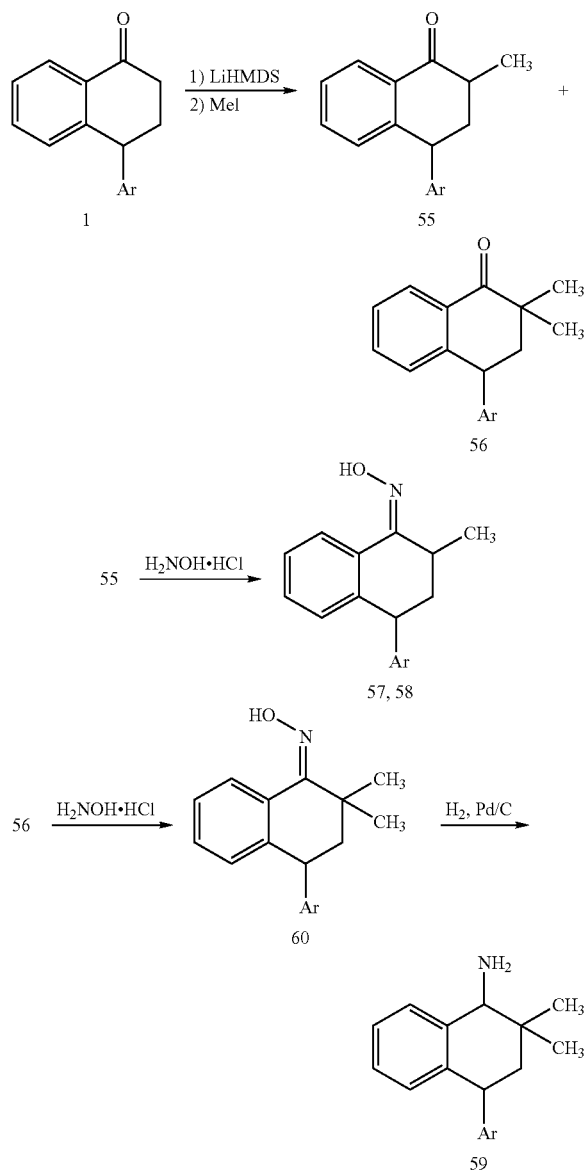

Referring to Scheme 11, the alpha-tetralone 1 is deprotonated and reacted with methyl iodide to give both the mono- and di-methylated ketones 55 and 56, which can be separated. The mono-methylated ketone 55 is condensed with hydroxylamine to give the oxime. Diastereomeric separation gave the oximes 57 (cis-diastereomer) and 58 (trans-diastereomer). The di-methylated ketone 56 is treated in a similar manner to give the oxime 60. The oxime can be further reduced with hydrogen to give the amine 59.

D. Pharmaceutical Compositions

In another aspect, the present invention provides pharmaceutical compositions including a compound of the invention (e.g., a compound of Formulae (I) to (IV)) or a pharmaceutically acceptable salt or solvate thereof and one or more pharmaceutically acceptable carrier, additive, vehicle, diluent or combinations thereof.

As described in detail below, the pharmaceutical compositions of the present invention may be specially formulated for administration in solid or liquid form, including those adapted for oral administration, e.g., tablets, drenches (aqueous or non-aqueous solutions or suspensions), parenteral administration (including intravenous and intramuscular), or epidural injection as, for example, a sterile solution or suspension, or sustained release formulation. The pharmaceutical compositions of the present invention may also be specifically formulated for administration transdermally.

The pharmaceutical compositions of the invention may be administered orally, parenterally, subcutaneously, transdermally, nasally, or by anal suppository. The pharmaceutical compositions of the invention may also be administered using controlled delivery devices.

Formulations of the present invention include those suitable for oral and parenteral administration, particularly intramuscular, intravenous and subcutaneous administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect, without being toxic to the patient. Generally, out of one hundred percent, this amount will range from about 1 percent to about ninety-nine percent of active ingredient.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, caplets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a compound of the present invention as an active ingredient. A compound of the present invention may also be administered as a bolus, electuary or paste.

In solid dosage forms of the invention for oral administration (capsules, tablets, caplets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium sterate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue. Pharmaceutical compositions or unit dosage forms of the present invention in the form of prolonged-action tablets may comprise compressed tablets formulated to release the drug substance in a manner to provide medication over a period of time. There are a number of tablet types that include delayed-action tablets in which the release of the drug substance is prevented for an interval of time after administration or until certain physiological conditions exist. Repeat action tablets may be formed that periodically release a complete dose of the drug substance to the gastrointestinal fluids. Also, extended release tablets that continuously release increments of the contained drug substance to the gastrointestinal fluids may be formed.

Compounds of the invention can be also administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the compounds of this invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Compounds of the present invention may also be formulated as transdermal, topical, and mucosal dosage forms, which forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences,* 16th and 18th eds., Mack Publishing, Easton Pa. (1980 & 1990); and *Introduction to Pharmaceutical Dosage Forms,* 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers can be used to assist in delivering the active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

When the compounds of the present invention are administered as pharmaceuticals, to humans and animals, they can be given per se or as a pharmaceutical composition containing, for example, 0.1 to 99.5% of active ingredient in combination with a pharmaceutically acceptable carrier.

The preparations of the present invention may be given orally and parenterally. They are of course given in forms suitable for each administration route. For example, they are administered in tablets or capsule form, by injection, and by intravenous administration. In one embodiment, oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.005 mg per kilogram to about 5 mg per kilogram of body weight per day.

The terms "treatment" or "treating" is intended to encompass therapy, preventing (prophylaxis), preventing relapse, and amelioration of acute symptoms. Note that "treating" refers to either or both of the amelioration of symptoms and the resolution of the underlying condition. In many of the conditions of the invention, the administration of a compound or composition of the invention may act not directly on the disease state, but rather on some pernicious symptom, and the improvement of that symptom leads to a general and desirable amelioration of the disease state The patient receiving this treatment is any animal in need, including primates, in particular humans, and other mammals such as equines, cattle, swine and sheep; and poultry and pets in general.

The compounds and pharmaceutical compositions of the invention can be administered in conjunction with other pharmaceutical agents, for instance antimicrobial agents, such as penicillins, cephalosporins, aminoglycosides and glycopeptides. Conjunctive therapy thus includes sequential, simultaneous and separate administration of the active compound in a way that the therapeutic effects of the first administered agent have not entirely disappeared when the subsequent agent is administered.

IV. Methods

A. Treatment of CNS Disorders

In another aspect, the present invention provides a method of treating a central nervous system disorder. The method includes administering to a subject in need thereof a therapeutically effective amount of a compound or composition of the invention, e.g., a compound according to Formulae (I) to (IV), or a pharmaceutically acceptable salt or solvate thereof. This method of treatment is particularly suitable for humans and other mammals.

In an exemplary embodiment, the central nervous system disorder is a member selected from the group consisting of depression (e.g., major depressive disorder, bipolar disorder), fibromyalgia, pain (e.g., neuropathic pain), sleep related disorders (e.g., sleep apnea, insomnia, narcolepsy, cataplexy) including those sleep disorders, which are produced by psychiatric conditions, chronic fatigue syndrom, attention deficit disorder (ADD), attention deficit hyperactivity disorder (ADHD), restless leg syndrome, schizophrenia, anxieties (e.g. general anxiety disorder, social anxiety discorder, panic), obsessive compulsive disorder, posttraumatic stress disorder, seasonal affective disorder (SAD), premenstrual dysphoria, post-menopausal vasomotor symptoms (e.g., hot flashes, night sweats), and neurodegenerative disease (e.g., Parkinson's disease, Alzheimer's disease and amyotrophic lateral sclerosis), manic conditions, dysthymic disorder, and cyclothymic disorder.

Central nervous system disorder includes cerebral function disorders, including without limitation, senile dementia, Alzheimer's type dementia, cognition, memory loss, amnesia/amnestic syndrome, epilepsy, disturbances of consciousness, coma, lowering of attention, speech disorders, Lennox syndrome, autism, and hyperkinetic syndrome.

Neuropathic pain includes without limitation post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use).

Other exemplary diseases and conditions that may be treated using the methods of the invention include obesity; migraine or migraine headache; urinary incontinence, including without limitation involuntary voiding of urine, dribbling or leakage of urine, stress urinary incontinence (SUI), urge incontinence, urinary exertional incontinence, reflex incontinence, passive incontinence, and overflow incontinence; as well as sexual dysfunction, in men or women, including without limitation sexual dysfunction caused by psychological and/or physiological factors, erectile dysfunction, premature ejaculation , vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

B. Inhibition of Monoamine Reuptake

In another aspect, the invention provides a method of inhibiting reuptake of one or more monoamine from the synaptic cleft. The method includes administering to a subject in need thereof a therapeutically effective amount of a compound or composition of the invention, e.g., a compound according to Formulae (I) to (IV), or a pharmaceutically acceptable salt or solvate therof. This method of treatment is particularly suitable for humans and other mammals. In an exemplary embodiment, the monoamine is dopamine, serotonin, norepinephrine or combinations thereof.

C. Modulation of Monoamine Transporters

In yet another aspect, the invention provides a method of modulating one or more monoamine transporter. The method includes administering to a subject in need thereof a therapeutically effective amount of a compound or composition of the invention, e.g., a compound according to Formulae (I) to (V), or a pharmaceutically acceptable salt or solvate therof. This method of treatment is particularly suitable for humans and other mammals. In an exemplary embodiment, the monoamine transporter is dopamine transporter (DAT), serotonin transporter (SERT) or norepinephrine transporter (NET).

EXAMPLES

General: Determination of Absolute Stereochemistry

In this application, relative stereochemistries are used unless otherwise indicated. Assignments of relative stereochemistries were made using NMR techniques (determination of cis- and trans-configurations, optionally using literature reports for similar compounds). Absolute stereochemistries of selected compounds were determined by synthesis of key intermediates from commercially-available (S)-α-tetralone as outlined in Scheme 12, below. Correlations were made using chiral HPLC analyses. For example, spiking authentic samples into enantiomeric and/or diastereomeric mixtures allowed for a correlation of retention times and structures.

Scheme 12: Synthesis of authentic samples from commercial (S)-α-tetralone

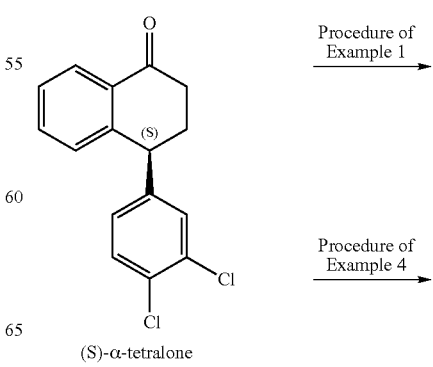

(S)-α-tetralone

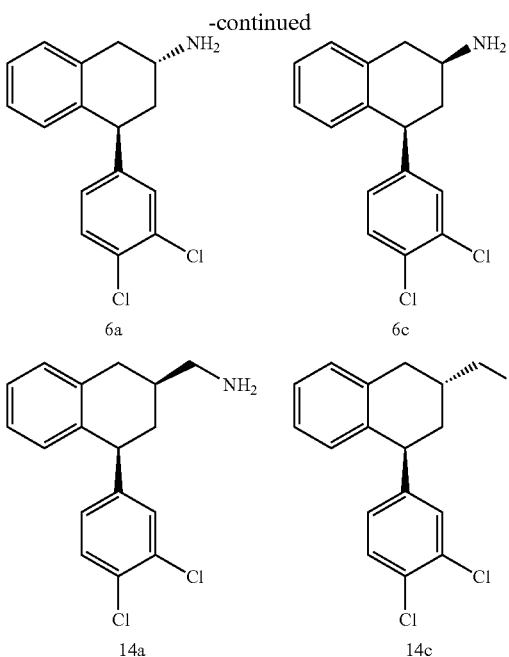

6a, 6c, 14a, 14c

Example 1

Synthesis of [4-(3,4-dichlorophenyl)-1,2,3,4-tetrahydro-naphthalen-2-yl]-amine (6a-d)

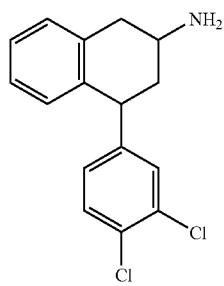

1.1 Synthesis of 4-(3,4-dichlorophenyl)-1,2,3,4-tetrahydro-naphthalen-1-ol (2)

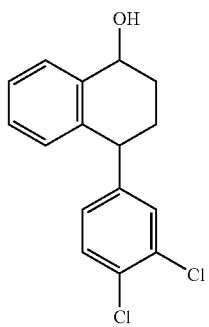

To a stirring mixture of alpha-tetralone 4-(3,4-dichlorophenyl)-3,4-dihydro-2H-naphthalen-1-one 1 (53 g, 182 mmol) in methanol (400 mL) was added sodium borohydride (12 g) in portions. The mixture was stirred at ambient temperature for three hours. Water was added and the volatile components were removed in vacuo. The aqueous remainder was extracted with ethyl acetate. The organic phase was separated, washed with water, dried ($Na_2SO_4$), and evaporated to dryness to yield the crude alcohol (53 g). TLC $R_f$ (25 EA/hex)=0.25, 0.18. $^1$H NMR ($CDCl_3$, δ): 7.39 (d, J=8.0 Hz, 1H), 7.3-7.2 (m, 4H), 7.0-6.9 (m, 2H), 4.42 (t, J=6.4 Hz, 1 H), 3.62 (q, J=20 Hz, 2H), 2.9 (m, 2H). $^{13}$C NMR ($CDCl_3$, δ, mult): 146.9(0), 146.8(0), 139.6 (0), 138.9(0), 138.3(0), 137.7(0), 132.3(0), 132.2(1), 130.6(1), 130.5(1), 130.3(1), 130.2(1), 129.8(1), 129.7(1), 129.0(1), 128.2(1), 128.1(1), 128.1(1), 128.0(1), 127.9(1), 127.1(1), 127.0(1), 68.1(1), 67.7(1), 45.0 (1), 44.4(1), 30.0(2), 29.9(2), 28.9(2), 28.1(2).

1.2. Synthesis of 1-(3,4-dichlorophenyl)-1,2-dihydronaphthalene (3)

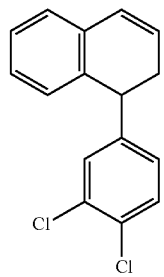

To a solution of the crude alcohol 2 (53 g) in toluene (500 mL) was added silica gel coated with sulfuric acid (3%, 14 g). The mixture was heated to 100° C. and monitored by TLC (prod $R_f$ (25 EA/hex)=0.58). After three hours, the mixture was filtered. The organic phase was washed with water and sodium bicarbonate solution, dried ($Na_2SO_4$), and evaporated to give the alkene 3 (42 g, 84%) as a pale-brown solid. TLC $R_f$ (25 EA/hex)=0.58. GC-MS $R_t$=13.55 min, m/z=274 (M+). $^1$H NMR ($CDCl_3$, δ): 7.4-6.7 (m, 7H), 6.54 (d, J=9.6 Hz, 1H), 6.0 (m, 1H), 4.08 (t, J=8.0 Hz, 1H), 2.7 (m, 1H), 2.5 (m, 1H). $^{13}$C NMR ($CDCl_3$, δ, mult): 143.6, 136.3, 133.8, 132.2, 130.2, 130.2, 128.1, 127.7, 127.2, 126.4, 129.7, 127.4, 42.8 (1), 31.6(2).

1.3. Synthesis of 4-(3,4-dichlorophenyl)-3,4-dihydro-1H-naphthalen-2-one (5)

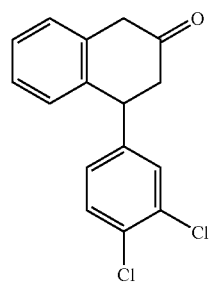

To a stirring solution of the alkene 3 (3 g, 10.8 mmol) in acetone (40 mL) was added NMO (2 g, 1.6 eq) and water (10 mL). After the NMO dissolved, osmium tetroxide (1.3 mL, 0.1 M in toluene, 5 mol %) was added and the solution was stirred at ambient temperature for 40 minutes. Sodium bisulfate (10 mL, 10% solution in water) was added and the mixture was stirred for an additional 30 minutes. After this time, the solvent was removed in vacuo and the resultant oily solid was partitioned between MTBE and, sequentially, water and brine. The organic solvent was evaporated to yield the crude diol (3.6 g) as a brown glass. TLC $R_f$ (50 EA/hex)=0.14. The crude diol (4) was sufficiently pure for the next step, and could be confirmed by the three diagnostic peaks that are discernable in the $^1$H NMR (4.8, 4.4, 4.2 ppm).

The diol 4 was dissolved in toluene (200 mL). Tosic acid (600 mg, 30 mol %) was added and the solution was heated to reflux in a Dean-Stark water separator until the diol was consumed. After three hours, the reaction mixture was cooled and most of the toluene was removed. The remaining liquid was partitioned between MTBE and, sequentially, 10% aqueous KOH, water, and brine. The organic layer was evaporated and the crude green oil was separated on silica gel to give the beta-tetralone 5 (1.46 g, 46%) as a pale-yellow oil. TLC $R_f$ (50 EA/hex)=0.39. GC-MS $R_t$=13.54 min, m/z=290 (M+). $^1$H NMR (CDCl$_3$, δ): 7.39 (d, J=8.0 Hz, 1H), 7.3-7.2 (m, 4H), 7.0-6.9 (m, 2H), 4.42 (t, J=6.4 Hz, 1H), 3.62 (q, J=20 Hz, 2H), 2.9 (m, 2H). $^{13}$C NMR (CDCl$_3$, δ, mult): 208.2 (0), 141.7(0), 137.7(0), 133.0(0), 132.8(0), 131.0(0), 130.6(1), 129.8(1), 128.7(1), 127.8(1), 127.5(1), 127.1(1), 45.4(2), 44.5(2), 43.8 (1).

1.4. Synthesis of [4-(3,4-dichlorophenyl)-1,2,3,4-tetrahydro-naphthalen-2-yl]-amine (6a-d)

Ammonium chloride (643 mg, 10 eq) was dissolved in methanol (24 mL) by heating to 50° C. After it cooled, a solution of ketone 5 (350 mg, 1.202 mmol) in THF (18 mL) was added followed by sodium cyanoborohydride 6.0 mL, 5 eq). The mixture was heated in a 50° C. oil bath overnight. The reaction was then cooled, quenched with aqueous sodium bicarbonate, and extracted with MTBE. The combined organic layer was washed with brine and evaporated to give a brown-green oil. The oil was separated on silica gel to give the primary amine 6 (145 mg, 41%) as a pale-green oil.

As isolated, the amine was a mixture of four stereoisomers which were separable using chiral columns. First, the mixture was separated on a Chiracel OD column (90:10:0.1 Hex/IPA/DEA) to give three fractions. Symchiral trans (Compound 6a at 11.9 min, racemic cis at 14.7 min, and symchiral trans (Compound 6b) at 22.3 min. The racemic cis was then resubmitted to the Chiracel AD column 95:2:3:0.1 Hex/MeOH/EtOH/DEA) to give the symchiral cis (Compound 6c) at 11.1 min and symchiral cis (Compound 6d) at 13.9 min. Retention times are summarized in Table 1, below.

TABLE 1

| Retention times for each diastereomer [min] | | | | |
|---|---|---|---|---|
| | 6a Trans | 6c Cis | 6d Cis | 6b Trans |
| HPLC $R_t$ (Chiracel OD, 90:10:0.1 Hex/IPA/DEA) | 11.9 | 14.7 | 14.7 | 22.3 |
| HPLC $R_t$ (Chiracel AD, 95:2:3:0.1 Hex/MeOH/EtOH/DEA) | | 11.1 | 13.9 | |

Absolute stereochemistries for compounds 6a-d were determined using a combination of NMR techniques (determination of cis- and trans-configurations) and chiral HPLC analyses using authentic samples, which were prepared from commercial (S)-alpha-tetralone as described above (also compare "General Procedures"). The resulting structures indicating absolute stereochemistries are shown below:

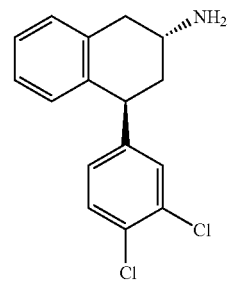

6a

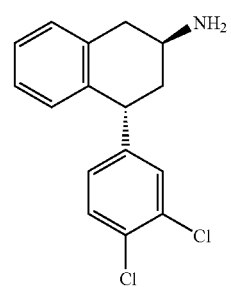

6b

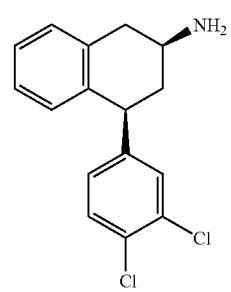

6c

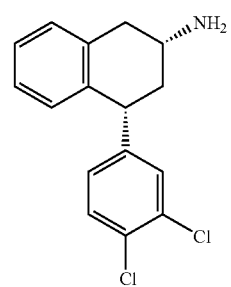

6d

Trans-isomers 6a and 6b: GC-MS $R_t$=13.52 min, m/z=291 (M+). $^1$H NMR (CDCl$_3$, δ): 7.4-6.8 (m, 7H), 4.32 (t, J=5.4 Hz, 1H), 3.3 (m, 1H), 3.17 (dd, J=4.9, 16.3 Hz, 1H), 2.7 (m, 3H), 2.1 (m, 2H). $^{13}$C NMR (CDCl$_3$, δ, mult): 160.3(0), 147.2(0), 136.0(0), 135,2(0), 132.3(0), 130.5(1), 130.1(1), 130.0(1), 129.5(1), 128.0(1), 126.9(1), 126.5(1), 43.2(1), 42.9(1), 40.2(2), 38.2(2).

Cis-isomers 6c and 6d: GC-MS $R_t$=13.61min, m/z=291 (M+). $^1$H NMR (CDCl$_3$, δ): 7.4-6.7 (m, 7H), 4.11 (dd, J=5.5, 12.1 Hz, 1H), 3.26 (ddt, J=3.1, 4.9, 11.3 Hz, 1H), 3.07 (ddd, 2.2, 4.8, 15.9 Hz, 1H), 2.2 (m, 1H), 1.6 (m, 3H). $^{13}$C NMR (CDCl$_3$, δ, mult): 146.7(0), 137.8(0), 135.9(0), 132.4(0), 130.6(1), 130.5(1), 129.1(0), 129.1(1), 128.1 (1), 126.5(1), 126.2(1), 130.2(1), 47.6(1), 46.0(1), 44.4(2), 40.2(2).

Example 2

Synthesis of 4-(3,4-dichlorophenyl)-N-methyl-1,2,3,4-tetrahydronaphthalen-2-amine (7a-d)

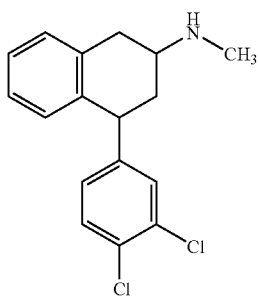

To a solution of ketone 5 (350 mg, 1.202 mmol) in THF (18 mL) and methanol (24 mL) was added methylamine hydrochloride (980 mg, 10 eq). After the solid dissolved, sodium cyanoborohydride (6.0 mL, 1 M in THF, 5 eq) was added in one portion. The mixture was heated in a 50° C. oil bath overnight before being quenched with aqueous sodium bicarbonate and extracted with MTBE. The combined organic layer was washed with brine and evaporated to give a brown-green oil. The oil was dissolved in MTBE and extracted into 10% aqueous hydrochloric acid. The aqueous layer was basicified with KOH and extracted with MTBE. The volatile components were removed in vacuo and the crude green oil was separated on silica gel to give the methylamine (0.20 g, 54%) as a pale-green oil.

As isolated, the amine was a mixture of four stereoisomers which were separable on chiral columns. First, the mixture was separated on a Chiracel OD column (98:2:0.1 Hex/IPA/DEA) to give three fractions. Symchiral trans (Compound 7a) at 12.4 min, racemic cis at 15.8 and 17.6 min, and symchiral trans (Compound 7b) at 29.7 min. The racemic cis was then resubmitted to a Chiracel AD column (98:2:0.1 Hex/IPA/DEA) to give the symchiral cis (Compound 7c) at 20.2 min and symchiral cis (SME Compound 7d) at 27.7 min. Retention times are summarized in Table 2, below.

TABLE 2

| Retention times for each diastereomer [min] | | | | |
|---|---|---|---|---|
| | 7a Trans | 7c Cis | 7d Cis | 7b Trans |
| HPLC $R_t$ (Chiracel OD, 98:2:0.1 Hex/IPA/DEA) | 12.4 | 15.8 | 17.6 | 29.7 |
| HPLC $R_t$ (Chiracel AD, 98:2:0.1 Hex/IPA/DEA) | | 20.2 | 27.7 | |

Absolute stereochemistries of compounds 7a-d were determined using a combination of NMR techniques (determination of cis- and trans-configurations) and chiral HPLC analyses using authentic samples, which were prepared from commercial (S)-alpha-tetralone as described above (also compare "General Procedures"). The resulting structures indicating absolute stereochemistries are shown below:

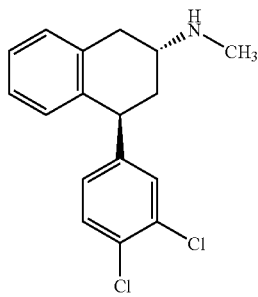

7a

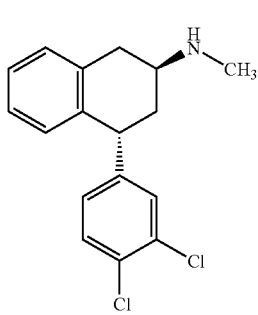

7b

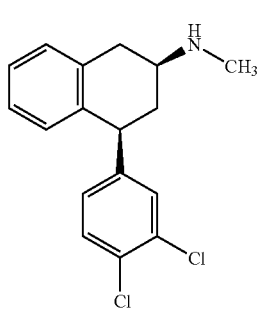

7c

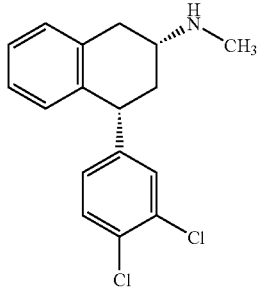

7d

Trans-isomers 7a and 7b: LC-MS $R_t$=8.3 min, m/z=306 (M+1). GC-MS $R_t$=13.64 min, m/z=305 (M+). $^1$H NMR (CDCl$_3$, δ): 7.4-6.8 (m, 7H), 4.26 (t, J=5.8 Hz, 1H), 3.15 (dd, J=4.6, 16.2 Hz, IH), 2.9 (m, 1H), 2.66 (dd, J=7.8, 16.2 Hz, 1H), 2.43 (s, 3H), 2.0 (m, 2H), 1.3 (bs, 1 H). $^{13}$C NMR (CDCl$_3$, δ, mult): 147.5(0), 136.8(0), 135.6(0), 132.2(0), 130.6(1), 130.1(1), 129.9(0), 129.8(1) 129.5(1), 128.1(1), 126.7(1), 126.2(1), 51.1(1), 42.5(1), 37.8(2), 36.0(2), 33.7 (3).

Cis-isomers 7c and 7d: LC-MS $R_t$=8.5 min, m/z=306 (M+1). GC-MS $R_t$=13.82 min, m/z=305 (M+). $^1$H NMR (CDCl$_3$, δ): 7.4-6.7 (m, 7H), 4.08 (dd, J=5.4, 12.2 Hz), 3.12 (ddd, J=2.2, 4.7, 15.7 Hz, 1 H), 2.93 (ddt, J=2.9, 4.8, 11.2 Hz, 1H), 2.70 (dd, J=11.1, 15.7 Hz, 1H), 2,52 (s, 3H), 2.3 (m, IH). $^{13}$C NMR (CDCl$_3$, δ, mult): 146.8(0), 138.2(0), 135.8(0), 132.4(0), 130.6(1), 130.5(1), 130.2(0), 129.2(1), 129.0(1), 128.1(1), 126.4(1), 126.1(1), 55.5(1), 45.8(1), 40.5(2), 37.4(2), 33.6(3).

Example 3

Synthesis of [4-(3,4-dichlorophenyl)-1,2,3,4-tetrahydro-naphthalen-2-yl]-dimethylamine (8a-d)

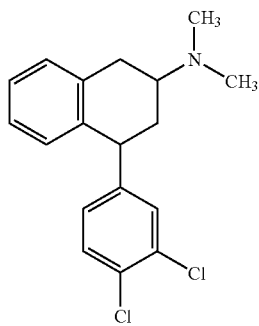

The respective methylamine 7 (e.g., 28.4 mg, 0.0927 mmol) was dissolved in 96% formic acid (0.5 mL) and 37% aqueous formaldehyde (0.5 mL) and heated at 100° C. for two hours. After cooling, the solution was basicified (aq KOH) and extracted with MTBE. The organic phase was dried with sodium sulfate, filtered, and evaporated to give the dimethylamine (e.g., 27.1 mg, 93%) as a clear oil.

Absolute stereochemistries for compounds 8a-d were determined and are shown below:

8a
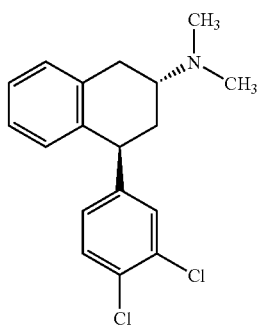

8b
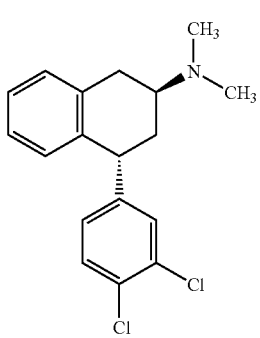

8c
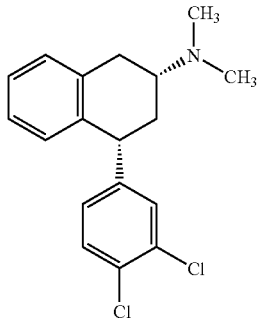

8d
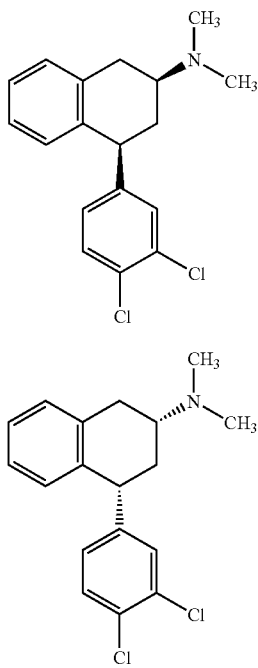

Trans-isomers 8a and 8b: LC-MS $R_t$=9.0 min, m/z=320 (M+1). $^1$H NMR (CDCl$_3$, δ): 7.4-6.8 (m, 7H), 4.32 (t, J=5.4 Hz, 1 H), 3.02 (dd, J=4.8, 16.3 Hz, 1H), 2.84 (dd, J=9.3, 16.3 Hz, 1H), 2.6 (m, 1H), 2.27 (s, 6H), 2.1 (m, 2H). $^{13}$CNMR (CDCl$_3$, δ, mult): 147.3(0), 136.6(0), 136.3(0), 132.1(0), 130.5(1), 130.0(1), 129.8(0), 129.5(1), 128.1 (1), 126.7(1), 126.2(1), 129.9(1), 56.0(1), 43.3(1), 41.9(3), 34.9(2), 32.1 (2).

Cis-isomers 8c and 8d: LC-MS $R_t$=9.1 min, m/z=320 (M+1). $^1$H NMR (CDCl$_3$, δ): 7.4-6.7 (m, 7H), 4.07 (dd, J=5.3, 12.2 Hz, 1H), 3.1-2.9 (m, 2H), 280 (ddt, J=2.5, 4.9, 11.4 Hz, 1H), 2.37 (s, 6H), 2.3 (m, 1H), 1.65 (q, J=12.2 Hz, 1H). $^{13}$C NMR (CDCl$_3$, δ, mult): 146.9(0), 138.0(0), 136.3(0), 132.4 (0), 130.6(1), 130.5(1), 130.3(0), 129.5(1), 129.0(1), 128.1 (1), 126.4(1), 126.1(1), 60.3(1), 46.4(1), 41.4(3), 36.8(2), 32.8(2).

Example 4

Synthesis of (4-(3,4-dichlorophenyl)-1,2,3,4-tetrahydronaphthalen-2-yl)methanamine (14a-d)

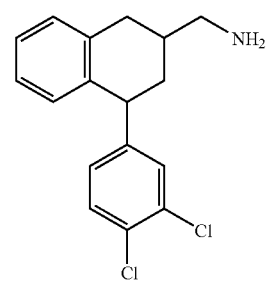

4.1. Synthesis of 4-(3,4-dichlorophenyl)-1-oxo-1,2,3,4-tetrahydro-naphthalene-2-carboxylic acid ethyl ester (9)

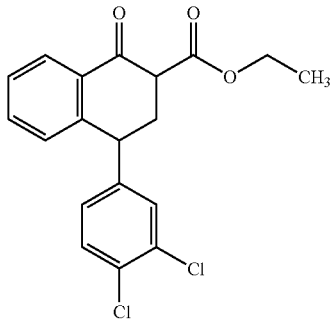

To a stirred suspension of NaH (60% dispersion in mineral oil, 1.69 g, 42 mmol) in THF (80 ml) under $N_2$ was added dropwise diethylcarbonate (4.85 ml, 40 mmol) at room temperature, followed by 4-(3',4'-dichlorophenyl)-3,4-dihydro-1-(2H)-naphthalone 1 (5.82 g, 20 mmol) in THF (20 ml). The mixture was refluxed for 48 hours, then cooled to 0° C. Acetic acid (10 ml) was added dropwise, and the mixture was extracted with $Et_2O$. The $Et_2O$ extracts were washed with saturated $NaHCO_3$ solution, brine, dried over $MgSO_4$, and evaporated. The residue was purified by chromatography, CombiFlash silica gel column (hexane:$CH_2Cl_2$=50:50) to give Compound 9 as a clear oil (5.81 g, 80%). $^1$H NMR ($CDCl_3$) δ 1.30 (t, J=7.2 Hz, 3H), 2.77 (dd, J=16 Hz, 9.6 Hz, 1H), 2.91 (dd, J=15.6 Hz, 6.4 Hz, 1H), 4.10 (dd, J=12 Hz, 6.4 Hz, 1H), 4.19-4.30 (m, 2H), 6.87 (d, J=6.8 Hz, 1H), 7.00 (dd, J=8.4 Hz, 2.0 Hz, 1H), 7.27-7.36 (m, 5H), 7.89 (dd, J=8.4 Hz, 2.0 Hz, 1H), 12.50 (s, 1H). $^{13}$C NMR ($CDCl_3$) δ 14.5, 29.1, 43.4, 61.0, 95.6, 125.0, 127.6, 127.9, 128.1, 130.2, 130.6, 130.7, 131.0, 131.3, 132.8, 140.4, 143.9, 164.8, 172.6.

4.2. Synthesis of 4-(3,4-dichlorophenyl)-1,2,3,4-tetrahydro-naphthalene-2-carboxylic acid ethyl ester (10)

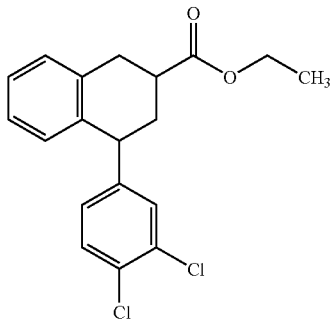

To a solution of 9 (2.81 g, 7.74 mmol) in TFA (30 ml) was added dropwise $Et_3SiH$ (7.42 ml, 46.44 mmol) at 0° C. Stirring was continued at 0° C. for 2 hours. Then, the solvent was evaporated, and the residue was purified by chromatography, CombiFlash silica gel column, hexane/$CH_2Cl_2$, $CH_2Cl_2$ from 0% to 50%, to give compound 10 as a clear oil (mixture of cis and trans diastereomers, 2.63 g, 97%). $^1$H NMR ($CDCl_3$) δ 1.18-1.34 (m, 3H), 1.88 (dd, J=25.2 Hz, 12.4 Hz) and 2.14-2.19 (m, total 1H), 2.25-2.33 (m) and 2.43-2.55 (m, total 1H), 2.67-2.74 (m) and 2.82-2.92 (m, total 1H), 3.00-3.18 (m, 2H), 4.08-4.29 (m, 3H), 6.72-7.42 (m, 7H).

4.3. Synthesis of [4-(3,4-dichlorophenyl)-1,2,3,4-tetrahydro-naphthalen-2-yl]-methanol (11)

A solution of 10 (2.55 g, 7.3 mmol) in THF (40 ml) was added dropwise to a stirring mixture of $LiAlH_4$ (0.304 g, 8.0 mmol) in THF (20 ml) at 0° C. The resulting suspension was stirred at room temperature for 3 hours, then, the mixture was cooled to 0° C., and water (0.15 ml) was added dropwise to destroy the excess hydride. The mixture was filtered, and the solvent was evaporated in vacuo to give colorless oil. The residue was purified by chromatography, CombiFlash silica gel column, MeOH/$CH_2Cl_2$, MeOH from 0% to 3%, to give 11 as a clear oil (mixture of cis and trans diastereomers, 1.80 g, 80%). $^1$H NMR ($CDCl_3$) δ 1.31-1.54 (m, 1H), 1.92-1.98 (m, 2H), 2.10-2.26 (m, 1H), 2.54-2.71 (m, 1H), 2.92-3.03 (m, 1H), 3.53-3.75 (m, 2H), 4.07 (dd, J=12 Hz, 5.2 Hz) and 4.25 (t, J=3.6 Hz, total 1 H), 6.72-7.38 (m, 7H). $^{13}$C NMR ($CDCl_3$) δ 32.0, 32.5, 33.4, 34.6, 37.5, 37.6, 43.3, 46.3, 67.5, 67.9, 126.3, 126.4, 126.6, 127.0, 128.4, 128.5, 129.5, 129.7, 130.2, 130.5, 130.7, 130.9, 132.4, 132.7, 136.7, 136.9, 138.8, 147.5, 147.9.

4.4. Synthesis of 3-bromomethyl-1-(3,4-dichlorophenyl)-1,2,3,4-tetrahydronaphthalene (12)

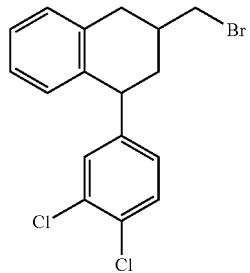

To a solution of compound 11 (1.25 g, 4.07 mmol) and $CBr_4$ (2.33 G, 7.04 mmol) in $CH_2Cl_2$ (15 ml) was added $Ph_3P$ (1.82 g, 6.92 mmol) in $CH_2Cl_2$ (15 ml) at 0° C. The reaction was allowed to warm to room temperature overnight, was then poured into water ((40 ml), extracted with $CH_2Cl_2$ (75 ml), dried over $Na_2SO_4$, and the solvent was evaporated. The residue was purified by chromatography, CombiFlash silica gel column, EtOAC hexanes, EtOAc from 0% to 15%, to give compound 12 as a clear oil (mixture of cis and trans diastereomers, 1.50 g, 99%). $^1$H NMR. ($CDCl_3$) δ 1.52-1.62 (m) and 1.97-2.15 (m, total 2H), 2.25-2.30 (m, 1H), 2.64-2.77 (m, 1H), 3.02-3.12 (m, 1H), 3.34-3.47 (m, 2H), 4.08 (dd, J=12 Hz, 5.2 Hz) and 4.26 (t, J=3.6 Hz, total 1H), 6.72-7.39 (m, 7H). 13C NMR ($CDCl_3$) δ 31.8, 34.6, 35.6, 36.8, 37.2, 39.2, 39.3, 39.4, 43.3, 46.4, 126.5, 126.8, 126.9, 127.2, 128.3, 128.4, 128.6, 129.0, 129.4, 129.5, 129.7, 130.2, 130.5, 130.7, 130.9, 132.5, 132.8, 136.1, 136.3, 138.3, 147.0, 147.5.

4.5. Synthesis of 3-azidomethyl-1-(3,4-dichlorophenyl)-1,2,3,4-tetrahydronaphthalene (13)

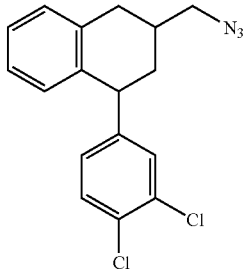

A mixture of compound 12 (0.293 g, 0.79 mmol) and sodium azide (0.154 g, 2.38 mmol) in DMF (5 ml) was stirred at 60° C. for 24 hours. The reaction mixture was filtered and evaporated in vacuo. The residue was partitioned between water and EtOAc. The organic layer was separated, washed with water, dried over $Na_2SO_4$, and evaporated to give compound 13 as a pale yellow oil (mixture of cis and trans diastereomers, ratio=1:1.1, 0.18 g, 68%). The diastereomers were separated using a preparative chiral HPLC procedure (ChiralPak OD column; hexanes:MeOH=98:2; μ=8 ml/min; and λ=225 nm) to give compounds 13a-13d (retention times: 9.8 min, 12.0 min, 14.5 min and 20.1 min, respectively).

Cis-isomers 13a and 13b: $^1$H NMR ($CDCl_3$) δ 1.92-2.09 (m, 3H), 2.61 (dd, J=16.4 Hz, 9.8 Hz, 1H), 3.00 (dd, J=16.8 Hz, 4.8 Hz, 1H), 3.29 (d, J=6.0 Hz, 2H), 4.25 (t, J=4.8 Hz, 1H), 6.81-6.92 (m, 2H), 7.08-7.15 (m, 2H), 7.18-7.21 (m, 2H), 7.32 (d, J=6.0 Hz, 1H). $^{13}$C NMR ($CDCl_3$) δ 30.2, 33.4, 35.5, 43.2, 56.8, 126.6, 127.2, 128.3, 128.9, 129.6, 130.4, 130.5, 130.8, 132.5, 136.2, 136.6, 147.5.

Trans-isomers 13c and 13d: $^1$H NMR ($CDCl_3$) δ 1.53 (dd, J=24.8 Hz, 12.4 Hz, 1H), 2.13-2.25 (m, 2H), 2.67-2.74 (m, 1H), 2.94-3.00 (m, 1H), 3.32-3.41 (m, 2H), 4.08 (dd, J=12 Hz, 5.2 Hz, 1H), 6.74 (d, J=12.4 Hz, 1H), 7.00-7.08 (m, 2H), 7.14-7.18 (m, 2H), 7.27 (d, J=7.8 Hz, 1H), 7.38 (d, J=12.4 Hz, 1H). $^{13}$C NMR ($CDCl_3$) δ 34.3, 35.4, 38.3, 46.2, 57.3, 126.5, 126.8, 128.4, 129.4, 129.6, 130.6, 130.7, 130.8, 132.7, 136.0, 138.4, 147.1.

4.6. Synthesis of (4-(3,4-dichlorophenyl)-1,2,3,4-tetrahydronaphthalen-2-yl)methanamine (14a-d)

To a solution of compound 13a (36 mg, 0.108 mmol), in EtOH (5 ml) was added Pd/C (10%, 13 mg). A hydrogen balloon was attached and the reaction mixture was stirred at room temperature for 15 min. The mixture was filtered and concentrated in vacuo. The residue was purified by HPLC, AD column, hexanes: IPA:DEA=90:10:0.05. Compound 14a was obtained as a clear oil (23 mg, 70%).

Compound 14b was prepared from compound 13b (32 mg, 0.096 mmol) according to the procedure outlined above and was obtained as a clear oil (19 mg, 63%). LRMS m/z 306.2.

Compound 14c was prepared from compound 13c (33 mg, 0.099 mmol) following the procedure outlined above and was obtained as a clear oil (26 mg, 86%).

Compound 14d was prepared from 13d (32 mg, 0.096 mmol) following the procedure outlined above and was obtained as a clear oil (20 mg, 70%). LRMS m/z 306.2.

Absolute stereochemistries for compounds 14a-d were determined using a combination of NMR techniques (determination of cis- and trans-configurations) and chiral HPLC analyses using authentic samples, which were prepared from commercial (S)-alpha-tetralone as described above (also compare "General Procedures"). The resulting structures indicating absolute stereochemistries are shown below:

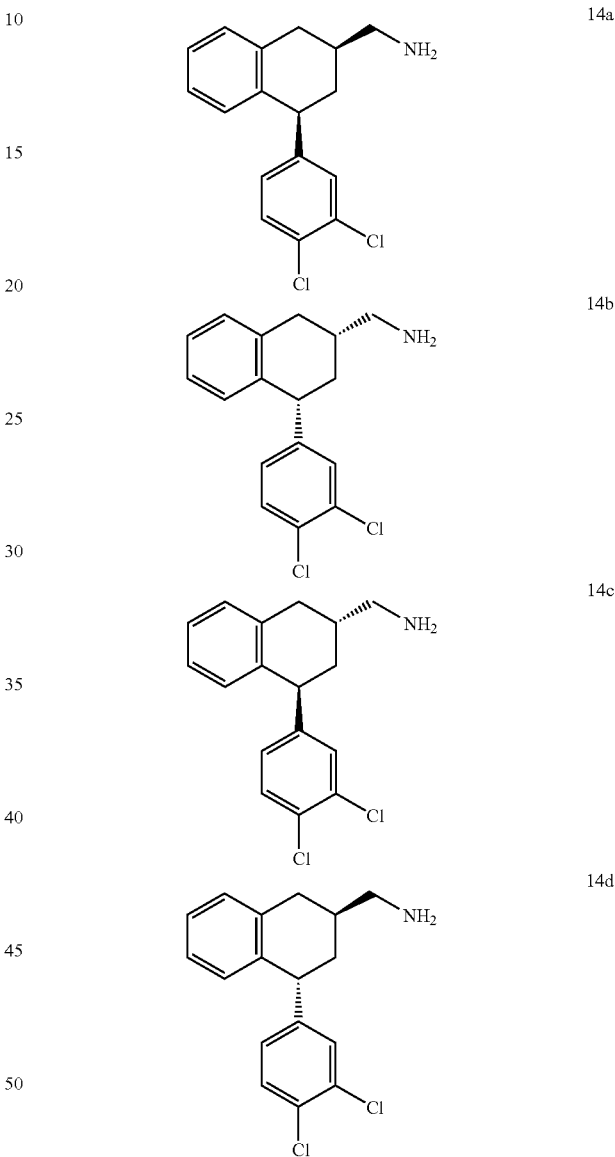

Cis-isomers 14a and 14b: $^1$H NMR ($CDCl_3$) δ 1.33 (brs, 2H), 1.75-1.97 (m, 3H), 2.51 (dd, J=16.8 Hz, 9.8 Hz, 1H), 2.61-2.70 (m, 2H), 3.02 (dd, J=16.8 Hz, 5.2 Hz, 1H), 4.24 (t, J=3.6 Hz, 1H), 6.81-6.91 (m, 2H), 7.07-7.12 (m, 2H), 7.16-7.20 (m, 2H), 7.29 (d, J=6.0 Hz, 1H). $^{13}$C NMR ($CDCl_3$) δ 32.5, 33.8, 35.8, 43.5, 47.8, 126.4, 127.0, 128.4, 129.6, 130.1, 13 0.2, 130 5, 130.9 132.4, 137.1, 148.1. LRMS m/z 306.2.

Trans-isomers 14c and 14d: $^1$H NMR ($CDCl_3$) δ 1.45 (dd, J=24.9 Hz, 12.3 Hz, 1H), 1.75 (brs, 2H), 1.92-2.00 (m, 1H), 2.18-2.24 (m, 1H), 2.69-2.80 (m, 2H), 2.94-3.01 (m, 1 H), 4.06 (dd, J=12 Hz, 5.2 Hz, 1H), 6.72 (d, J=12.4 Hz, 1H), 6.99-7.05 (m, 2H), 7.13-7.18 (m, 2H), 7.27 (d, J=7.8 Hz, 1H), 7.36 (d, J=12.4 Hz.: 1H). $^{13}$C NMR ($CDCl_3$) δ 34.7, 38.2, 38.7, 46.5, 48.2, 126.3, 126.6, 128.4, 129.4, 129.5, 130.4, 130.7, 130.8, 132.7, 136.9, 138.9, 147.6. LRMS m/z 306.2.

Example 5

Synthesis of [4-(3,4-dichlorophenyl)-1,2,3,4-tetrahydro-naphthalen-2-ylmethyl]-methylamine (15a-d)

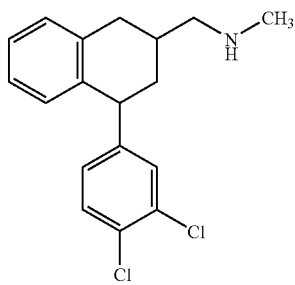

A mixture of compound 12 (0.342 g, 0.92 mmol) and methylamine (2.0 M in THF, 4.6 ml, 9.24 mmol) in a sealed tube was heated to 100° C. for 5 hours. The reaction mixture was evaporated in vacuo. The residue was purified by chromatography, CombiFlash silica gel column, MeOH/CH$_2$Cl$_2$, MeOH from 0% to 5%, to give Compound 15 as a clear oil (mixture of cis and trans diastereomers, ratio=1:1.2, 0.201 g, 68%). The enantiomers Compounds 15(a), 15(b), 15(c), and 15(d) were separated using a preparative chiral HPLC procedure (ChiralPak OD column; hexanes:IPA:DEA=96:10:0.05; μ=8 ml/min; and λ=225 nm) to give 15a-15d (retention times: 11.2 min, 14.7 min, 16.3 min, and 21.2 min, respectively).

Absolute stereochemistries of compounds 15a-d were determined using a combination of NMR techniques (determination of cis- and trans-configurations) and chiral HPLC analyses using authentic samples, which were prepared from commercial (S)-alpha-tetralone as described above (also compare "General Procedures"). The resulting structures indicating absolute stereochemistries are shown below:

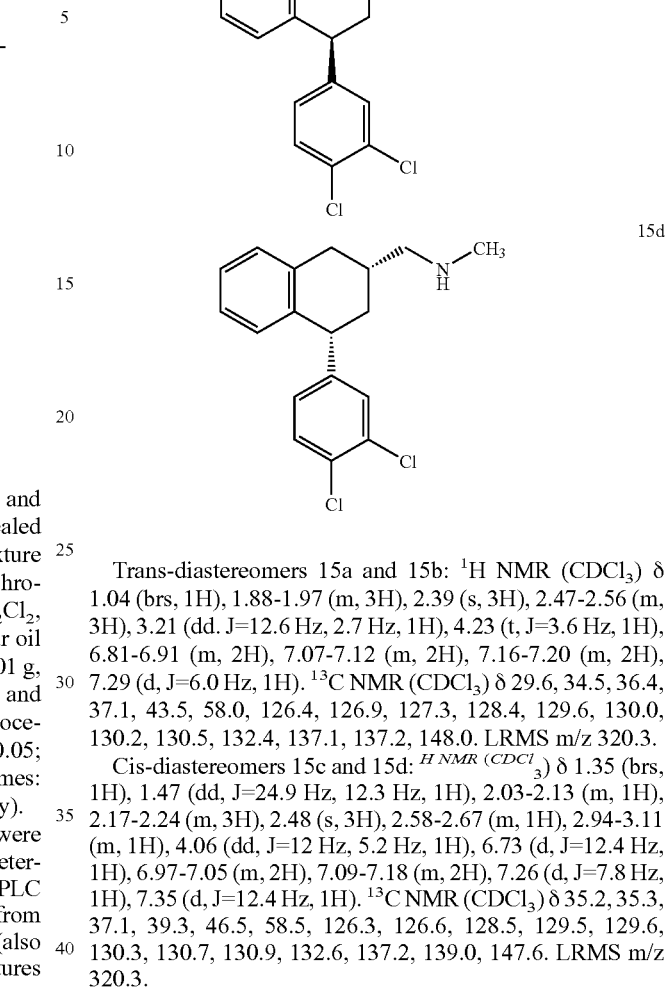

Trans-diastereomers 15a and 15b: $^1$H NMR (CDCl$_3$) δ 1.04 (brs, 1H), 1.88-1.97 (m, 3H), 2.39 (s, 3H), 2.47-2.56 (m, 3H), 3.21 (dd. J=12.6 Hz, 2.7 Hz, 1H), 4.23 (t, J=3.6 Hz, 1H), 6.81-6.91 (m, 2H), 7.07-7.12 (m, 2H), 7.16-7.20 (m, 2H), 7.29 (d, J=6.0 Hz, 1H). $^{13}$C NMR (CDCl$_3$) δ 29.6, 34.5, 36.4, 37.1, 43.5, 58.0, 126.4, 126.9, 127.3, 128.4, 129.6, 130.0, 130.2, 130.5, 132.4, 137.1, 137.2, 148.0. LRMS m/z 320.3.

Cis-diastereomers 15c and 15d: $^1$H NMR (CDCl$_3$) δ 1.35 (brs, 1H), 1.47 (dd, J=24.9 Hz, 12.3 Hz, 1H), 2.03-2.13 (m, 1H), 2.17-2.24 (m, 3H), 2.48 (s, 3H), 2.58-2.67 (m, 1H), 2.94-3.11 (m, 1H), 4.06 (dd, J=12 Hz, 5.2 Hz, 1H), 6.73 (d, J=12.4 Hz, 1H), 6.97-7.05 (m, 2H), 7.09-7.18 (m, 2H), 7.26 (d, J=7.8 Hz, 1H), 7.35 (d, J=12.4 Hz, 1H). $^{13}$C NMR (CDCl$_3$) δ 35.2, 35.3, 37.1, 39.3, 46.5, 58.5, 126.3, 126.6, 128.5, 129.5, 129.6, 130.3, 130.7, 130.9, 132.6, 137.2, 139.0, 147.6. LRMS m/z 320.3.

Example 6

Synthesis of [4-(3,4-dichlorophenyl)-1,2,3,4-tetrahydro-naphthalen-2-ylmethyl]-dimethylamine (16a, 16b)

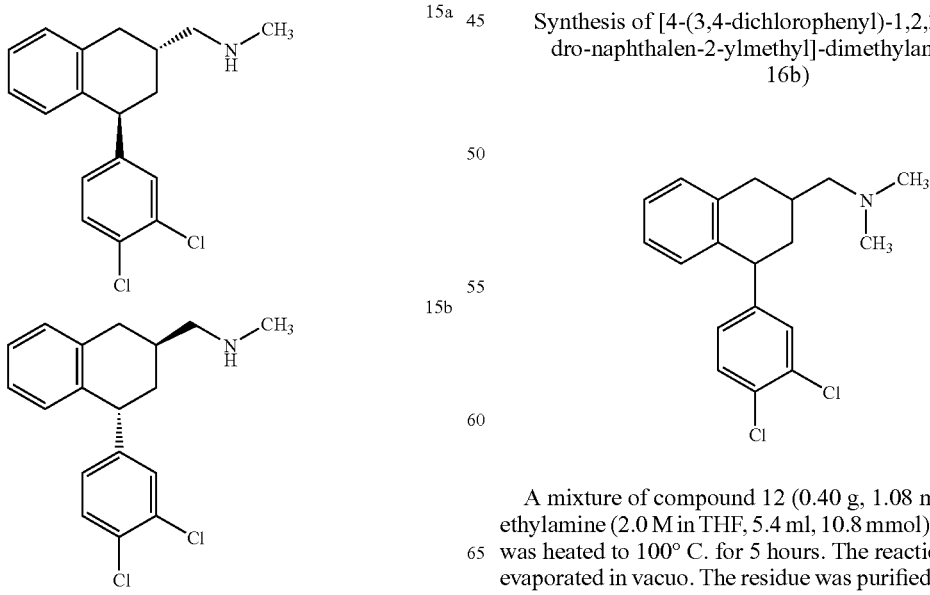

A mixture of compound 12 (0.40 g, 1.08 mmol) and dimethylamine (2.0 M in THF, 5.4 ml, 10.8 mmol) in a sealed tube was heated to 100° C. for 5 hours. The reaction mixture was evaporated in vacuo. The residue was purified by chromatography, CombiFlash silica gel column, MeOH/CH$_2$Cl$_2$, MeOH from 0% to 5%, to give 16 as a clear oil (mixture of cis and trans diastereomers, ratio=1:1.2, 0.253 g, 70%). Cis- and trans-diastereomers were separated using a preparative HPLC procedure (ChiralPak OD column; hexanes: EtOH: MeOH:DEA=96:2:2:0.05; µ=8 ml/min; and λ=225 nm) to give a mixture of cis-enantiomers (16a) and a mixture of trans-enantiomers (16b).

Cis-diastereomers 16a: $^1$H NMR (CDCl$_3$) δ 1.42 (dd, J=24.9 Hz, 12.3 Hz, 1H), 2.03-2.13 (m, 1H), 2.15-2.22 (m, 3H), 2.23 (s, 6H), 2.51-2.61 (m, 1H), 2.94-3.10 (m, 1H), 4.06 (dd, J=12 Hz, 5.2 Hz, 1 H), 6.73 (d, J=12.4 Hz, 1H), 6.97-7.05 (m, 2H), 7.09-7.18 (m, 2H), 7.26 (d, J=7.8 Hz, 1H), 7.35 (d, J=12.4 Hz, 1H). $^{13}$C NMR (CDCl$_3$) δ 33.3, 35.6, 39.7, 46.3, 46.6, 66.6, 126.3, 126.6, 128.5, 129.5, 129.6, 130.3, 130.7, 130.9, 132.6, 137.2, 139.0, 147.7. LRMS m/z 334.3.

Trans-diastereomers 16b: $^1$H NMR (CDCl$_3$) δ 1.82-2.05 (m, 3H), 2.13 (s, 6H), 2.20-2.25 (m, 2H), 2.50 (dd, J=12 Hz, 5.2 Hz, 1H), 2.95-3.04 (m, 1H), 4.22 (t, J=3.6 Hz, 1H), 6.81-6.91 (m, 2H), 7.07-7.12 (m, 2H), 7.16-7.20 (m, 1H), 7.3 (d, J=6.0 Hz, 1H). $^{13}$C NMR (CDCl$_3$) δ 27.3, 34.6, 36.2, 43.3, 46.0, 65.4, 126.4, 126.9, 127.3, 128.4, 129.6, 130.0, 130.2, 130.5, 132.4, 137.1, 137.2, 148.1. LRMS m/z 334.3.

Example 7

Synthesis of 4-(3,4-dichlorophenyl)-2-(dimethylamino)-1,2,3,4-tetrahydronaphthalen-1-ol (23a-d)

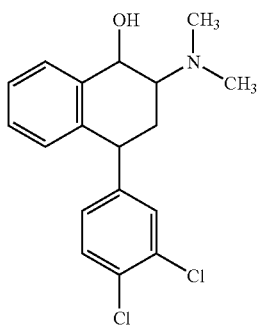

To a solution of 4-(3,4-dichlorophenyl)-3,4-dihydronaphthalen-1(2H)-one (2 g, 6.8 mmol) in ether (30 mL) and chloroform (10 mL) was added bromine (0.4 mL, 1.1 eq) dropwise at 0° C. After one hour, the reaction was quenched with aqueous sodium bisulfate and potassium carbonate. The organic layer was separated and washed with brine before being evaporated to give the crude bromoketone 21 (2.5 g, 100%) as a light brown oil. The NMR indicated the presence of a 4:1 mixture of trans and cis isomers. The trans-isomer could be purified from the mixture by repeated crystallization from ether. The bromoketone (150 mg, 0.305 mmol) was then combined with dimethylamine (800 uL, 2M in THF, 4 eq) in a sealed tube and stirred at ambient temperature for 16 hours. The volatiles were removed in vacuo and the residue was dissolved in ethanol (1 mL). To this solution was added potassium carbonate (110 mg) and the mixture was stirred for ten minutes. After this time, more ethanol and 100 mg of sodium borohydride was added. After one hour of stirring, the reaction was quenched with aqueous sodium bicarbonate and extracted with MTBE. The solvent was evaporated and the residual oil was separated on silica to provide two fractions. The first fraction contained one pair of enantiomers and was separated on a Chiracel OD column to provide compounds 23a and 23b. The other fraction was partially separated on a Chiracel OD to give 23c and 23d. Stereochemistries were not assigned.

Enantiomers 23a and 23b: GCMS Rt=14.26 min, m/z=335 (M+). 1H NMR (CDCl$_3$, δ): 7.70 (d, J=7.8 Hz, 1H), 7.3 (m, 2H), 7.19 (t, J=7.5 Hz, 1H), 7.13 (d, J=2.1 Hz, 1H), 6.88 (d, J=7.7 Hz, 1H), 6.81 (dd, J=2.1, 8.3 Hz, 1H), 4.64 (d, J=9.7 Hz, 1H), 4.36 (dd, J=2.8, 6.2 Hz, 1H), 2.6 (m, 1H), 2.21 (s, 6H), 2.08 (td, J=6.3, 12.4 Hz, 1H), 1.96 (dt, J=3.0, 13.0 Hz, 1H).

23c: GCMS Rt=14.55 min, m/z=335 (M+). 1H NMR (CDCl$_3$, δ): 7.68 (d, J=7.8 Hz, 1H), 7.38 (d, J=8.2 Hz, 1H), 7.2 (m, 2H), 7.11 (t, J=7.5 Hz, 1H), 6.99 (dd, J=2.0, 8.2 Hz, 1H), 6.72 (d, J=7.8 Hz, 1H), 4.74 (d, J=10.1 Hz, 1H), 4.12 (dd, J=5.7, 11.9 Hz, 1H), 2.8 (m, 1H), 2.36 (s, 6H), 2.23 (ddd, J=2.4, 5.8, 12.8 Hz, 1H), 1.59 (q, J=12.4 Hz, 1H).

23d: GCMS Rt=14.31 min, m/z=335 (M+). 1H NMR (CDCl$_3$, δ): 7.51 (d, J=7.6 Hz, 1H), 7.4-7.2 (m, 3H), 7.00 (d, J=2.0 Hz, 1H), 6.97 (d, J=7.6 Hz, 1H), 6.75 (dd, J=2.0, 8.3 Hz, 1H), 4.83 (s, 1H), 4.4 (m, 1H), 2.34 (s, 6H), 2.3 (m, 2H), 2.0 (m, 1H).

Example 8

Synthesis of 2-(1,3-cis)-1-(3,4-dichlorophenyl)-(1,2,3,4-tetrahydronaphthalen-3-yl)ethanamine (25a, 25b)

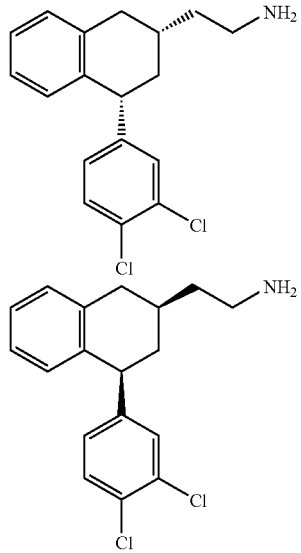

8.1 Synthesis of 2-(-1-(3,4-dichlorophenyl)-1,2-dihydronaphthalen-3-yl)acetonitrile (24)

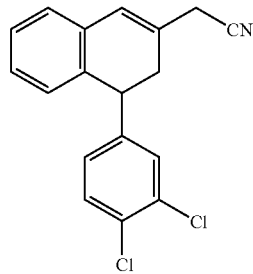

To a stirred solution of diethyl cyanomethyl phosphonate EtO$_2$POCH$_2$CN (0.324 mL, 2 eq) in THF (2 mL) was added sodium hydride (60 mg, 60% in oil) in portions. After 30 minutes, 4-(3,4-dichlorophenyl)-3,4-dihydronaphthalen-2 (1H)-one (beta-tetralone) (291 mg, 1 mmol) was added as a solution in THF (3 mL). After the mixture was stirred for two hours at 0° C., the reaction was quenched with ammonium chloride solution, extracted with MTBE, dried over sodium sulfate and evaporated. The residue was separated on silica to give the unsaturated nitrile (0.24 g, 77%) as a pale-green oil. GC-MS R$_t$=14.59 min, m/z=313 (M+). $^1$H NMR (CDCl$_3$, δ): 7.37 (d, J=8.3 Hz, 1H), 7.3 (m, 2H), 7.2 (m, 2H), 7.00 (dd, J=2.1, 8.3 Hz, 1H), 6.84 (d, J=7.4 Hz, 1H), 6.64 (bs, 1H), 4.17 (t, J=8.1 Hz, 1H), 3.21 (bs, 2H), 2.69 (dd, J=6.9, 17.3 Hz, 1H), 2.52 (dd, J=8.4, 17.2 Hz, 1H). $^{13}$C NMR (CDCl$_3$, δ, mult): 143.9(0), 135.2(0), 132.9(0), 132.5(0), 130.7(1), 130.5(1), 130.0(1), 128.2(1), 127.7(1), 127.5(1), 126.8(1), 126.4(1), 116.5(0), 43.1(1), 35.1(2), 25.1(2).

8.2. Synthesis of 2-(4-(3,4-dichlorophenyl)-1,2,3,4-tetrahydronaphthalen-2-yl)acetonitrile

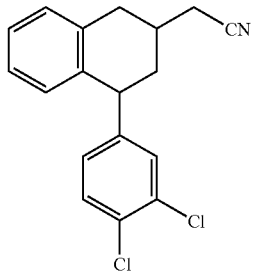

To a solution of the unsaturated nitrile (210 mg, 0.6683 mmol) in 1% wet methanol (28 mL) was added 5% Pd/C (21 mg). The atmosphere was evacuated under vacuum and refilled with hydrogen from a balloon. The reaction was monitored by HPLC and was stopped after 220 minutes. The catalyst was removed by filtration (celite) and the solvent removed in vacuo. The residue was diluted with DCM and filtered through an aminopropyl cartridge. The solvent was stripped to give the intermediate (201 mg, 95%) as a pale-yellow oil. TLC R$_f$ (50% EA/hex)=0.56. HPLC R$_t$ (5-100-8)=11.1 min. $^1$H NMR (CDCl$_3$, δ): 7.40 (d, J=8.3 Hz, 1H), 7.3 (, 1H), 7.2 (m, 2H), 7.1 (m, 1H), 7.02 (dd, J=2.1, 8.2 Hz, 1H), 6.76 (d, J=7.7 Hz, 1H), 4.12 (dd, J=5.4, 12.1 Hz, 1H), 3.06 (ddd, J=2.4, 4.3, 16.2 Hz, 1H), 2.80 (dd, J=12.4, 15.6 Hz, 1H), 2.48 (dd, J=2.6, 6.5 Hz, 2H), 2.3 (m, 2H), 1.66 (q, J=12.6 Hz, 1H). $^{13}$C NMR (CDCl$_3$, δ, mult): 146.3(0), 137.6(0), 135.1(0), 132.6(0), 130.6(1), 130.6(1), 129.3(1), 129.0(1), 128.1(1), 126.7(1), 126.6(1), 118.1(0), 45.9(1), 39.6(2), 35.8(2), 31.9(1), 24.2(2).

8.3. Synthesis of 2-(4-(3,4-dichlorophenyl)-1,2,3,4-tetrahydronaphthalen-2-yl)ethanamine (25)

To a stirring solution of the nitrile (200 mg, 0.6324 mmol) and THF (8 mL) at ambient temperature was added borane-THF (4 mL, 6 eq) dropwise. After heating in the microwave (maximum temperature 130° C.) for five minutes, the reaction was cooled, quenched with 6N HCl, and washed with MTBE. The aqueous layer was chilled, basicified with KOH, and extracted with MTBE. The organic layer was evaporated, diluted with DCM, dried over sodium sulfate, filtered through an aminopropyl cartridge and evaporated to give the pure amine (101 mg, 50%) as a pale-yellow oil. LCMS R$_t$=9.41 min, m/z=320 (M+1). $^1$H NMR (CDCl$_3$, δ): 7.36 (d, J=8.2 Hz, 1H), 7.26 (s, 1H), 7.1 (m, 2H), 7.0 (m, 2H), 6.72 (d, J=7.7 Hz, 1H), 4.05 (dd, J=5.3, 12.0 Hz, 1H), 2.92 (dd, J=2.4, 16.4 Hz, 1H), 2.83 (t, J=7.3 Hz, 2H), 2.60 (m, 1H), 2.1 (m, 1H), 2.0 (M, 1H), 1.6-1.4 (m, 3H). $^{13}$C NMR (CDCl$_3$, δ, mult): 147.4(0), 138.5(0), 137.0(0), 132.3(0), 46.5(1), 41.0(2), 40.8(2), 39.6(2), 36.9(2), 32.3(1).

8.4. Enantiomeric separation of 25; synthesis of tert-butyl 2-(4-(3,4-dichlorophenyl)-1,2,3,4-tetrahydronaphthalen-2-yl)ethylcarbamate (26a, 26b)

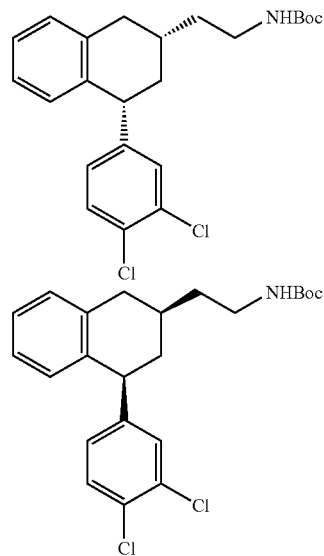

To a solution of the primary amine (100 mg, 0.3122 mmol) in ether (3 mL) was added 10% KOH (1 mL) and BOC anhydride (136 mg, 2 eq). After two hours at ambient temperature, the solution was extracted with MTBE. The organic phase was separated and the volatiles removed in vacuo to give the crude carbamate (208 mg) as a 1:1 mixture with excess BOC anhydride. Most of the anhydride was removed by washing an MBTE solution of the crude product with 1M HCl. This material was separated on a Chiracel OD semiprep column (90:10:0.1 Hex/IPA/DEA) to give the fast moving enantiomer 26a (56.2 mg, 50%) and the slow-moving enantiomer 26b (55.7 mg, 50%). NMR analysis suggested that the formed enantiomers have cis-configuration. TLC R$_f$ (50% EA/hex)=0.48. LCMS R$_t$=11.16 min. $^1$H NMR (CDCl$_3$, δ): 7.36 (d, J=8.2 Hz, 1H), 7.3 (m, 1H), 7.1 (m, 2H), 7.0 (m, 2H), 6.72 (d, J=7.7 Hz, 1H), 4.56 (bs, 1H), 4.04 (dd, J=5.4, 12.0 Hz, 1H), 3.2 (m, 2H), 2.93 (dd, J=2.6, 16.3 Hz, 1H), 2.60 (dd, J=12.0, 16.1 Hz, 1H), 2.2 (m, 1H), 1.9 (m, 1H), 1.57 (q, J=7.1 Hz, 2H), 1.44 (s, 9H), $^{13}$C NMR (CDCl$_3$, δ, mult): 155.9(0), 147.3(0), 138.4(0), 136.7(0), 132.4(0), 130.6(1), 130.4(1), 130.1(0), 129.3(1), 129.0(1), 128.1(1), 126.3(1), 46.4(1), 40.8(2), 38.1(2), 37.0(2), 36.7(2), 32.3(1), 28.4(3).

8.5. Synthesis of cis and trans-2-(1-(3,4-dichlorophenyl)-1,2,3,4-tetrahydronaphthalen-3-yl)acetonitrile (25a and 25b)

To a solution of carbamate 26a (20mg, 0.05585mmol) in CDCl$_3$ was added HCl (1 mL, 4M in dioxane). After 1 hour, the mixture was chilled, quenched with KOH (1 mL, 5M in H$_2$O ), extracted with MTBE and evaporated. The crude oil was diluted in DCM, filtered through an aminopropylcartridge and evaporated to give the pure primary amine 25a (11.5mg, 64%) as a clear oil.

The second enantiomer was prepared from 26b using the procedure described above to give the enantiomeric amine 25b (11.1 mg, 62%) as a clear oil.

Example 9

4-(3,4-dichlorophenyl)-6-methoxy-N-methyl-1,2,3,4-tetrahydronaphthalen-2-amine (32a.1, 32a.2, 32a.3, 32a.4)

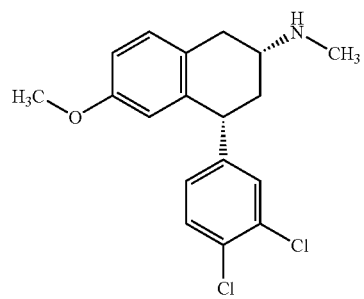

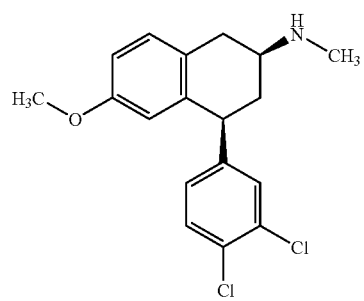

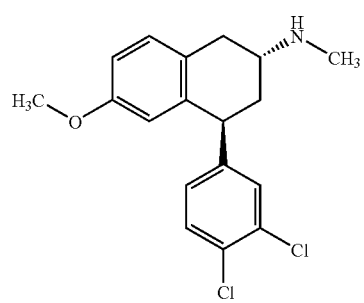

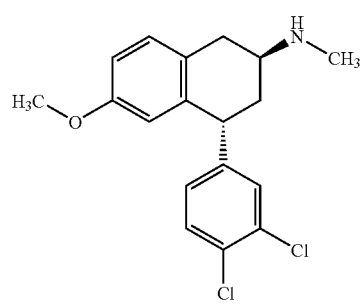

9.1. Synthesis of (E)-4-(3,4-dichlorophenyl)-1-(4-methoxyphenyl)but-3-en-2-one (29a)

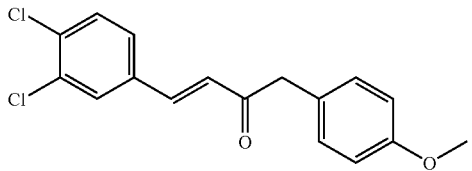

To a cold solution of NaH (40% in mineral oil, 1.0 g, 25 mmol) in THF (30 mL) was added ethanol (0.3mL). After 5 minutes, 1-(4-methoxyphenyl)propan-2-one (2.0 g, 12.2 mmol) was added rapidly dropwise as a solution in 12 mL THF. After 30 minutes, 3,4-dichlorobenzaldehyde (2.4 g, 13.7 mmol) was added as a solution in 24mL THF in one portion. After 2h, the reaction mixture was quenched with aqueous ammonium chloride and the volatile portion was evaporated. The aqueous residue was extracted with MTBE, which was evaporated onto silica gel. The solid material was loaded onto a redisep cartridge and separated on silica gel to give the enone as a pale-yellow oil (32% yield). TLC R$_f$(25% EA/Hex)=0.35. GCMS R$_t$=14.42 min m/z=320 (M+). TLC R$_f$ (25% EA/Hex)=0.26. GCMS R$_t$=14.5 min m/z =320 (M+). $^1$H NMR (CDCl$_3$, δ): 7.58 (d, J=1.9 Hz, $^1$H), 7.49 (d, J=16.0 Hz, 1H), 7.44 (d, J=8.3 Hz, 1H), 7.32 (dd, J=1.9, 8.3 Hz, 1H), 7.17 (d, J=8.5 Hz, 2H), 6.89 (d, J=8.6 Hz, 2H), 6.73 (d, J=16.0 Hz, 1H), 3.86 (s, 2H), 3.80 (s, 3H). $^{13}$C NMR (CDCl$_3$, δ): 196.9, 158.7, 140.3, 140.3, 140.2, 134.4, 134.3, 133.1, 130.8, 130.4, 129.7, 127.3, 126.3, 125.8, 114.2, 55.2, 47.8.

9.2. Synthesis of 4-(3,4-dichlorophenyl)-6-methoxy-3,4-dihydronaphthalen-2(1H)-one (30a)

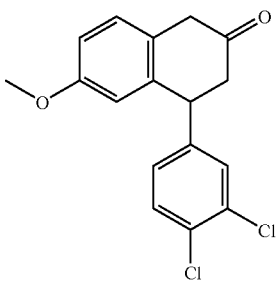

The ketone 29a (2.0 g, 6.23 mmol) was dissolved in xylenes (50 mL) and stirred with a mechanical stirrer in a three-necked round bottom flask. The flask was fitted with a condenser and heated to 165° C. When the reaction had warmed up, PPA (40 g) was added via syringe as rapidly as possible. The reaction mixture was then stirred rapidly and monitored by HPLC. After three hours, the reaction was cooled and the xylene layer was decanted. Evaporation and separation of the crude residue on a redisep cartridge provided some recovered starting enone (0.34 g, 17%) and the desired tetralone (0.36 g, 18%) as a clear oil. TLC R$_f$(25% EA/Hex)=0.25. GCMS R$_t$=14.26 min m/z=320 (M+). $^1$H NMR (CDCl$_3$, δ): 7.40 (d, J=8.3 Hz, 1H), 7.21 (d, J=2.0 Hz, 1H), 7.12 (d, J=8.4 Hz, 1H), 6.96 (dd, J=2.1, 8.3 Hz, 1H), 6.84 (dd, J=2.6, 8.4 Hz, 1H), 6.53 (d, J=2.4 Hz, 1H), 4.38 (t, J=6.3 Hz, 1H), 3.76 (s, 3H), 3.56 (dd, J=20.3, 42.4 Hz, 2H), 2.89 (m, 2H). $^{13}$C NMR (CDCl$_3$, δ): 208.6, 158.6, 141.7, 138.9, 132.8, 131.1, 130.7, 129.8, 129.7, 127.2, 125.0, 113.8, 112.8, 55.2, 45.5, 44.0, 43.8.

9.3. 4-(3,4-dichlorophenyl)-6-methoxy-N-methyl-1,2,3,4-tetrahydronaphthalen-2-amine (32a)

To a solution of the tetralone 30a in THF in methanol was added methylamine hydrochloride. After dissolution (10 min), sodium cyanoborohydride was added in a single portion. The resultant mixture was stirred at 50° C. for three hours. After cooling, the mixture was diluted with sodium bicarbonate solution and extracted with MTBE. The organic layer was evaporated to give the crude amine 32a (160 mg) as a mixture of four configurational isomers.

These amines were separated using a combination of Chiracel OD (98:2:0.1 Hex/IPA/DEA) and AD (95:5:0.1 Hex/IPA/DEA) columns. The order of elution changes between the two columns and was defined based on the OD column as peaks E1, E2, E3, and E4. Retention times are summarized in Table 3, below.

TABLE 3

| Retention times for each diastereomer [min] | | | | |
|---|---|---|---|---|
| | 32a.1 E1 Trans | 32a.2 E2 Cis | 32a.3 E3 Trans | 32a.4 E4 Cis |
| HPLC R$_t$ (Chiracel OD, 98:2:0.1 Hex/IPA/DEA) | 14.1 | 15.4 | 17.2 | 18.6 |
| HPLC R$_t$ (Chiracel AD, 95:5:0.1 Hex/IPA/DEA) | 11.0 | 11.9 | 9.2 | 10.2 |

Cis-isomers 32a.2 and 32a.4: LCMS R$_t$=7.00 min m/z=336 (M+1). $^1$H NMR (CDCl$_3$, δ): 7.37 (d, J=8.3 Hz, 1H), 7.29 (d, J=2.1 Hz, 1H), 7.06 (d, J=8.4 Hz, 1H), 7.01 (dd, J=2.1, 8.2 Hz, 1H), 6.72 (dd, J=2.6, 8.4 Hz, 1H), 6.24 (d, J=2.4 Hz, 1H), 4.04 (dd, J=5.4, 12.3 Hz, 1H), 3.64 (s, 3H), 3.06 (ddd, J=2.0, 4.6, 15.4 Hz, 1H), 2.89 (tdd, J=2.9, 4.7, 11.2 Hz, 1H), 2.62 (dd, J=11.1, 15.3 Hz, 1H), 2.52 (s, 3H), 2.32 (m, 1H), 1.55 (dd, J=12.3, 24.0 Hz, 1H). $^{13}$C NMR (CDCl$_3$, δ): 158.0, 146.9, 139.3, 132.6, 130.8, 130.7, 130.6, 130.5, 128.7, 128.3, 114.3, 112.7, 60.7, 55.4, 46.8, 41.7, 37.0, 32.2.

Trans-isomers 32a.1 and 32a.3: LCMS R$_t$=7.17 min m/z=336 (M+1). $^1$H NMR (CDCl$_3$, δ): 7.32 (d, J=8.3 Hz, 1H), 7.14 (d, J=2.1 Hz, 1H), 7.08 (d, J=8.5 Hz, 1H), 6.88 (dd, J=2.1, 8.3 Hz, 1H), 6.77 (dd, J=2.7, 8.4 Hz, 1H), 6.38 (d, J=2.6 Hz, 1H), 4.23 (t, J=5.8 Hz, 1H), 3.68 (s, 3H), 3.10 (dd, J=4.8, 16.0 Hz, 2.9 (m, 1H), 2.61 (dd, J=7.9, 16.0 Hz, 1H), 2.42 (s, 3H), 2.0 (m, 2H), 1.9 (bs, 1H). $^{13}$C NMR (CDCl$_3$, δ): 158.1, 147.4, 137.9, 132.4, 130.7, 130.6, 130.4, 130.2, 128.3, 127.8, 114.6, 113.5, 55.4, 51.5, 43.1, 37.8, 35.2, 33.7.

Example 10

Synthesis of 4-(3,4-dichlorophenyl)-5-methoxy-N-methyl-1,2,3,4-tetrahydronaphthalen-2-amine (32b.1, 32b.2)

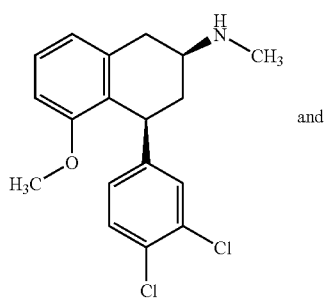

and

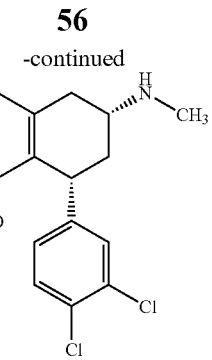

10.1. Synthesis of (E)-4-(3,4-dichlorophenyl)-1-(3-methoxyphenyl)but-3-en-2-one (29b)

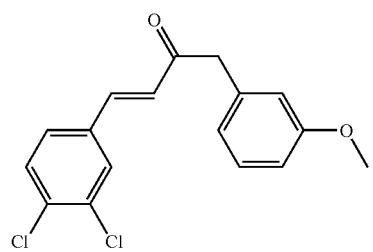

The title compound was prepared in 36% yield from 1-(3-methoxyphenyl)propan-2-one and 3,4-dichlorobenzaldehyde following the procedure outlined in Example 9.1 above. $^1$H NMR (CDCl$_3$, δ): 7.56 (d, J=2.0 Hz, 1H) 7.48 (d, J=16.0 Hz, 1H), 7.42 (d, J=8.3 Hz, 1H), 7.3 (m, 2H), 6.8(m, 3H), 6.73 (d, J=16.0 Hz, 1H), 3.88 (s, 2H), 3.79 (s, 3H). $^{13}$C NMR (CDCl$_3$, δ): 196.5, 159.8, 140.4, 135.3, 134.4, 134.3, 133.1, 130.8, 129.8, 129.7, 127.3, 126.2, 121.7, 115.1, 112.5, 55.1, 48.7.

10.2. 4-(3,4-dichlorophenyl)-5-methoxy-3,4-dihydronaphthalen-2(1H)-one (30c)

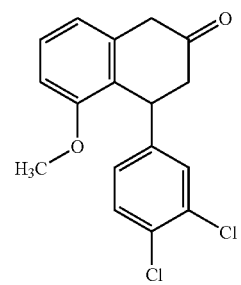

The cyclization of the 2-methoxy aryl enone 29b following the procedure outlined in Example 9.2 gave a mixture of tetralones. The products were separated by silica gel column chromatography to give the 5-methoxytetralone 30c (24%) followed by the 7-methoxytetralone 30b (32%).

The isolated 5-methoxy tetralone 30c appeared to be a mixture of rotational isomers that were slow to interconvert on the NMR time-scale. For example, the characteristic bis-benzylic proton coupling pattern appeared at both 4.9 (dd) and 4.4 (t) ppm. The ratio of the two peaks was 85:15. $^1$H NMR (CDCl₃, δ): 7.4-6.5 (m, 6H), 4.95 (dd, J=1.9, 6.1 Hz, 0.85H), 4.37 (t, J=6.2 Hz, 0.15H), 3.80 (s, 3H), 3.6 (m, 0.30H) 3.53 (dd, J=21.0, 59.6 Hz, 1.7H), 2.9 (m, 1.7H), 2.2 (m, 0.30H).

10.3. Synthesis of 4-(3,4-dichlorophenyl)-5-methoxy-N-methyl-1,2,3,4-tetrahydronaphthalen-2-amine (32b.1, 32b.2)

The title compound was prepared from 30c following the procedure outlined in Example 9.3. The reaction yielded the cis diastereomers selectively (cis:trans>10:1). The amine componrients were isolated from the crude mixture by reverse-phase HPLC and the cis enantiomers were then separated using the Chiracel OD (90:10:0.1 Hex/IPA/DEA) column first, followed by the Chiracel AD (2:3:95:0.1 MeOH/EtOH/Hex/IPA) to give the enantiomers 32b.1 and 32b.2. The retention times for both enantiomers are summarized in Table 4, below.

TABLE 4

| Retention times for each cis-enantiomer [min] | | |
|---|---|---|
| | 32b.1 E1 Cis | 32b.2 E2 Cis |
| HPLC R$_t$ (Chiracel OD, 95:5:0.1 Hex/IPA/DEA) | 9.3 | 11.8 |
| HPLC R$_t$ (Chiracel AD, 2:3:95:0.1 MeOH/EtOH/Hex/DEA) | 7.60 | 8.3 |

Cis-enantiomers (32b.1 and 32b.2): LCMS R$_t$=7.5min m/z=336 (M+1). ¹H NMR (CDCl₃, δ): 7.26 (d, J=8.3 Hz, 1H), 7.16 (m, 2H), 6.88 (dd, J=2.1, 8.3 Hz, 1H), 6.79 (d, J=7.6 Hz, 1H), 6.64 (d, J=8.1 Hz, 1H), 4.17 (dd, J=7.9 10.2 Hz, 1H), 3.44 (s, 3H), 3.02 (dt, J=3.2, 15.2 Hz, 1H), 2.79 (tt, J=3.5, 11.0 Hz, 1H), 2.64 (dd, J=11.0, 14.8 Hz, 1H), 2.48 (s, 3H), 2.44 (m, 1H), 1.4 (m, 2H). _C NMR(CDCl₃, δ): 157.6, 149.3, 138.2, 131.6, 129.9, 128.8, 128.7, 127.6, 126.3, 126.3, 121.6, 108.9, 55.3, 55.0, 41.3, 41.2, 37.6, 33.6.

Example 11

Synthesis of (E)-4-(3,4-dichlorophenyl)-1-(3,4-dimethoxyphenyl)but-3-en-2-one (29c)

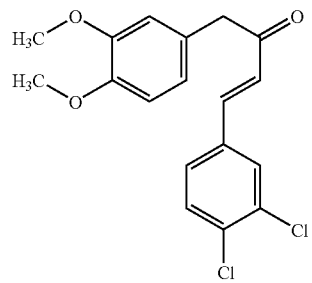

The title compound was prepared in (37% yield) from following the procedure outlined in Example 9. 1, above. TLC R$_f$(10% EA/Hex)=0. 19. GCMS R$_t$=15.06 min m/z=350 (M+). ¹H NMR (CDCl₃, δ): 7.57 (d, J=2.0 Hz, 1H), 7.49 (d, J=16.0 Hz, 1H), 7.43 (d, J=8.3 Hz, 1H), 7.31 (dd, J=2.0, 8.3 Hz 1H), 6.85 (d, J=8.2 Hz, 1H), 6.80 (dd, J=1.9, 8.2 Hz, 1H), 6.75 (d, J=1.8 Hz, 1H), 6.74 (d, J=16.0 Hz, 1H) 3.86 (s, 6H), 3.85 (s, 2H). 13C NMR (CDCl₃, δ): 197.0, 149.1, 148.1, 140.4, 134.4, 134.3, 133.2, 130.8, 129.7, 127.3, 126.2, 126.1, 121.6, 11 2.3, 111.4, 55.8, 48.4.

Example 12

Synthesis of 4-(3,4-dichlorophenyl)-7-methoxy-N-methyl-1,2,3,4-tetrahydronaphthalen-2-amine (32c.1, 32c.2, 32c.3, 32c.4)

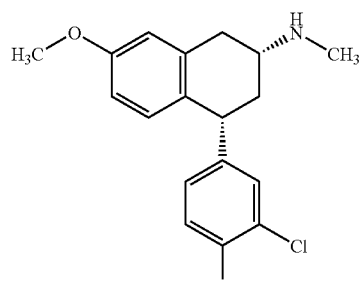

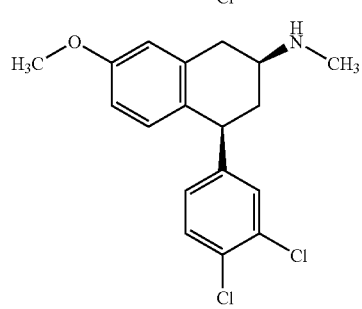

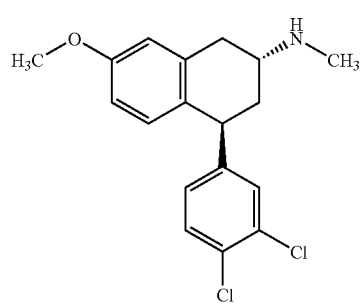

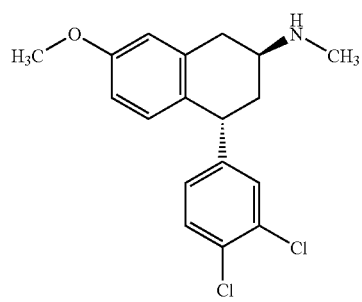

5 12.1. 4-(3,4-dichlorophenyl)-7-methoxy-3,4-dihydronaphthalen-2(1H)-one (30b)

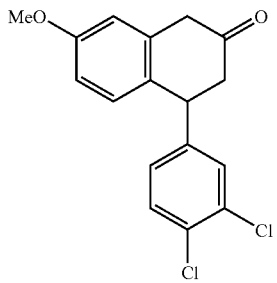

The cyclization of the 2-methoxy aryl enone 29b following the procedure outlined in Example 9.1, above, gave a mixture of tetralones. The products were separated by silica gel column chromatography to give the 5-methoxytetralone 30c (24%) followed by the 7-methoxytetralone 30b (32%). $^1$H NMR (CDCl$_3$, δ): 7.36 (d, J=8.3 Hz, 1H), 7.19 (d, J=2.1 Hz, 1H), 6.94 (dd, J=2.1, 8.3 Hz, 1H), 6.89 (d, J=8.4 Hz, 1H), 6.74 (m, 2H); 4.36 (t, J=6.3 Hz, 1H), 3.79 (s, 3H), (dd, J=20.4, 37.5 Hz, 2H), 2.85 (m, 2H).

12.2. Synthesis of 4-(3,4-dichlorophenyl)-7-methoxy-N-methyl-1,2,3,4-tetrahydronaphthalen-2-amine (32c.1, 32c.2, 32c.3, 32c.4)

The title compound was prepared from 30b following the procedure outlined in Example 9.3. The amine components were isolated from the crude mixture by reverse-phase HPLC and all four isomers were then separated using a combination of Chiracel OD (90:10:0.1 Hex/IPA/DEA) and AD (95:5:0.1 Hex/IPA/DEA) columns. These isomers were designated E1, E2, E3, and E4 based on the order of elution from the OD column. The order of elution differs on the AD column. Retention times for the isomers are summarized in Table 5, below.

TABLE 5

Retention times for each isomer [min]

|  | 32c.1 E1 Cis | 32c.2 E2 Trans | 32c.3 E3 Trans | 32c.4 E4 Cis |
|---|---|---|---|---|
| HPLC R$_t$ (Chiracel OD, 90:10:0.1 Hex/IPA/DEA) | 7.1 | 8.2 | 8.8 | 12.2 |
| HPLC R$_t$ (Chiracel AD, 95:5:0.1 Hex/IPA/DEA) | 15.0 | 15.0 | 18.3 | 13.6 |

Cis-isomers 32c.1 (E1) and 32c.4 (E4): LCMS R$_t$=7.1 min m/z=336 (M+1). $^1$H NMR (CDCl$_3$, δ): 7.32 (d, J=8.2 Hz, 1H), 7.12 (d, J=2.0 Hz, 1H), 6.88 (dd, J=2.0, 8.3 Hz, 1H), 6.78 (d, J=8.1 Hz, 1H), 6.7 (m, 2H), 4.21 (t, J=5.8 Hz, 1H), 3.79 (s, 3H), 3.13 (dd, J=4.8, 16.3 Hz, 1H), 2.90 (m, 1H), 2.67 (dd, J=7.9, 16.3 Hz, 1H), 2.43 (s, 3H), 2.0 (m, 2H), 1.8 (bs, 1H). $^{13}$C NMR (CDCl$_3$, δ): 158.2, 147.7, 136.7, 132.1, 130.9, 130.5, 130.1, 129.9, 128.8, 128.0, 113.7, 112.8, 55.2, 51.1, 41.8, 37.8, 36.1, 33.5.

Trans-isomers 32c.2 (E2) and 32c.3 (E3): LCMS R$_t$=7.1 min m/z=336 (M+1). $^1$H NMR (CDCl$_3$, δ): 7.37 (d, J=8.3 Hz, 1H), 7.28 (d, J=2.0 Hz, 1H), 7.01 (dd, J=2.0, 8.2 Hz, 1H), 6.6 (m, 3H), 4.02 (dd, J=5.3, 12.1 Hz, 1H), 3.78 (s, 3H), 3.08 (ddd, J=2.0, 4.6, 15.8 Hz, 1H), 2.92 (tdd, J=2.9, 4.7, 11.2 Hz, 1H), 2.69 (dd, J=11.1, 5.6 Hz, 1H), 2.53 (s, 3H), 2.32 (m, 1H), 1.54 (dd, J=12.2, 24.0 Hz, 1H), 1.4 (bs, 1H). $^{13}$C NMR (CDCl$_3$, δ): 158.0, 147.0, 137.1, 132.3, 130.5, 130.4, 130.1, 130.1, 128.0, 113.5, 112.5, 55.5, 55.2, 45.1, 40.6, 37.6, 33.6.

Example 13

4-(3,4-dichlorophenyl)-6-methoxy-N,N-dimethyl-2,3,4-tetrahydronaphthalen-2-amine (33a.1, 33a.2, 33a.3, 33a.4)

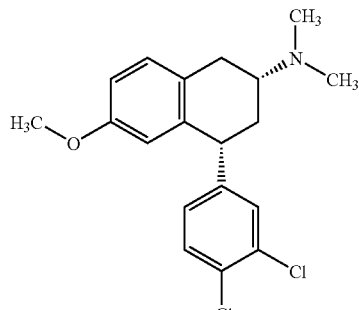

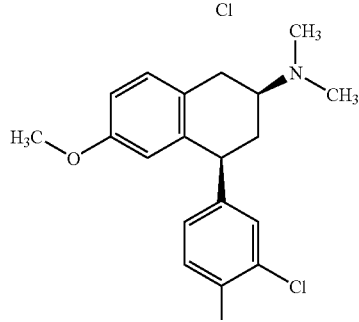

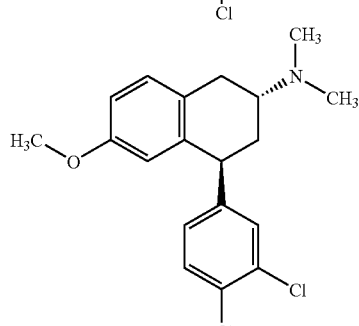

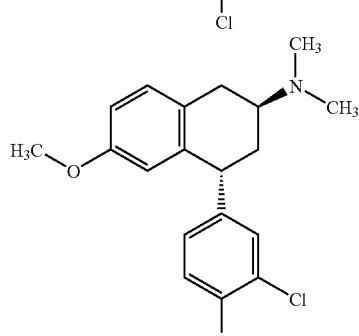

A solution of the respective methylamine 32a (Example 9) (e.g., 16 mg) in formic acid (e.g., 1 mL) and formaldehyde (e.g., 1 mL) was stirred at 100° C. for two hours. After chilling on ice, the solution was quenched with aqueous sodium hydroxide and extracted with MTBE. The solvent was removed and the residue was filtered through an aminopropyl cartridge to give the desired dimethylamine as a clear oil (e.g., 11.5 mg).

Cis-enantiomers 33a.2 and 33a.4: LCMS R$_t$=7.87min m/z=350 (M+1). $^1$H NMR (CDCl$_3$, δ): 7.38 (d, J=8.2 Hz, 1H), 7.28 (d, J=2.1 Hz, 1H), 7.08 (d, J=8.4 Hz, 1H), 7.01 (dd, J=2.0, 8.2 Hz, 1H), 6.73 (dd, J=2.6, 8.4 Hz, 1H), 6.23 (d, J=2.4 Hz, 1H), 4.03 (dd, J=5.3, 12.2 Hz, 1H), 3.64 (s, 3H), 2.96 (m, 1H), 2.83 (m, 1H), 2.75 (tdd, J=2.4, 4.3, 11.3 Hz, 1H), 2.36 (s, 6H), 2.29 (m, 1H), 1.62 (dd, J=12.2, 23.8 Hz, 1H). $^{13}$C NMR (CDCl$_3$, δ): 158.0, 146.9, 139.3, 132.6, 130.8, 130.7, 130.6, 130.5, 128.7, 128.3, 114.3, 112.7, 60.7, 55.4, 46.8, 41.7, 37.0, 32.2.

Trans-enantiomers 33a.1 and 33a.3: LCMS Ft =7.85min m/z=350 (M+1). $^1$H NMR (CDCl$_3$, δ): 7.32 (d, J=8.3 Hz, 1H), 7.1 (m, 2H), 6.86 (dd, J=1.9, 8.3 Hz, 1H), 6.77 (dd, J=2.6, 8.4 Hz, 1H), 6.41 (d, J=2.5 Hz, 1H), 4.28 (t, J=5.2 Hz, 1H), 3.69 (s, 3H), 2.96 (dd, J=4.8, 16.0 Hz, 1H), 2.77 (dd, J=9.3, 15.9 Hz 1H), 2.54 (sep, J=4.5 Hz, 1H), 2.26 (s, 6H), 2.1 (m, 2H). $^{13}$C NMR (CDCl$_3$, δ): 158.1, 147.3, 137.8, 132.4, 130.7, 130.6, 130.3, 128.6, 128.3, 114.4, 114.4, 113.5, 56.4, 55.4, 55.4, 43.8, 42.1, 35.1, 31.5.

Example 14

4-(3,4-dichlorophenyl)-7-methoxy-N,N-dimethyl-1,2,3,4-tetrahydronaphthalen-2-amine (33c.1, 33c.2, 33c.3, 33c.4)

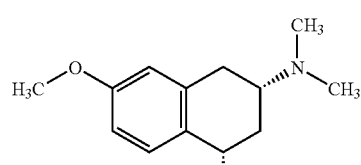

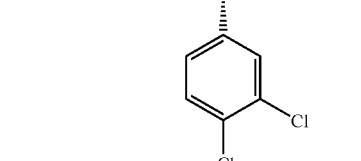

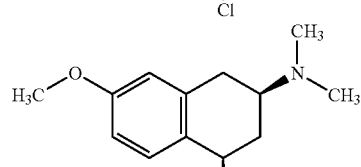

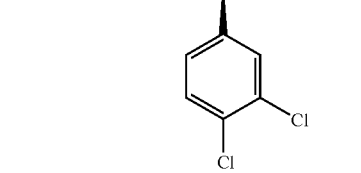

-continued

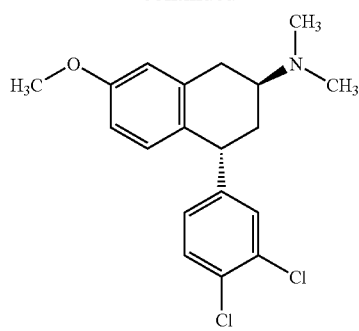

The title compounds were prepared from 32c.1, 32c.2, 32c.3 and 32c.4, respectively, following the procedure outlined in Example 13. All four enantiomers were obtained.

Cis-enantiomers 33c.1 and 33c.4: LCMS R$_t$=8.65min m/z=350 (M+1). $^1$H NMR (CDCl$_3$, δ): 7.31 (d, J=8.3 Hz, 1H), 7.09 (d, J=2.1 Hz, 1H), 6.86 (dd, J=2.1, 8.3 Hz, 1H), 6.80 (d, J=8.1 Hz, 1H), 6.7 (m, 2H), 4.27 (t, J=5.2 Hz, 1H), 3.80 (s, 3H), 2.98 (dd, J=4.9, 16.4 Hz, 1H), 2.82 (dd, J=9.3, 16.4 Hz, 1H), 2.55 (m, 1H), 2.27 (s, 6H), 2.1 (m, 2H).

Trans-enantiomers 33c.2 and 33c.3: LCMS R$_t$=8.72min m/z=350 (M+1). $^1$H NMR (CDCl$_3$, δ): 7.38 (d, J=8.3 Hz, 1H), 7.27 (d, J=2.1 Hz, 1H), 7.01 (dd, J=2.0, 8.2 Hz, 1H), 6.68 (s, 1H), 6.62 (bs, 2H), 4.00 (dd, J=4.9, 12.4 Hz, 1H), 3.78 (s, 3H), 2.9 (m, 2H), 2.78 (tdd, J=2.3, 5.2, 11.3 Hz, 1H), 2.37 (s, 6H), 2.28 (m, 1H), 1.61 (dd, J=12.1, 24.0 Hz, 1H).

Example 15

Synthesis of 1-(3,4-dichlorophenyl)-N-methyl-1,2,3,4-tetrahydronaphthalen-2-amine (36a-d)

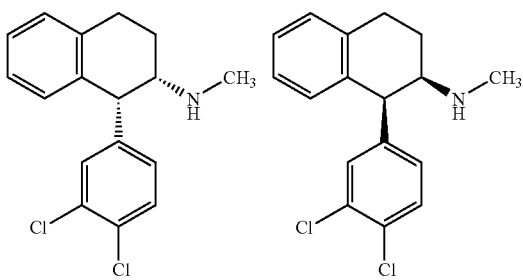

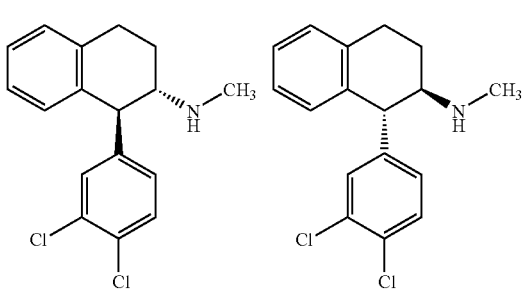

15.1. Synthesis of 1-(3,4-dichlorophenyl)-3,4-dihydronaphthalen-2(1H)-one (35)

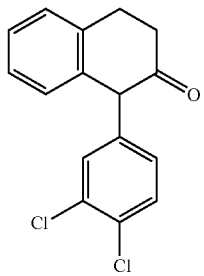

To a stirring solution of β-tetralone (34) (1.00 g, 6.84 mmol) and pd(dba)$_2$ (39 mg, 1 mol%) in toluene was added t-Bu$_3$P (228 uL, 10 wt % in hexanes, 1.1%). The solution was chilled (dry-ice bath) before adding LiHMDS (7.5 mL, 1M in hexanes, 1.1 eq) followed by 1-bromo-3,4-dichlorobenzene (1 mL, 1.1 eq). The solution was then allowed to warm to ambient temperature and heated under microwave radiation for 5 minutes (maximum temperature 140° C.). After cooling, the reaction was quenched with aqueous ammonium chloride and extracted with MTBE. The organic layer was dried with sodium sulfate, filtered through celite, and evaporated. The crude oil was separated on silic gel to give the title compound (1.45 g, 73%) as a slight brown oil. This material was assayed as 90% pure. TLC R$_f$(25% EA/Hex)=0.42. GCMS R$_t$=13.21 min m/z=290 (M+). $^1$H NMR (CDCl$_3$, δ): 7.37 (d, J=8.3 Hz, 1H), 7.3-7.2 (m, 3H), 7.17 (d, J=2.1 Hz, 1H), 6.9 (m, 2H), 4.68 (s, 1H), 3.1 (m, 2H), 2.7 (m, 2H). $^{13}$C NMR (CDCl$_3$, δ): 208.4, 137.7, 136.7, 135.3, 132.7, 131.5, 130.7, 130.5, 129.2, 128.2, 128.1, 127.7, 127.3, 58.6, 37.1, 28.0.

15.2. Synthesis of 1-(3,4-dichlorophenyl)-N-methyl-1,2,3,4-tetrahydronaphthalen-2-amine (36a-d)

To a solution of tetralone 35 (400mg, 1.374 mmol) in THF (10 mL) and methanol (15mL) was added methylamine hydrochloride (1.12 g, 10 eq). The resultant mixture was stirred at 50° C. After dissolution (10 min), sodium cyanoborohydride (6.9 mL, 1M in THF, 5 eq) was added in a single portion. After 20 hours, the organic layer was evaporated, filtered through silica and an aminopropyl cartridge. The crude oil was then diluted with sodium bicarbonate solution and extracted with MTBE to give the amine (280 mg, 66%) as a mixture of four stereoisomers (1:1:1:1).

These amines were separated using a Chiracel OD (98:2:0.1 Hex/IPA/DEA) column to give three fractions. The first was pure E1; the second was a mixture of E2 and E3; and the third was pure E4. The mixture was further separated using a Chiracel OD (2:3:95:0.1 MeOH/EtOHHex/DEA) column. The order of elution of the middle fractions changes between these columns and was defined based on the OD 98:2:0.1 conditions. Retention times are summarized in Table 6, below.

TABLE 6

| Retention times for each isomer [min] | | | | |
|---|---|---|---|---|
| | 36c E1 Trans | 36a E2 Cis | 36d E3 Trans | 36b E4 Cis |
| HPLC R$_t$ (Chiracel OD, 98:2:0.1 Hex/IPA/DEA) | 6.0 | 6.7 | 7.9 | 13.7 |
| HPLC R$_t$ (Chiracel OD, 2:3:95:0.1 MeOH/EtOH/Hex/DEA) | 5.5 | 6.2 | 7.0 | 10.5 |

Cis-enantiomers 36a (E2) and 36b (E4): LCMS R$_t$=8.83 min m/z=306 (M+1). $^1$H NMR (CDCl$_3$, δ): 7.31 (d, J=8.3 Hz, 1H), 7.2-7.1 (m, 3H), 7.1-7.0 (m, 1H), 6.9 (m, 2H), 4.32 (d, J=5.1 Hz, 1H), 3.1-2.8 (m, 3H), 2.50 (s, 3H), 1.9 (m, 1H), 1.6 (m, 1H). $^{13}$C NMR (CDCl$_3$, δ): 142.5, 137.4, 136.4, 132.0, 131.9, 130.5, 129.7, 129.6, 128.8, 126.7, 126.0, 58.5, 48.3, 33.9, 28.1, 23.7.

Trans-enantiomers 36c (E1) and 36d (E3): LCMS R$_t$=9.12 min m/z=306 (M+1). $^1$H NMR (CDCl$_3$, δ): 7.37 (d, J=8.2 Hz, 1H), 7.2 (m, 1H), 7.1 (m, 1H), 7.0 (m, 1H), 6.97 (dd, J=2.0, 8.2 Hz, 1H), 6.69 (d, J=7.8 Hz, 1H), 3.91 (d, J=7.7 Hz, 1H), 2.94 (t, J=6.5 Hz, 2H), 7.51 (td, J=1.4, 7.5 Hz, 1H), 2.42 (s, 3H), 2.2 (m, 1H), 1/7 (m, 1H). $^{13}$C NMR (CDCl$_3$, δ): 145.1, 137.0, 136.4, 132.5, 131.4, 131.4, 130.8, 130.0, 129.9, 128.4, 126.7, 126.0, 62.3, 51.4, 33.7, 27.1, 25.5.

Example 16

Synthesis of 1-(3,4-dichlorophenyl)-N,N-dimethyl-1,2,3,4-tetrahydronaphthalen-2-amine (37a-d)

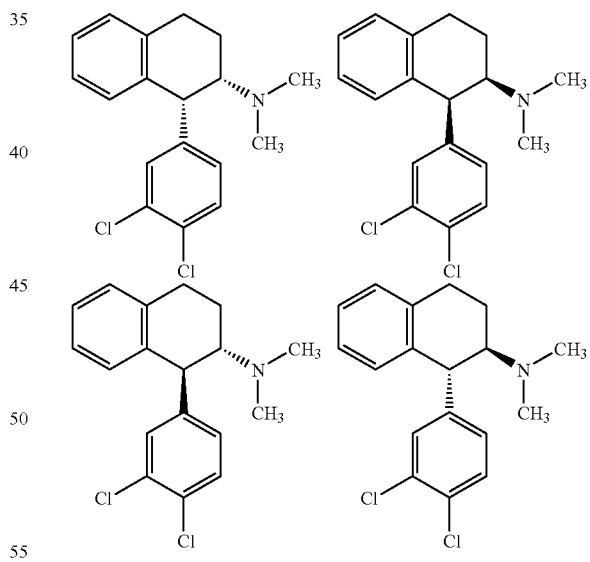

A stirring solution of the respective methylamine 36 (e.g., 20-25 mg) in formic acid (e.g., 1 mL) and formaldehyde (e.g., 1 mL) was stirred at 100° C. for three hours. After chilling on ice, the solution was quenched with saturated aqueous sodium hydroxide (2 mL) and extracted with MTBE. The solvent was removed and the residue was filtered through an aminopropyl cartridge to give the desired dimethylamine as a clear oil.

Cis-enantiomers 37a and 37b: LCMS R$_t$=11.3 min m/z=320 (M+1). $^1$H NMR (CDCl$_3$, δ): 7.26 (d, J=8.3 Hz, 1H), 7.2-7.1 (m, 3H), 7.1-7.0 (m, 1H) (m, 2H), 4.34 (d, J=4.9 Hz, 1H), 3.08 (dd, J=6.4, 17.4 Hz, 1H), 2.9 (m, 1H), 2.78 (ddd, J=3.0, 5.0, 12.8 Hz, 1H), 2.19 (s, 3H), 1.95 (m, 1H), 1.71 (ddd, J=6.5, 12.9, 24.7 Hz, 1H). $^{13}$CNMR(CDCl$_3$, δ): 143.7, 138.4, 135.9, 132.3, 131.4, 130.5, 130.0, 129.9, 129.2, 128.7, 126.6, 126.0, 64.8, 47.7, 43.1, 29.2, 19.6,.

Trans-enantiomers 37c and 37d: LCMS R$_t$=11.3min m/z=320 (M+1). $^1$H NMR (CDCl$_3$, δ): 7.32 (d, J=8.2 Hz, 1H), 7.17 (d, J=2.0 Hz, 1H), 7.1 (m, 2H), 7.0 (m, 1H), 6.91 (dd, J=2.1, 8.3 Hz, 1H), 6.72 (d, J=7.8 Hz, 1H), 4.12 (d, J=8.3 Hz, 1H), 2.97 (dt, J=5.4, 16.7 Hz, 1H), 2.9 (m, 1H), 2.75 (td, J=2.3, 9.0 Hz, 1H), 2.29 (s, 3H), 2.0 (m, 1H), 1.7 (m, 1H). $^{13}$C NMR (CDCl$_3$, δ): 146.6, 137.9, 136.9, 132.0, 131.0, 130.4, 130.0, 129.9, 128.6, 126.2, 126.0, 67.3, 48.2, 41.4, 28.4, 20.5.

Example 17

Synthesis of 2-(3,4-dichlorophenyl)-N-methyl-1,2,3,4-tetrahydronaphthalen-1-amine (40a, 40b)

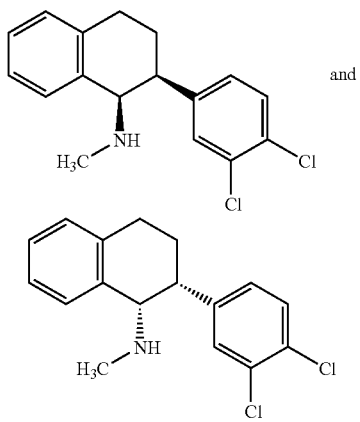

and 17.1. Synthesis of 2-(3,4-dichlorophenyl)-3,4-dihydronaphthalen-1(2H)-one (39)

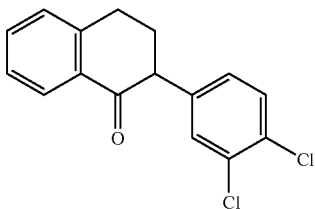

To a stirring solution of a-tetralone 38 (1.00 g, 6.84 mmol) and pd(dba)$_2$ (39 mg, 1 mol %) in toluene was added t-Bu$_3$P (228 uL, 10 wt % in hexanes, 1.1%). The solution was chilled (dry-ice bath) before adding LiHMDS (7.5mL, 1 M in hexanes, 1.1 eq) followed by 1-bromo-3,4-dichlorobenzene (1 mL, 1.1 eq). The solution was then allowed to warm to ambient temperature and heated under microwave radiation for 5 minutes (maximum temperature 140° C.). After cooling, the reaction was quenched with aqueous ammonium chloride and extracted with MTBE. The organic layer was dried with sodium sulfate, filtered through celite, and evaporated. The crude oil was separated on silic gel to give the title compound (1.46 g, 73%) as a white solid. TLC R$_f$ (25% EA/Hex)=0.26. GCMS R$_t$=13.82 min m/z=290 (M+). $^1$H NMR (CDCl$_3$, δ): 8.06 (dd, J=1.1, 7.8 Hz, 1H), 7.51 (td, J=1.4, 7.5 Hz, 1H), 7.40 (d, J=8.3 Hz, 1H), 7.33 (m, 2H), 7.29 (d, J=1.8 Hz, 1H), 7.03 (dd, J=2.1, 8.3 Hz, 1H), 3.7 (m, 1H), 3.2-3.0 (m, 2H), 2H). $^{13}$C NMR (CDCl$_3$, δ): 196.9, 143.7, 139.8, 133.7, 132.4, 132.3, 130.9, 130.5, 130.3, 128.8, 128.0, 127.8, 126.9, 53.6, 30.9, 28.9.

17.2. Synthesis of 2-(3,4-dichlorophenyl)-N-methyl-1,2,3,4-tetrahydronaphthalen-1-amine (40a, 40b)

To a solution of tetralone 39 (1.00 g, 3.43 mmol) in THF (25 mL) and methanol (40 mL) was added methylamine hydrochloride (2.4 g, 10 eq). The resultant mixture was stirred at 50° C. After dissolution (10 min), sodium borohydride (2.0 g, 15 eq) was added in 4 portions over 2 days. After cooling, the mixture was diluted with 5% NaOH and stirred for 1 hour. After evaporation, the crude residue was partitioned between MTBE and water and brine. The organic layer was evaporated to give the crude amine as a mixture of starting material, alcohol, and amine. The amine was purified by reverse-phase HPLC to give the title compound (0.33 g, 31%).

The enantiomers were separated using a Chiracel OD (98:2:0.1 Hex/IPA/DEA) column. Retention times for each isomer are summarized in Table 7, below.

TABLE 7

| Retention times for both cis-enantiomers [min] | | |
| --- | --- | --- |
|  | 40a | 40b |
|  | E1 | E2 |
|  | Cis | Cis |
| HPLC R$_t$ (Chiracel OD, 98:2:0.1 Hex/IPA/DEA) | 4.3 | 5.6 |

Cis-enantiomers 40a (E1) and 40b (E2): LCMS Rt=min m/z=306 (M+1). 1H NMR (CDCl$_3$, δ): 7.4 (m, 2H), 7.2 (m, 5H), 3.65 (d, J=3.5 Hz, 1H), 3.11 (dt, J=3.3, 12.2 Hz, 1H), 3.03 (ddd, J=2.3, 6.4, 17.3 Hz, 1H), 2.40 (ddd, J=6.5, 12.4, 23.8 Hz, 1H), 2.18 (s, 3H), 1.95 (sep, J=3.2 Hz, 1H), 0.92 (bs, 1H). $^{13}$C NMR(CDCl$_3$, δ): 144.2, 138.5, 135.9, 132.2, 130.2, 130.0, 129.4, 129.2, 127.5, 127.3, 125.4, 114.8, 62.7, 44.0, 36.0, 28.7, 22.6.

Example 18

Synthesis of cis-2-(3,4-dichlorophenyl)-N,N-dimethyl-1,2,3,4-tetrahydronaphthalen-1-amine (41)

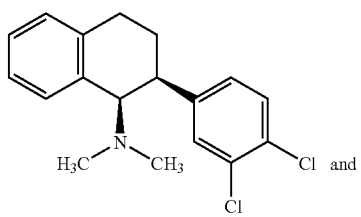

and

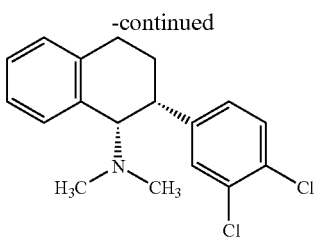

A solution of the respective methylamine 40 (e.g., 20-25 mg) in formic acid (e.g., 1 mL) and formaldehyde (e.g., 1 mL) was stirred at 100° C. for three hours. After chilling on ice, the solution was quenched with saturated aqueous sodium hydroxide (2mL) and extracted with MTBE. The solvent was removed and the residue was filtered through an aminopropyl cartridge to give the desired dimethylamine as a clear oil.

Cis-enantiomers 41a and 41b: LCMS $R_t$=10.33 min m/z=320 (M+1). $^1$H NMR (CDCl$_3$, δ): 7.4 (m, 2H), 7.2 (m, 5H), 3.8 (m, 1H), 3.0 (m, 3H), 2.4 (m, 1H), 1.97 (s, 6H), 1.9 (m, 1H). $^{13}$CNMR (CDCl$_3$, δ): 145.1, 136.4, 136.3, 131.5, 130.5, 130.4, 129.6, 129.5, 129.1, 128.0, 127.1, 125.0, 66.5, 45.9, 45.8, 29.0, 22.6.

Example 19

Synthesis of 1-((S)-4-(3,4-dichlorophenyl)-3,4-dihydronaphthalen-2-yl)-N-methylethanamine (47)

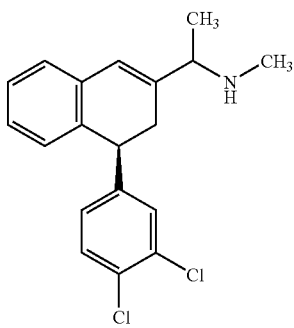

19.1. Synthesis of (S,E)-4-(3,4-dichloroplhenyl)-2-etliylidene-3,4-dihydronaphthalen-1(2H)-one (42)

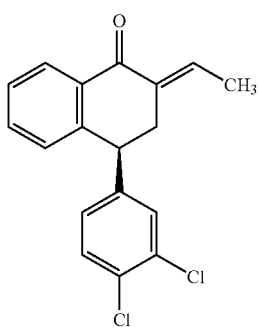

To a solution of (S)-4-(3,4-dichlorophenyl)-3,4-dihydronaphthalen-1 (2H)-one 1 (3.0 g, 10.3 mmol) in THF (50 mL) at −78 ° C was added LiHMDS (1.0 M, 12.4 mL, 12.4 mmol). The reaction mixture was stirred for 20 min before acetaldehyde (0.55 g, 0.70 mL, 12.41 mmol) was added. The reaction mixture was stirred and warmed to 0° C. over 2 h before being quenched with a saturated solution of NH$_4$Cl (10 mL). The product was extracted with ethyl acetate, dried and concentrated. The residue was purified by silica gel column chromatography (ethyl acetate/hexane=1:7 to 1:5) to give (S,E)-4-(3,4-dichlorophenyl)-2-ethylidene-3,4-dihydronaphthalen-1(2H)-one 42 (2.9 g, 88%).

19.2. Synthesis of (4S)-4-(3,4-dichlorophenyl)-2-(1-(methylamino)ethyl)-1,2,3,4tetrahydronaphthalen-1-ol (44)

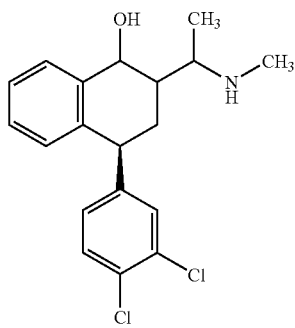

To a solution of 42 (0.80 g, 2.52 mmol) in THF (10 mL) at ambient temperature was added methylamine solution (2.0 M in THF, 3.78 mL, 7.56 mmol). The reaction mixture was stirred for 4 h before NaBH$_4$ (0.44 g, 11.49) was added. The reaction mixture was stirred for 3 h before being quenched by a saturated solution of NH$_4$Cl (10 mL). The product was extracted with diethyl ether, dried and concentrated. The residue was purified by silica gel column chromatography (ethyl acetate/hexane/0.1% DEA=1 :7 to 1:5) to give (4S)-4-(3,4-dichlorophenyl)-2-(1-(methylamino)ethyl)-1,2,3,4-tetrahydronaphthalen-1-ol (44) (493 mg, 56%).

19.3. Synthesis of 1-((S)-4-(3,4-dichlorophenyl)-3,4-dihydronaphthalen-2-yl)-N-methylethanamine (47)

To a solution of 44 (480 mg, 1.37 mmol) in CH$_2$Cl$_2$ (5 mL) was added TFA (5 mL). The reaction mixture was stirred for 2 h before being concentrated. The residue was subjected to chiral AD column chromatography (ethanol/MeOH/hexane/DEA=3:2:93:0.1) to give 47 as a single diastereomer. The absolute stereochemistry for the stereocenter in the side chain of 47 was not determined. A second stereoisomer was formed, but could not be isolated in pure form. $^1$H NMR (400 MHz, CDCl$_3$)δ 7.32 (d, J=8.0 Hz, 1 H), 7.25 (d, J=2.4 Hz, 1 H), 7.19 (d, J=7.2 Hz, 1 H), 7.15-7.07 (m, 2 H), 6.94 (dd, J=2.4, 8.4 Hz, 1H), 6.82 (d, J=7.2 Hz, 1 H), 6.47 (s, 1 H), 4.01 (t, J=8.4 Hz, 1 H), 3.64(q, J=6.4 Hz, 1 H), 2.71 (dd, J=7.6, 16.8 Hz, 1 H), 2.48 (dd, J=8.0, 16.8 Hz, 1 H), 2.09 (broad, 2 H), 1.16 (d, J=8.0 Hz, 3 H); 13C NMR (100 MHz, CDCl$_3$)δ 144.95, 143.12, 136.21, 134.01, 132.87, 130.42, 130.21, 128.02, 127.60, 127.62, 127.44, 126.78, 121.12, 52.47, 43.21, 32.58, 20.98; ESI MS m/z 318.0.

Example 20

Synthesis of 1-((S)-4-(3,4-dichlorophenyl)-3,4-dihydronaphthalen-2-yl)-N,N-dimethylethanamine (48)

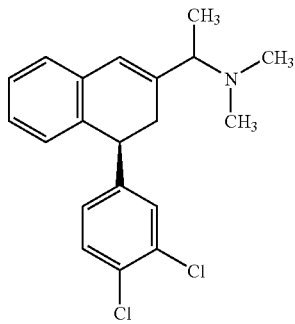

To a solution of 47 (200 mg, 0.60 mmol) in MeOH (5 mL) was added HCHO (35 mg, 37%, 1.20 mml), $HCO_2H$ (0.3 mL) and $NaB(CN)H_3$ (75 mg, 1.20 mmol). The reaction mixture was stirred for 20 min before being concentrated. The residue was dissolved in MeOH (2 mL) and subjected to reverse phase column chromatography ($CH_3CN/H_2O/0.1\%$ formic acid=5% to 100%) to give 48 (188 mg, 91%). $^1H$ NMR (400 MHz, $CDCl_3$) δ 7.34 (d, J=8.4 Hz, 1 H), 7.25 (m, 2 H), 7.20 (m, 2 H) 7.12 (m, 2 H), 7.0 (dd, J=2.0, 8.4 Hz, 1 H), 6.83 (d, J=7.6Hz, 1 H), 6.40 (s, 1 H), 4.10 (t, J=8.4 Hz, 1 H), 2.65 (d, t, J=6.4, 13.2 Hz, 1 H), 2.65 (dd, J=6.8, 16.4 Hz, 1 H), 2.54 (dd, J=9.2, 16.4 Hz, 1 H), 2.21 (s, 6 H), 1.01 (d, J=6.8 Hz, 1 H); $^{13}C$ NMR (100 m Hz, $CDCl_3$) δ 144.87, 142.04, 136.44, 134.67, 132.42, 130.61, 130.45, 128.16, 127.78, 127.53, 177.43, 126.61, 124.19, 124.12, 67.03, 43.72, 43.83, 43.50, 32.36, 16.45; ESI MS m/z 346.1

Example 21

Synthesis of 1-((S)-4-(3,4-dichlorophenyl)-3,4-dihydronaphthalen-2-yl)ethanamine (45)

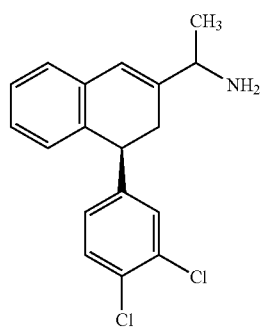

21.1. Synthesis of (4S)-2-(1-aminoethyl)-4-(3,4-dichlorophenyl)-1,2,3,4-tetrahydronaphthalen-1-ol (43)

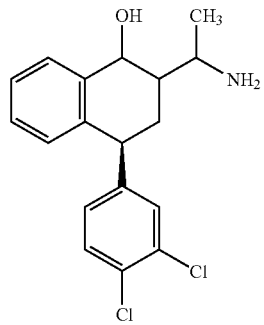

To a solution of (S,E)-4-(3,4-dichlorophenyl)-2-ethylidene-3,4-dihydronaphthalen-1(2H)-one (42) (0.60 g, 1.89 mmol) in THF (8 mL) at ambient temperature was added ammonia solution (2.0 M in MeOH, 2.83 mL, 5.67 mmol). The reaction mixture was stirred for 4 h before $NaBH_4$ (0.14 g, 3.78 mmol) was added. The reaction mixture was stirred for 2 h before being quenched by a saturated solution of $NH_4Cl$ (8 mL). The product was extracted with diethyl ether (30 mL×2), dried and concentrated. The residue was purified by silica gel column chromatography (ethyl acetate/hexane/ 0.1% DEA=1:7 to 1:5) to give (4S)-2-(1-aminoethyl)-4-(3,4-dichlorophenyl)-1,2,3,4-tetrahydronaphthalen-1-ol (43) (0.50 g, 50%).

21.2. Synthesis of 1-((S)-4-(3,4-dichlorophenyl)-3, 4-dihydronaphthalen-2-yl)ethanamine (45) as a diastereomeric mixture of 45 and 46

To a solution of 43 (400 mg, 1.19 mmol) in $CH_2Cl_2$ (5 mL) was added TFA (5 mL). The reaction mixture was stirred for 2 h before being concentrated. The residue was subjected to reverse phase column chromatography ($CH_3CN/H_2O/0.1\%$ Formic acid=5% to 100%) to give 1-((S)-4-(3,4-dichlorophenyl)-3,4-dihydronaphthalen-2-yl)ethanamine (0.31 g, 77.5%) as a mixture of two diastereomers (45 and 46).

21.3. Synthesis of tert-butyl 1-((S)-4-(3,4-dichlorophenyl)-3,4-dihydronaphthalen-2-yl)ethylcarbamate (49a, 49b)

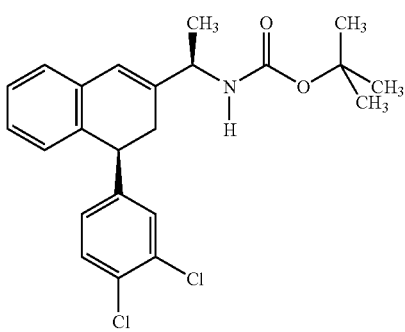

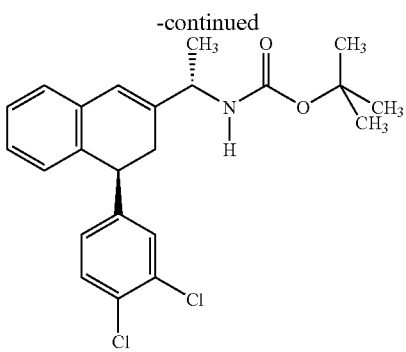

To a solution of the above mixture of (R)- and (S)-1-((S)-4-(3,4-dichlorophenyl)-3,4-dihydronaphthalen-2-yl)ethanamine (45, 46) (0.3 g, 0.94 mmoL) in CH₂Cl₂ (10 mL) was added Et₃N (140 mg, 0.20 mL, 1.42 mmol) and (BOC)₂O (250 mg, 1.13 mmol). The reaction mixture was stirred for 2 h at ambient temperature before being quenched by a saturated NH₄Cl solution (10.0 mL). The product was extracted with CH₂Cl₂ (2×15 mL). The combined extracts were washed with saturated brine, dried and concentrated. The resultant residue was purified by silica gel column chromatography (ethyl acetate/hexane=1:5) to give a mixture of tert-butyl 1-((S)-4-(3,4-dichlorophenyl)-3,4-dihydronaphthalen-2-yl)ethylcarbamate (339 mg, 86%). Diastereomers were separated using a chiral AD column (ethanol/methanol/hexane/DEA=3:2:95:0.1) to give 49a (fast moving diastereomer, 160 mg) and 49b (slow moving diastereomer, 120 mg) of tert-butyl-1-((S)-4-(3,4-dichlorophenyl)-3,4-dihydronaphthalen-2-yl)ethylcarbamate.

21.4. Synthesis of 1-((S)-4-(3,4-dichlorophenyl)-3,4-dihydronaphthalen-2-yl)ethanamine (45)

To a solution of tert-butyl-1-((S)-4-(3,4-dichlorophenyl)-3,4-dihydronaphthalen-2-yl)ethylcarbamate 49b (100 mg, 0.24 mmol) in CH₂Cl₂ (5 mL) was added TFA (5 mL). The reaction mixture was stirred for 2 h before being concentrated. The residue was subjected reverse phase column chromatography (CH₃CN/H₂O/0.1% Formic acid=5% to 100%) to give 1-((S)-4-(3,4-dichlorophenyl)-3,4-dihydronaphthalen-2-yl)ethanamine 45 (65 mg, 85%). ¹H NMR (400 MHz, CDCl₃) δ 7.33 (d, J=8.0 Hz, 1 H), 7.23 (d, J=2.4 Hz, 1 H), 7.19 (d, J=7.2 Hz, 1 H), 7.14-7.08 (m, 2 H), 6.98 (dd, J=2.4, 8.4 Hz, 1H), 6.82 (d, J=7.2 Hz, 1 H), 6.46 (s, 1 H), 4.08 (t, J=8.4 Hz, 1 H), 3.61 (q, J=6.4 Hz, 1 H), 2.69 (dd, J=7.6, 16.8 Hz, 1 H), 2.46 (dd, J=8.8, 16.8 Hz, 1 H), 2.10 (broad, 2 H), 1.14 (d, J=8.0 Hz, 3 H); ¹³C NMR (100 MHz, CDCl₃) δ 144.75, 143.04, 136.16, 134.41, 132.52, 130.53, 130.41, 127.96, 127.80, 127.62, 127.52, 126.80, 121.07, 52.17, 43.68, 32.41, 21.53; ESI MS m/z 318.0.

Example 22

Synthesis of 1-((S)-4-(3,4-dichlorophenyl)-3,4-dihydronaphthalen-2-yl)ethanamine (46)

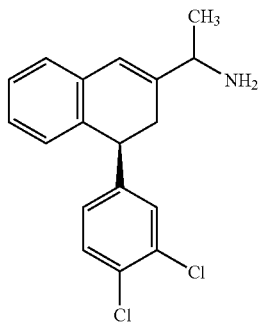

To a solution of tert-butyl-1-((S)-4-(3,4-dichlorophenyl)-3,4-dihydronaphthalen-2-yl)ethylcarbamate 49a (Example 21.3) (100 mg, 0.24 mmol) in CH₂Cl₂ (2 mL) was added TFA (2 mL). The reaction mixture was stirred for 1 h before being concentrated. The residue was subjected to reverse phase column chromatography (CH₃CN/H₂O/0.1% formic acid=5% to 100%) to give 46 (66 mg, 86%). ¹HNMR (400 MHz, CDCl₃) δ 7.34 (d, J=8.4 Hz, 1 H), 7.26 (d, J=2.0 Hz, 1 H), 7.20 (m, 1 H), 7.16-7.08 (m, 2 H), 7.01 (dd, J=1.6, 8.0 Hz, 1H), 6.80 (d, J=7.2 Hz, 1H), 6.46 (s, 1H), 4.09 (t, J=7.6 Hz, 1H), 3.59 (q, J=6.0 Hz, 1 H), 2.60 (dd, J=6.8, 16.4 Hz, 1 H), 2.53 (dd, J=8.4, 16.4 Hz, 1 H), 1.38 (broad, 2 H), 1.14 (d, J=6.8 Hz, 3 H); ¹³CNMR (100 MHz, CDCl₃) δ 144.81, 144.36, 136.15, 134.67, 132.51, 130.52, 130.41, 127.98, 127.77, 127.60, 127.34, 126.70, 120.93, 120.90, 51.91, 43.77, 32.86, 22.11; ESI MS m/z 318.0.

Example 23

Synthesis of 1-((2S,4S)-4-(3,4-dichlorophenyl)-1,2,3,4-tetrahydronaphthalen-2-yl)ethanamine (51)

23.1. Synthesis of tert-butyl 1-((2S,4S)-4-(3,4-dichlorophenyl)-1,2,3,4-tetrahydronaphthalen-2-yl)ethylcarbamate (50b)

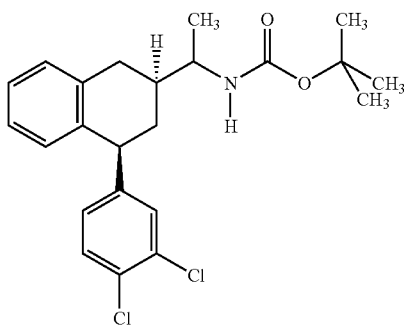

To a solution of tert-butyl-1-((S)-4-(3,4-dichlorophenyl)-3,4-dihydronaphthalen-2-yl)ethylcarbamate 49b (Example 21.3) (60 mg, 0.14 mmol) in ethyl acetate (6 mL) was added palladium on charcoal (30 mg, 5%). The mixture was then stirred under hydrogen (1 atm) for 1 h. The catalyst was removed through a pad of Celite. The filtrate was concentrated. Chiral AD column separation (ethanol/methanol/hexane/DEA=3:2:95:0.1) afforded tert-butyl 1-((2S,4S)-4-(3,4-dichlorophenyl)-1,2,3,4-tetrahydronaphthalen-2-yl)ethylcarbamate (36 mg, 60%).

23.2. Synthesis of 1-((2S,4S)-4-(3,4-dichlorophenyl)-1,2,3,4-tetrahydronaphthalen-2-yl)ethanamine (51)

To a solution of the above tert-butyl 1-((2S,4S)-4-(3,4-dichlorophenyl)-1,2,3,4-tetrahydronaphthalen-2-yl)ethylcarbamate 50b (50 mg, 0.12 mmol) in CH₂Cl₂ (3 mL) was added TFA (2 mL). The reaction mixture was stirred for 1 h before being concentrated. The residue was subjected to reverse phase column chromatography (CH₃CN/H₂O/0.1% formic acid=5% to 100%) to give 51 (34 mg, 90%). ¹HNMR (400 MHz, CDCl₃) δ 7.36 (d, J=8.0 Hz, 1 H), 7.26 (d, J=2.0 Hz, 1 H), 7.12 (m, 2 H), 7.03 (m, 1 H), 7.00 (dd, J=1.6, 8.0 Hz, 1 H), 6.71 (d, J=8.0 Hz, 1 H), 4.04 (dd, J=5.2, 12.0 Hz, 1 H), 2.92 (m, 2 H), 2.72 (dd, J=12.4, 16.0 Hz, 1 H), 2.22 (m, 2 H), 1.85 (m, 1 H), 1.48 (q, J=12.0 Hz, 1H), 1.20 (d, J=6.0 Hz, 3 H); ¹³CNMR (100 MHz, CDCl₃) δ 147.45, 138.65, 136.88, 132.65, 130.87, 130.69, 130.46, 129.54, 129.43, 128.43, 126.02, 126.26, 77.45, 51.35, 40.70, 41.77, 37.10, 32.94, 20.25; ESI MS m/z 320.0.

Example 24

Synthesis of 1-((2S,4S)-4-(3,4-dichlorophenyl)-1,2,3,4-tetrahydronaphthalen-2-yl)-N,N-dimethylethanamine (53)

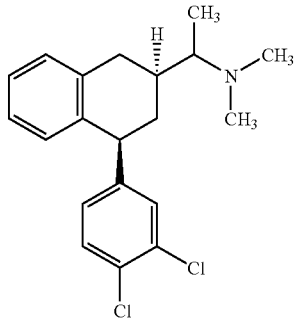

To a solution of 51 (20 mg, 0.063 mmol) in MeOH (4 mL) was added HCHO (7.5 mg, 37%, 0.25 mml), HCO$_2$H (0.10 mL) and NaB(CN)H$_3$ (19.6 mg, 0.31 mmol). The reaction mixture was stirred for 20 min before being concentrated. The residue was dissolved in MeOH (1 mL) and subjected to reverse phase column chromatography (CH$_3$CN/H$_2$O/0.1% formic acid=5% to 100%) to give 53 (18 mg, 85%). $^1$H NMR (400 MHz, CDCl$_3$) δ 7.34 (d, J=8.4 Hz, 1 H), 7.26 (d, J=2.0 Hz, 1 H), 7.12 (m, 2 H), 7.04 (m, 1 H), 7.00 (dd, J=2.0, 8.4 Hz, 1 H), 6.73 (d, J=7.6 Hz, 1 H), 4.02 (dd, J=5.6, 12.4 Hz, 1 H), 2.90 (m, 1 H), 2.45 (m, 1 H), 2.35 (m, 1 H), 2.56 (s, 6 H), 2.0 (m, 1 H), 1.42 (q, J=12.0 Hz, 1 H), 1.01 (d, J=6.8 Hz, 1 H); $^{13}$C NMR (100 MHz, CDCl$_3$) δ 147.77, 139.09, 137.36, 132.50, 130.96, 130.55, 130.23, 129.56, 129.49, 128.49, 126.47, 126.18, 64.10, 46.94, 41.30, 38.71, 38.16, 37.74, 9.19; ESI MS m/z 348.2.

Example 25

Synthesis of 1-((2S,4S)-4-(3,4-dichlorophenyl)-1,2,3,4-tetrahydronaphthalen-2-yl)ethanamine (52)

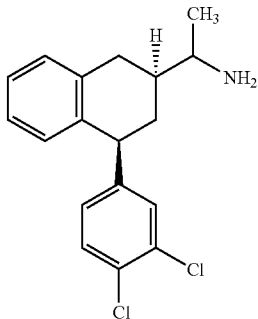

25.1. Synthesis of tert-butyl 1-((2S,4S)-4-(3,4-dichlorophenyl)-1,2,3,4-tetrahydronaphthalen-2-yl)ethylcarbamate (50a)

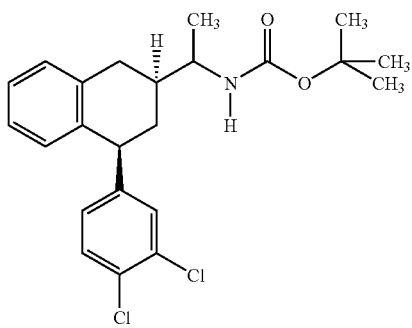

To a solution of tert-butyl (S)-1-((S)-4-(3,4-dichlorophenyl)-3,4-dihydronaphthalen-2-yl)ethylcarbamate 49a (Example 21.3) (60 mg, 0.14 mmol) in ethyl acetate (8 mL) was added palladium on charcoal (30 mg, 5%). The mixture was then stirred under hydrogen (1 atm) for 1 h. The catalyst was filtered off through a pad of Celite. The filtrate was concentrated. Chiral AD column separation (ethanol/methanol/hexane/DEA=3:2:95:0.1) afforded tert-butyl 1-((2S,4S)-4-(3,4-dichlorophenyl)-1,2,3,4-tetrahydronaphthalen-2-yl)ethylcarbamate (isomer 2) (40 mg, 67%).

25.2. Synthesis of (S)-1-((2S,4S)-4-(3,4-dichlorophenyl)-1,2,3,4-tetrahydronaphthalen-2-yl)ethanamine (52)

To a solution of the above tert-butyl 1-((2S,4S)-4-(3,4-dichlorophenyl)-1,2,3,4-tetrahydronaphthalen-2-yl)ethylcarbamate 50a (40 mg, 0.096 mmol) in CH$_2$Cl$_2$ (2 mL) was added TFA (2 mL). The reaction mixture was stirred for 1 h before being concentrated. The residue was subjected reverse phase column chromatography (CH$_3$CN/H$_2$O/0.1% Formic acid=5% to 100%) to give 52 (32.7 mg, 86%). $^1$H NMR (400 MHz, CDCl$_3$) δ 7.36 (d, J=8.0 Hz, 1 H), 7.27 (d, J=2.0 Hz, 1 H), 7.15 (m, 2 H), 7.02 (m, 2 H), 6.72 (d, J=7.6 Hz, 1 H), 4.04 (dd, J=5.2, 12.0 Hz, 1 H), 2.95 (m, 2 H), 2.78 (dd, J=12.0, 15.6 Hz, 1 H), 2.13 (m, 1 H), 1.80 (m, 1 H), 1.51 (q, J=12.4 Hz, 1 H), 1.35 (broad, 1 H), 1.14 (d, J=6.4 Hz, 3 H); $^{13}$CNMR (100 MHz, CDCl$_3$) δ 147.67, 138.79, 137.29, 132.64, 130.88, 130.68, 130.41, 129.57, 129.43, 128.43, 126.58, 126.15, 51.16, 46.91, 42.31, 37.48, 32.60, 21.20; ESI MS m/z 320.1.

Example 26

Synthesis of 1-((2S,4S)-4-(3,4-dichlorophenyl)-1,2,3,4-tetrahydronaphthalen-2-yl)-N,N-dimethylethanamine (54)

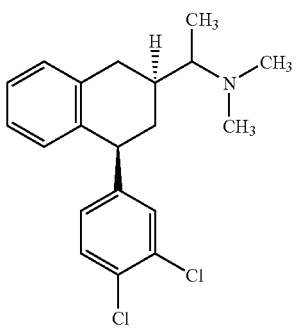

To a solution of 52 (20 mg, 0.063 mmol) in MeOH (3 mL) was added HCHO (7.5 mg, 37%, 0.25 mmol), HCO$_2$H (0.20 mL) and NaB(CN)H$_3$ (19.6 mg, 0.31 mmol). The reaction mixture was stirred for 10 min before being concentrated. The residue was dissolved in MeOH (1.5 mL) and subjected to reverse phase column chromatography (CH$_3$CN/H$_2$O/0.1% Formic acid=5% to 100%) to give 54 (17 mg, 86%). $^1$H NMR (400 MHz, CDCl$_3$) δ 7.37 (d, J=8.4 Hz, 1 H), 7.27 (d, J=6.0 Hz, 1 H), 7.19 (d, J=7.6 Hz, 1 H), 7.13 (d, J=1.2 Hz, 1 H), 7.02 (m, 2 H), 6.72 (d, J=7.6 Hz, 1 H), 4.05 (dd, J=5.2, 12.0 Hz, 1 H), 3.12 (m, 1 H), 2.65 (dd, J=11.6, 16.4 Hz, 1 H), 2.36 (m, 1 H), 2.18 (m, 1 H), 1.92 (m, 1 H), 1.42 (q, J=12.4 Hz, 1 H), 0.97 (d, J=6.4 Hz, 1 H); $^{13}$C NMR (100 MHz, CDCl$_3$) δ 147.79, 138.80, 137.82, 132.61, 130.91, 130.67, 129.57, 129.31, 128.43, 127.03, 126.54, 126.06, 63.90, 47.00, 40.96, 38.74, 38.24, 35.11, 8.90; ESI MS m/z 348.2.

Example 27

Synthesis of (4S,Z)-4-(3,4-dichlorophenyl)-2-methyl-3,4-dihydronaphthalen-1(2H)-one oxime (57 and 58)

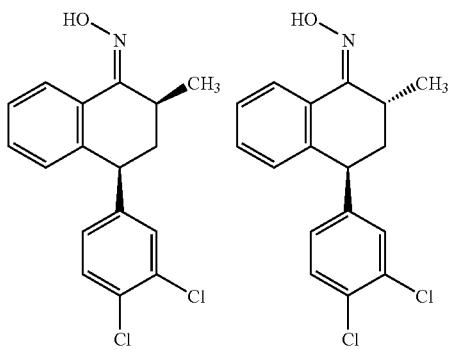

27.1. Synthesis of (4S)-4-(3,4-dichlorophenyl)-2-methyl-3,4-dihydronaphthalen-1(2H)-one (55)

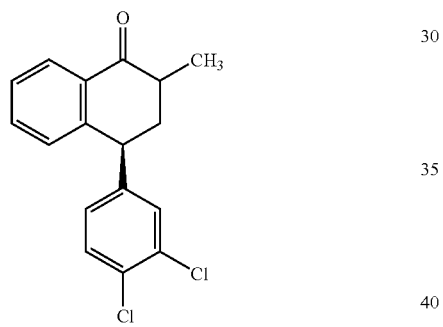

To a solution of (S)-4-(3,4-dichlorophenyl)-3,4-dihydronaphthalen-1(2H)-one (1) (2.0 g, 6.89 mmol) in THF (50 mL) at −78° C. was added LiHMDS (1.0 M in THF, 8.27 mL, 8.27 mmol). The reaction mixture was stirred for 20 min at −78° C. before MeI (1.17 g, 0.52 mL, 8.27 mmol) was added. The reaction mixture was stirred and warmed to 0° C. over 2 h before being quenched by a saturated solution of NH$_4$Cl (20 mL). The product was extracted with ethyl acetate (100 mL ×2), dried and concentrated. The residue was purified by silica gel column chromatography (ethyl acetate/hexane=1:7 to 1:5) to give (S)-4-(3,4-dichlorophenyl)-2,2-dimethyl-3,4-dihydronaphthalen-1(2H)-one (56) (0.33 g, 15%) and (4S)-4-(3,4-dichlorophenyl)-2-methyl-3,4-dihydronaphthalen-1 (2H)-one (55) (1.25 g, 60%).

27.2. Synthesis of (4S,Z)-4-(3,4-dichlorophenyl)-2-methyl-3,4-dihydronaphthalen-1 (2H)-one oxime (57 and 58)

To a solution of (4S)-4-(3,4-dichlorophenyl)-2-methyl-3, 4-dihydronaphthalen-1(2H)-one (55) (1.2 g, 3.92 mmol) in CH$_2$Cl$_2$ (30 mL) and MeOH (20 mL) was added NH$_2$OH.HCl (0.41 g, 5.92 mmol) and Et$_3$N (1.19 g, 11.84 mmol). The reaction mixture was heated at reflux. After 1 h, H$_2$O (10 mL0 was added and the resultant mixture was heated at reflux for 5 h before being concentrated. The residue was purified by silica gel column chromatography (ethyl acetatelhexane=1:7 to 1:5). Oxime 57, eluted from the column first (0.51 g, 41%) followed by the oxime 58 (0.49, 39%).

Isomer 57: $^1$H NMR (400 MHz, CDCl$_3$) δ 7.75 (dd, J=1.2, 7.6 Hz, 1 H), 7.44 (d, J=8.4 Hz, 1 H), 7.32 (d, J=2.0 Hz, 1 H), 7.26 (m, 2 H), 7.06 (dd, J=1.6, 8.0 Hz, 1 H), 6.40 (d, J=7.6 Hz, 1 H), 4.10 (dd, J=7.2, 14.0 Hz, 1 H), 3.45 (m, 1 H), 2.30 (m, 1 H), 1.75 (m, 1 H), 1.30 (d, J=6.8 Hz, 3 H); $^{13}$C NMR (100 MHz, CDCl$_3$) δ 159.59, 143.46, 142.69, 132.96, 131.56, 130.83, 129.61, 128.43, 127.44, 126.81, 125.78, 99.29, 44.01, 38.69, 30.51, 18.43; ESI MS m/z 320.2.

Isomer 58: $^1$HNMR (400 MHz, CDCl$_3$) δ 8.49 (s, 1 H), 7.97 (dd, J=2.0, 6.8 Hz, 1 H), 7.38 (d, J=8.0 Hz, 1 H), 7.30-7.20 (m, 3 H), 6.99 (dd, J=2.0, 8.4 Hz, 1 H), 6.80 (d, J=8.0 Hz, 1 H), 4.18 (dd, J=4.4, 11.6 Hz, 1 H), 3.74 (m, 1 H), 2.13 (d, t, J=4.8, 13.6 Hz, 1 H), 1.97 (d, t, J=4.4, 13.6 Hz, 1 H), 1.64 (s, 1 H), 1.30 (d, J=7.2 Hz, 1 H); $^{13}$C NMR (100 MHz, CDCl$_3$) δ 158.72, 145.87, 140.35, 132.83, 130.99, 130.85, 130.16, 129.74, 129.43, 128.40, 127.31, 124.87, 41.09, 38.51, 26.74, 15.85; ESI MS m/z 320.2.

Example 28

Synthesis of (4S)-4-(3,4-dichlorophenyl)-2,2-dimethyl-1,2,3,4-tetrahydronaphthalen-1-amine (59)

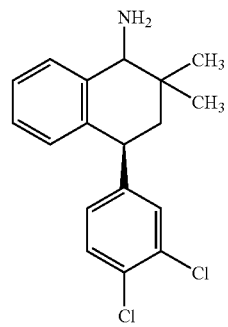

28.1. Synthesis of (S,Z)-4-(3,4-dichlorophenyl)-2,2-dimethyl-3,4-dihydronaphthalen-1(2H)-one oxime (60

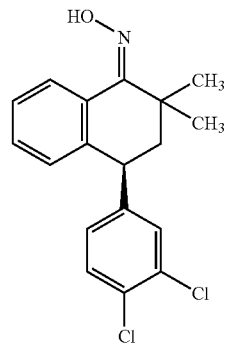

To a solution of (S)-4-(3,4-dichlorophenyl)-2,2-dimethyl-3,4-dihydronaphthalen-1(2H)-one (56) (0.8 g, 2.51 mmol) in CH$_2$Cl$_2$ (20 mL) and MeOH (15 mL)-H$_2$O (5 mL) was added NH$_2$OH.HCl (0.35 g, 5.04 mmol) and Et$_3$N (1.01 g, 10.1 mmol). The resultant mixture was heated at reflux for 5 h before being concentrated. The residue was purified by silica gel column chromatography (ethyl acetate/hexane=1:7 to 1:5) to give (S,Z)-4-(3,4-dichlorophenyl)-2,2-dimethyl-3,4-dihydronaphthalen-1 (2H)-one oxime (60) (0.72 g, 84%).

28.2. Synthesis of (1R,4S)-4-(3,4-dichlorophenyl)-2, 2-dimethyl-1,2,3,4-tetrahydronaphthalen-1-amine (59)

To a solution of 60 (30 mg, 0.089 mmol) in acetic acid (3 mL) was added palladium on charcoal (30 mg, 5%). The mixture was then stirred under hydrogen (1 atm) for 1 h. The catalyst was filtrated away through a pad of Celite. The filtrate was concentrated. The resultant residue was purified by chiral OJ column (ethanol/methanol/hexane/DEA=3:2:95:0.1) to give 59 (12.5 mg, 44%). $^1$H NMR (400 MHz, CDCl$_3$) δ 8.10 (d, J=8.0 Hz, 1 H), 7.44-7.38 (m, 2 H), 7.38-7.24 (m, 2 H), 6.81 (d, J=7.6 Hz, 1 H), 7.03 (dd, J=1.6, 8.0 Hz, 1 H), 4.28 (dd, J=4.4, 12.4 Hz, 1 H), 2.19 (dd, J=13.6, 12.4 Hz, 1 H), 2.06 (dd, J=13.6, 4.4 Hz, 1 H), 1.58 (s, 1 H), 1.27 (s, 6 H); $^{13}$C NMR (100 MHz, CDCl$_3$) δ 145.39, 144.92, 133.53, 133.01, 133.68, 131.19, 131.09, 131.01, 129.24, 128.51, 128.31

Example 29

Experimental Conditions for Monoamine Uptake Assays

The compounds of the invention were tested for their inhibition of functional uptake of 5-HT, NE, or DA, in synaptosomes prepared from rat whole brain, hypothalamus, or corpus striatum, respectively. Compounds were tested initially at 10 μM in duplicate, and if ≧50% inhibition of uptake was observed, they were tested further at 10 different concentrations in duplicate in order to obtain full inhibition curves. IC$_{50}$ values (concentration inhibiting control activity by 50%) were then determined by nonlinear regression analysis of the inhibition curves and tabulated below.

29.1. Serotonin Functional Uptake Assay forRat Reuptake Transporter

Quantification of 5-HT uptake was performed using synaptosomes isolated in a 0.32M sucrose buffer from a male Wistar rat cortex. The uptake of radiolabelled 5-HT by synaptosomes (100 μg of proteins/point) was allowed by incubating them in a well for 15 min at 37° C. in presence of test compounds and [$^3$H]5-hydroxytryptamine (serotonin; 0.1 μCi/point).

Synaptosomes and [$^3$H]serotonin were prepared in a Krebs buffer pH 7.4 containing 25 mM NaHCO$_3$, 11 mM glucose and 50 μM ascorbic acid. This incubation buffer was oxygenated during 5 minutes before incubation. Basal control was incubated for 15 minutes at 4° C. in order to avoid any uptake. Following this incubation the uptake was stopped by filtration through a unifilter 96-wells GFB Packard plate washed with Krebs buffer containing 25 mM NaHCO$_3$ in order to eliminate the free [$^3$H]serotonin. The radioactivity associated to the synaptosomes retained on the unifilter corresponding to the uptake was then measured with a microplate scintillation counter (Topcount, Packard) using a scintillation fluid. Non-specific binding was measured in the presence of an excess of cold, unlabeled ligand. Specific binding was obtained by subtracting nonspecific binding from total binding.

The reference compound was imipramine tested at 10 concentrations ranging from 10$^{-11}$ M to 10$^{-5}$ M in order to obtain an IC$_{50}$ value. See, Perovics and Müller, "Pharmacological profile of hypericum extract: effect on serotonin uptake by postsynaptic receptors," Arzeim. Forsch./Drug Res., 45:1145-1148 (1995).

29.2. Serotonin Functional Uptake Assay for Human Reuptake Transporter

Inhibition of human serotonin reuptake transporter was assayed using the recombinant human serotonin transporter expressed in HEK-293 cells using a published method (Gu H, Wall S, Rudnick G. Stable expression of biogenic amine transporters reveals differences in inhibitor sensitivity, kinetics, and ion dependence. J Biol Chem. 269 (10): 7124-7130, 1994)). HEK-293 cells expressing human serotonin transporter were plated before the assay. Test compound and/or vehicle was preincubated with cells in modified HEPES buffer pH 7.1 or pH 7.4 for 20 minutes at 18 to 25° C. and 65 nM [$^3$H]serotonin was then added for an additional timed incubation period (ten to thirty minutes). Cells with internalized [$^3$H]serotonin were washed and the amount of tritium taken into cells is counted using a liquid scintillation counter to determine [$^3$H]serotonin uptake. Non-specific binding of tritium was measured in a control reaction containing 10 μM fluoxetine, and was subtracted from the counts for assays to correct for non-specific binding of tritium. Reduction of [$^3$H]serotonin uptake by 50 percent or more (≧50%) relative to an uninhibited control reaction indicates significant inhibitory activity. Compounds were screened at 10, 1, 0.1, 0.01 and 0.001 μM. The reference compound for the assay was fluoxetine, for which the IC$_{50}$ value of 7.1 nM was obtained in a typical experiment.

29.3. Dopamine Functional Uptake Assay for Rat Reuptake Transporter

Quantification of dopamine uptake was performed using synaptosomes isolated in a 0.32 M sucrose buffer from a male Wistar rat striatum. The uptake of radiolabelled dopamine by synaptosomes (20 μg of proteins/point) was allowed by incubating them for 15 minutes at 37° C. in the presence of test compounds and [$^3$H]-dopamine (0.1 μCi/point). The experiment was performed in a deep well.

Synaptosomes and [$^3$H]-dopamine were prepared in a Krebs buffer pH 7.4 containing 25 mM NaHCO$_3$, 11 mM glucose and 50 μM ascorbic acid. This incubation buffer was oxygenated for 5 minutes before incubation. Basal control was incubated for 15 minutes at 4° C. in order to avoid any uptake. Following this incubation, the uptake was stopped by filtration through a unifilter 96-wells GFB Packard plate washed with Krebs buffer containing 25 mM NaHCO$_3$ in order to eliminate free [$^3$H]-dopamine. The radioactivity associated to the synaptosomes retained onto the unifilter corresponding to the uptake was then measured with a microplate scintillation counter (Topcount, Packard) using a scintillation fluid.

The reference compound was GRB12909 tested at 8 concentrations ranging from 10$^{-11}$ M to 10$^{-6}$ M in order to obtain an IC$_{50}$ value. See, Jankowsky et al., "Characterization of sodium-dependent [$^3$H]GBR-12935 binding in brain: a radioligand for selective labeling of the dopamine transport complex," J Neurochem, 46:1272-1276 (1986).

29.4. Dopamine Functional Uptake Assay for Human Reuptake Transporter

Inhibition of human dopamine reuptake transporter was assayed using the recombinant human dopamine transporter expressed in CHO-K1 or HEK293 cells using a published method (Pristupa, Z. B., Wilson, J. M., Hoffman, B. J., Kish, S. J. and Niznik, H. B. Pharmacological heterogeneity of the cloned and native human dopamine transporter: disassociation of [$^3$H]GBR12,935 binding. Mol. Pharmacol. 45: 125-135, 1994). Either CHO-K1 or HEK293 cells expressing human recombinant dopamine transporter were plated before the assay. Test compound and/or vehicle was preincubated with cells in modified HEPES buffer pH 7.1 or pH 7.4 for 20 minutes at 18 to 25° C. and 50 nM [$^3$H]dopamine was then added for an additional timed incubation period (10 to 30 minutes). After washing the cells to remove [$^3$H]dopamine not internalized, the cells were lysed, and the amount of tritium in the lysate was measured using a liquid scintillation counter to determine [$^3$H]dopamine uptake. Non-specific binding of tritium was measured in a control reaction containing 10 μM nomifensine, and was subtracted from the counts for assays to correct for non-specific binding of tritium. Reduction of [$^3$H]dopamine uptake by 50 percent or more ($\geqq$50%) relative to an uninhibited control reaction indicates significant inhibitory activity. Compounds were screened at 10, 1, 0.1, 0.01 and 0.001 μM. The reference compound for the assay was nomifensine, for which the IC$_{50}$ value of 11 nM was obtained in a typical experiment.

29.5. Norepinephrine Functional Uptake Assay for Rat Reuptake Transporter

Quantification of norepinephrine uptake was performed using synaptosomes isolated in a 0.32 M sucrose buffer from a male Wistar rat hypothalamus. The uptake of radiolabelled norepinephrine by synaptosomes (100 μg of proteins/point) was allowed by incubating them for 20 minutes at 37° C. in presence of test compounds and [$^3$H]-norepinephrine (0.1 μCi/point). The experiment was performed in a deep well.

Synaptosomes and [$^3$H]-norepinephrine were prepared in a Krebs buffer pH 7.4 containing 25 mM NaHCO$_3$, 11 mM glucose and 50 μM ascorbic acid. This incubation buffer was oxygenated for 5 minutes before incubation. Basal control was incubated for 20 minutes at 4° C. in order to avoid any uptake. Following this incubation, the uptake was stopped by filtration through a unifilter 96-wells GFB Packard plate washed with Krebs buffer containing 25 mM NaHCO$_3$ in order to eliminate the free [$^3$H]-norepinephrine. The radioactivity associated to the synaptosomes retained onto the unifilter corresponding to the uptake was then measured with a microplate scintillation counter (Topcount, Packard) using a scintillation fluid.

The reference compound is protriptyline tested at 13 concentrations ranging from 10$^{-11}$ M to 10$^{-5}$ M in order to obtain an IC$_{50}$ value. See, Perovics and Muller, "Pharmacological profile of hypericum extract: effect on serotonin uptake by postsynaptic receptors," *Arzeim. Forsch./Drug Res.*, 45:1145-1148 (1995).

29.6. Norepinephrine Functional Uptake Assay for Human Reuptake Transporter

Inhibition of human norepinenbrine reuptake transporter was assayed using the recombinant human norepinephrine transporter expressed in either HEK293 or MDCK cells using a published method (Galli A, DeFelice L J, Duke B J, Moore K R, Blakely R D. Sodium dependent norepinephrine-induced currents in norepinephrine-transporter-transfected HEK-293 cells blocked by cocaine and antidepressants. *J Exp. Biol.* 198: 2197-2212, 1995). The cells were plated before the assay. Test compound and/or vehicle was preincubated with cells in modified HEPES buffer pH 7.1 or pH 7.4 for 20 minutes at 18 to 25° C. . Following the preincubation, 25 nM [$^3$H]norepinephrine was added for an additional timed incubation period (10 to 20 minutes). After the cells were washed to remove [$^3$H]norepinephrine not internalized, the cells were lysed, and the amount of tritium in the cell lysate was measured using a liquid scintillation counter to determine [$^3$H]norepinephrine uptake. Non-specific binding of tritium was measured in a control reaction containing 10 μM imipramine (or 10 μM nisoxetine), and was subtracted from the counts for assays to correct for non-specific binding of tritium. Reduction of [$^3$H]norepinephrine uptake by 50 percent or more ($\geqq$50%) relative to an uninhibited control reaction indicates significant inhibitory activity. Compounds were screened at 10, 1, 0.1, 0.01 and 0.001 μM. The reference compounds for the assay were desipramine and nisoxetine, for which IC$_{50}$ values of 1.9 nM and 5.3 nM respectively were obtained in typical experiments.

29.7. Results

The results for the monoamine uptake assays are summarized in Table 6, below:

TABLE 6

In vitro Results for Monoamine Uptake Assays

| Compound No. | Human IC$_{50}$ (nM) SERT | NET | DAT |
|---|---|---|---|
| 6a | 46 | 124 | 350 |
| 6b | 1830 | 731 | 408 |
| 6c | 84 | 855 | 894 |
| 6d | 108 | 174 | 175 |
| 7a | 6 | 27 | 114 |
| 7b | 125 | 117 | 62 |
| 7c | 8 | 45 | 281 |
| 7d | 107 | 73 | 72 |
| 8a | 7 | 167 | 454 |
| 8b | 108 | 174 | 176 |
| 8c | 3 | 164 | 273 |
| 8d | 20 | 98 | 319 |
| 14a | 2 | 28 | 11 |
| 14b | 19 | 257 | 111 |
| 14c | 1 | 92 | 45 |
| 14d | 61 | 371 | 92 |
| 15a | 9 | 72 | 125 |
| 15b | 54 | 126 | 103 |
| 15c | 23 | 210 | 111 |
| 15d | 16 | 372 | 484 |
| 16a mixture of cis-enantiomers | 311 | 565 | 332 |
| 16b mixture of trans-enantiomers | 970 | 309 | 339 |
| 23a | 117 | 710 | 371 |
| 23b | 1300 | 48 | 67 |
| 23c | 2360 | 36 | 21 |
| 23d | 48 | 65 | 48 |
| 25a | 1 | 26 | 32 |
| 25b | 79 | 158 | 50 |
| 32a.1 | 162 | 1210 | 1080 |
| 32a.2 | 130 | 467 | 415 |
| 32a.3 | 4380 | 1050 | 1500 |
| 32a.4 | 958 | 786 | 1680 |
| 32b.1 | 359 | 2328 | 83 |
| 32b.2 | 307 | 2315 | 496 |
| 32c.1 | 68 | 571 | 18 |
| 32c.2 | 29 | 112 | 109 |
| 32c.3 | 105 | 198 | 92 |
| 32c.4 | 209 | 111 | 78 |
| 33a.1 | 475 | 2310 | 781 |
| 33a.2 | 156 | 2260 | 396 |

TABLE 6-continued

In vitro Results for Monoamine Uptake Assays

| Compound No. | SERT | Human IC$_{50}$ (nM) NET | DAT |
|---|---|---|---|
| 33a.3 | 207 | 1170 | 2290 |
| 33a.4 | 808 | 1700 | 1410 |
| 33c.1 | 24 | 943 | 194 |
| 33c.2 | 8 | 684 | 67 |
| 33c.3 | 616 | 906 | 83 |
| 33c.4 | 92 | 1899 | 224 |
| 36a | 1090 | 3454 | 511 |
| 36b | 2521 | 7087 | 1603 |
| 36c | 26 | 745 | 88 |
| 36d | 868 | 1615 | 204 |
| 37a | 355 | 2379 | 235 |
| 37b | 742 | 499 | 106 |
| 37c | 70 | 1186 | 284 |
| 37d | 3153 | 1005 | 36 |
| 40a | 2468 | >10,000 | 3407 |
| 40b | 7725 | >10,000 | 1792 |
| 41a | 3165 | >10,000 | 2276 |
| 41b | 9737 | >10,000 | 1124 |
| 45 | 876 | 53 | 174 |
| 46 | 50 | 580 | 1660 |
| 47 | 44 | 1180 | 1140 |
| 48 | 134 | 2720 | 2440 |
| 51 | 2 | 12 | 30 |
| 52 | 8 | 122 | 622 |
| 53 | 58 | 399 | 495 |
| 54 | 815 | 1700 | 1900 |
| 57 | 3180 | 3890 | 997 |
| 58 | 1700 | 2840 | 436 |
| 59 | 5502 | >10000 | 1083 |

In Table 6, compound numbers correspond to those used in the Schemes and Examples above. In addition, the following abbreviations have been used in Table I: SERT, serotonin transporter; NET, norepinephrine transporter; and DAT, dopamine transporter.

These results indicate that compounds of the invention exhibit potent inhibition on the neuronal uptake of NE, DA, and/or 5-HT, and compare favorably with potencies seen for various existing therapeutic agents. For example, reported potencies (IC$_{50}$ or K$_i$ values) of approved and launched drugs include: fluoxetine (PROZAC®), 7 nM for inhibition of human 5-HT reuptake transporter; methylphenidate (RITALIN®), 193 nM and 38 nM for inhibition of human dopamine and norepinephrine reuptake transporters respectively; amitriptyline (ELAVIL®), 13 and 3 nM for inhibition of the human norepinephrine and serotonin reuptake transporters respectively, and venlafaxine (EFFEXOR®, a so-called serotonin norepinephrine reuptake inhibitor, or SNRI) 145 and 1420 nM, for inhibition of the human serotonin, and norepinephrine reuptake transporters respectively. The multiple inhibition of the neuronal uptake of NE, DA and/or 5-HT displayed by the compounds of the invention provides the clinician with the ability to more effectively treat CNS disorders, including without limitation affective disorders, cerebral function disorders, anxiety disorders, neuropathic pain, and migraine or migraine headache, by elevating various monoamine levels in the brain simultaneously and over the same dose-range without the need to titrate separate drugs.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

What is claimed is:

1. A compound having a structure, which is selected from Formula (II), Formula (III), and Formula (IV), or a pharmaceutically acceptable salt thereof:

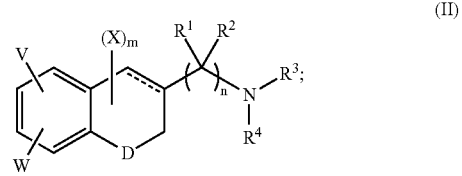

(II)

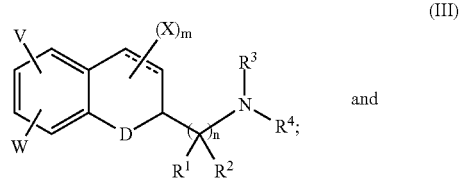

(III)

and

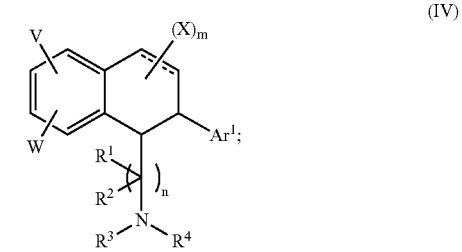

(IV)

wherein n is an integer selected from 0 to 2;

D is CX—Ar$^1$;

m is an integer selected from 0 to 6;

each X is independently selected from H, halogen, CN, OR$^5$, SR$^5$, S(O)$_2$R$^5$, NR$^6$R$^7$, NR$^6$S(O)$_2$R$^5$, NR$^6$C(O)R$^5$, acyl, =X$^1$, substituted or unsubstituted alkyl except CF$_3$, substituted or unsubstituted heteroalkyl, substituted or unsubstituted aryl, substituted or unsubstituted heteroaryl, and substituted or unsubstituted heterocycloalkyl, wherein X$^1$ is selected from O, S, and NOR$^{5'}$ wherein R$^{5'}$ is selected from H, substituted or unsubstituted alkyl, and substituted or unsubstituted heteroalkyl;

each R$^5$, R$^6$ and R$^7$ is independently selected from H, acyl, substituted or unsubstituted alkyl, substituted or unsubstituted heteroalkyl, substituted or unsubstituted aryl, and substituted or unsubstituted heteroaryl, wherein two of R$^5$, R$^6$ and R$^7$, together with the atoms to which they are attached, are optionally joined to form a 3- to 7-membered ring;

Ar¹ is

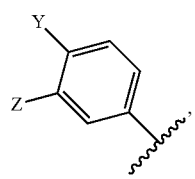

wherein
Y and Z are each independently Cl, CF₃, or CN;
V and W are independently selected from H, halogen, CF₃, CN, OR⁹, SR⁹, S(O)₂R⁹, NR¹⁰R¹¹, NR¹⁰S(O)₂R⁹, NR¹⁰C(O)R⁹, acyl, substituted or unsubstituted alkyl, substituted or unsubstituted heteroalkyl, substituted or unsubstituted aryl, substituted or unsubstituted heteroaryl, and substituted or unsubstituted heterocycloalkyl, or
V and W, together with the atoms to which they are attached, are joined to form a 5- to 7-membered ring;
wherein each R⁹, R¹⁰, and R¹¹ is independently selected from H, substituted or unsubstituted alkyl, substituted or unsubstituted heteroalkyl, substituted or unsubstituted aryl, substituted or unsubstituted heteroaryl, and substituted or unsubstituted heterocycloalkyl;
wherein any two of R⁹, R¹⁰, and R¹¹, together with the atoms to which they are attached, are optionally joined to form a 3- to 7-membered ring;
each R¹ and R² is independently selected from H, halogen, CN, CF₃, OR¹², substituted or unsubstituted alkyl, substituted or unsubstituted heteroalkyl, substituted or unsubstituted aryl, substituted or unsubstituted heteroaryl, and substituted or unsubstituted heterocycloalkyl,
wherein
R¹² is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl;
R³ and R⁴ are independently selected from H, OR¹³, acyl, S(O)₂R¹⁴, substituted or unsubstituted alkyl, substituted or unsubstituted heteroalkyl, substituted or unsubstituted aryl, substituted or unsubstituted heteroaryl, and substituted or unsubstituted heterocycloalkyl,
wherein
R¹³ is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl;
R¹⁴ is selected from substituted or unsubstituted alkyl, substituted or unsubstituted heteroalkyl, substituted or unsubstituted aryl, substituted or unsubstituted heteroaryl, and substituted or unsubstituted heterocycloalkyl; and
wherein at least two of R¹, R², R³ and R⁴, together with the atoms to which they are attached, are optionally joined to form a 3- to 7-membered ring,
and any enantiomer, diastereoisomer, racemic mixture, enantiomerically enriched mixture, and enantiomerically pure form thereof 2. The compound of claim 1, wherein said compound is chiral.

3. The compound of claim 1, having a structure, which is selected from:

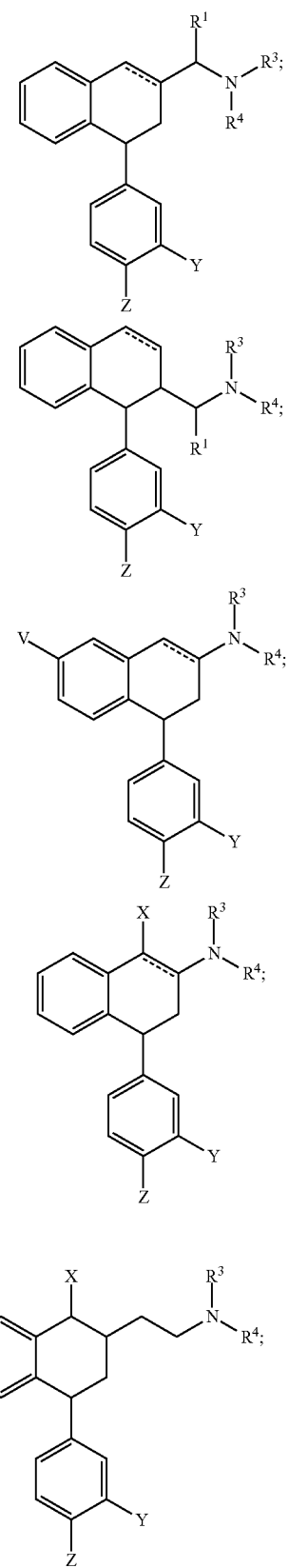

and

-continued

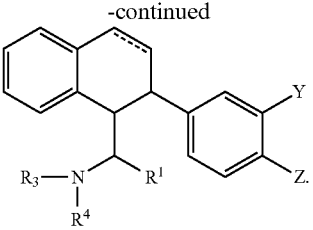

4. A composition comprising a first stereoisomer and at least one additional stereoisomer of a compound of claim 1, wherein said first stereoisomer is present in a diastereomeric excess of at least 80% relative to said at least one additional stereoisomer.

5. A pharmaceutical composition comprising a compound of claim 1, or a pharmaceutically acceptable salt thereof, and a pharmaceutically acceptable carrier, vehicle or diluent.

6. A method for treating a central nervous system disorder, said method comprising administering to a subject in need thereof a therapeutically effective amount of a compound of claim 1, or a pharmaceutically acceptable salt thereof.

7. The method of claim 6, wherein said central nervous system disorder is selected from depression, fibromyalgia, pain, sleep apnea, attention deficit disorder (ADD), attention deficit hyperactivity disorder (ADHD), restless leg syndrome, schizophrenia, anxiety, obsessive compulsive disorder, post-traumatic stress disorder, seasonal affective disorder (SAD), premenstrual dysphoria, and a neurodegenerative disease.

8. The method of claim 6, wherein said central nervous system disorder is Parkinson's disease.

9. The method of claim 6, wherein said central nervous system disorder is neuropathic pain.

10. A method of inhibiting reuptake of one or more monoamines from the synaptic cleft, said method comprising administering to a mammalian subject a compound of claim 1, or a pharmaceutically acceptable salt thereof.

11. The method of claim 10, wherein said monoamine is selected from serotonin, dopamine, and norepinephrine, or any combination thereof.

12. A method of modulating one or more monoamine transporters, said method comprising administering to a mammalian subject a compound of claim 1, or a pharmaceutically acceptable salt thereof 13. The method of claim 12, wherein said monoamine transporter is selected from serotonin transporter (SERT), dopamine transporter (DAT), and norepinephrine transporter (NET), or any combination thereof 14. The compound of claim 1, wherein Y and Z are both Cl.

15. The compound of claim 14, wherein $R^3$ and $R^4$ are independently H or substituted or unsubstituted $C_1$-$C_4$ alkyl.

16. The compound of claim 14, wherein m is 1, and X is H or $OR^5$.

17. The compound of claim 14, wherein m is 1, X is H or $OR^5$, and $R^3$ and $R^4$ are independently H or substituted or unsubstituted $C_1$-$C_4$ alkyl.

18. The compound of claim 17, wherein $R^5$ is H.

19. The compound of claim 1, or a pharmaceutically acceptable salt thereof, wherein the compound is:

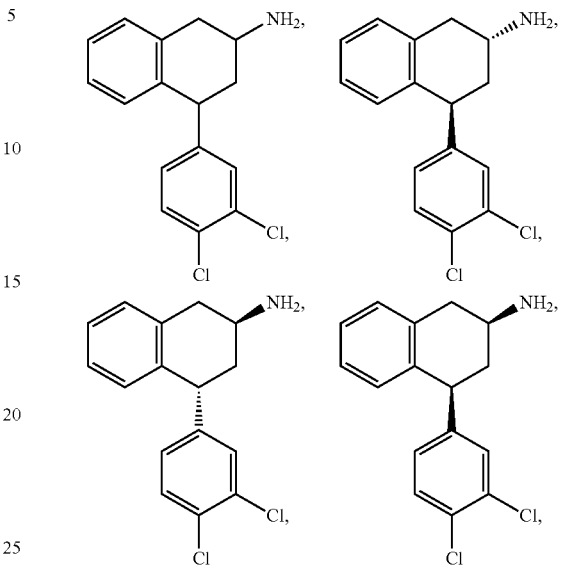

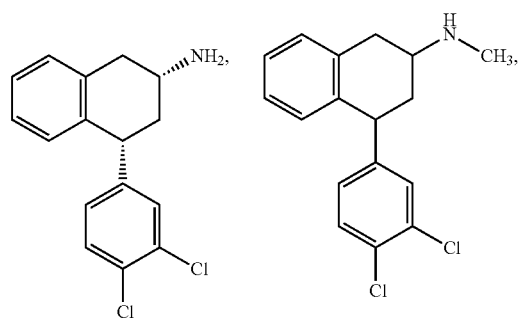

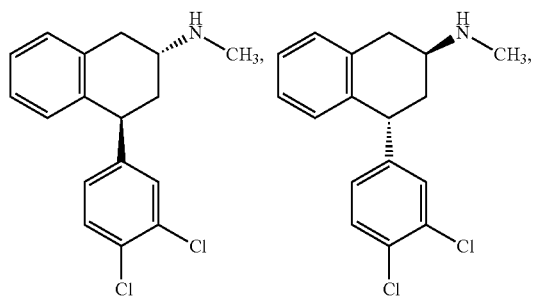

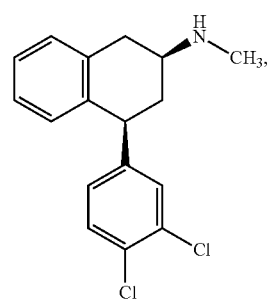

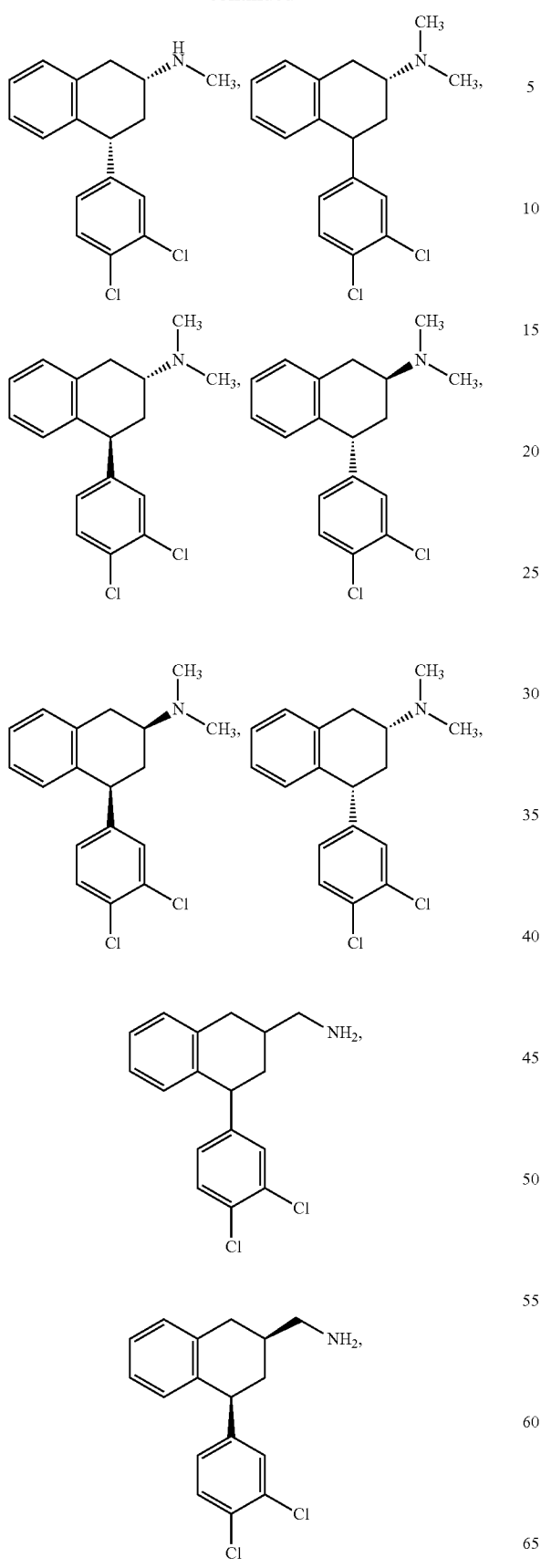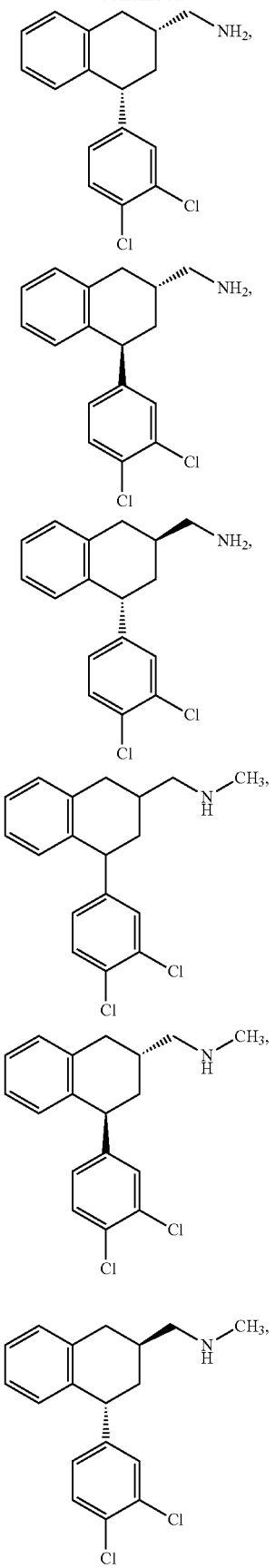

89
-continued
90
-continued
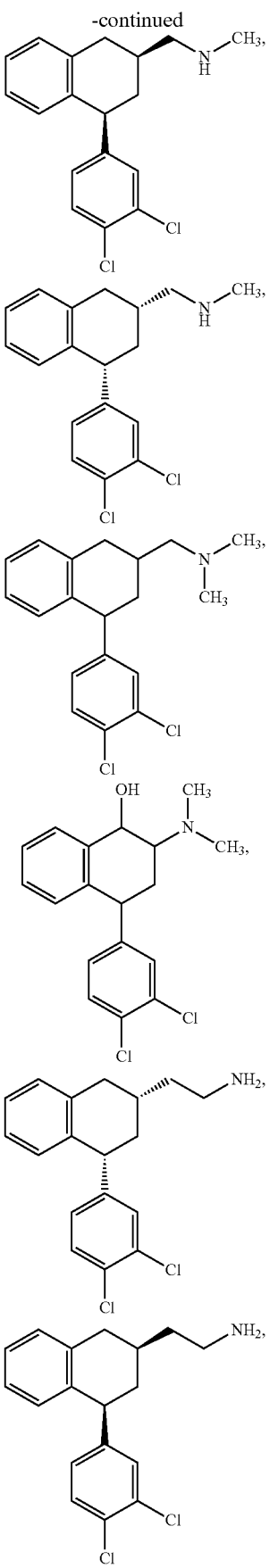
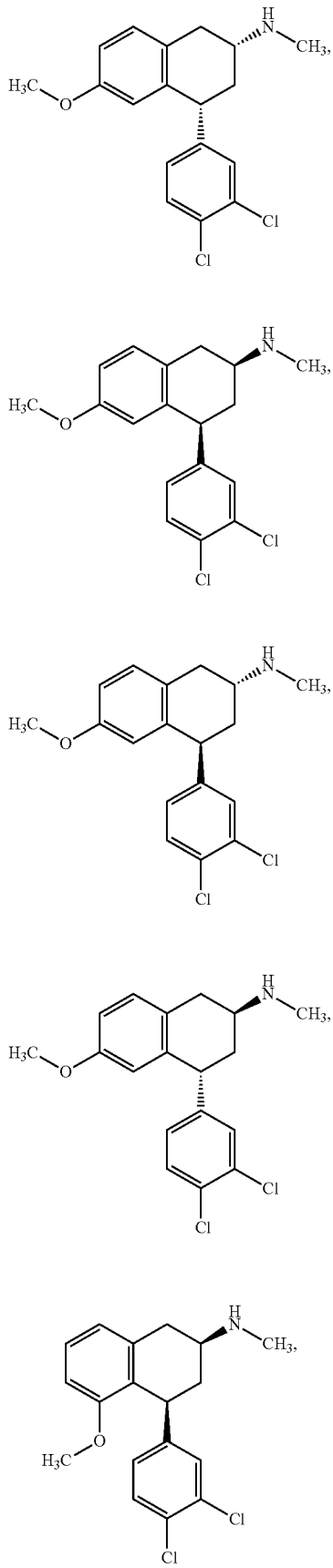

91
-continued
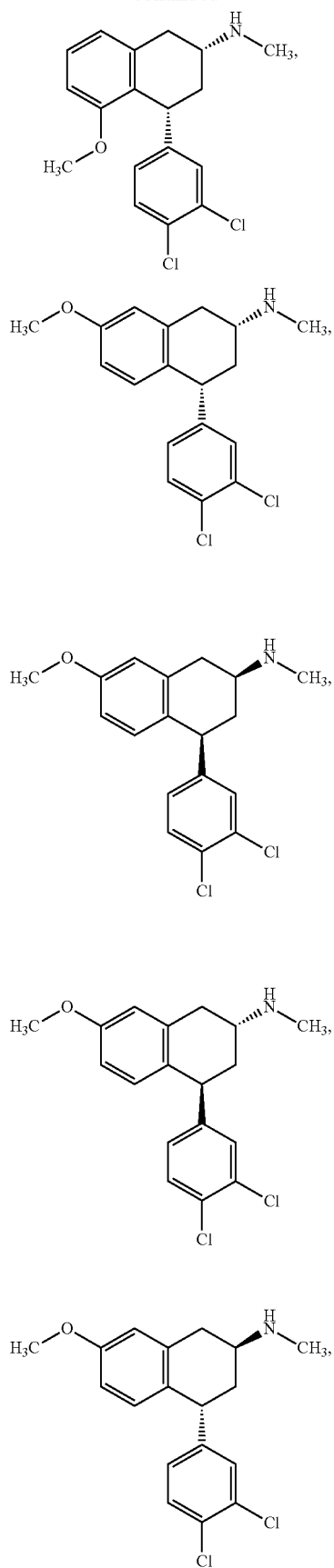
92
-continued
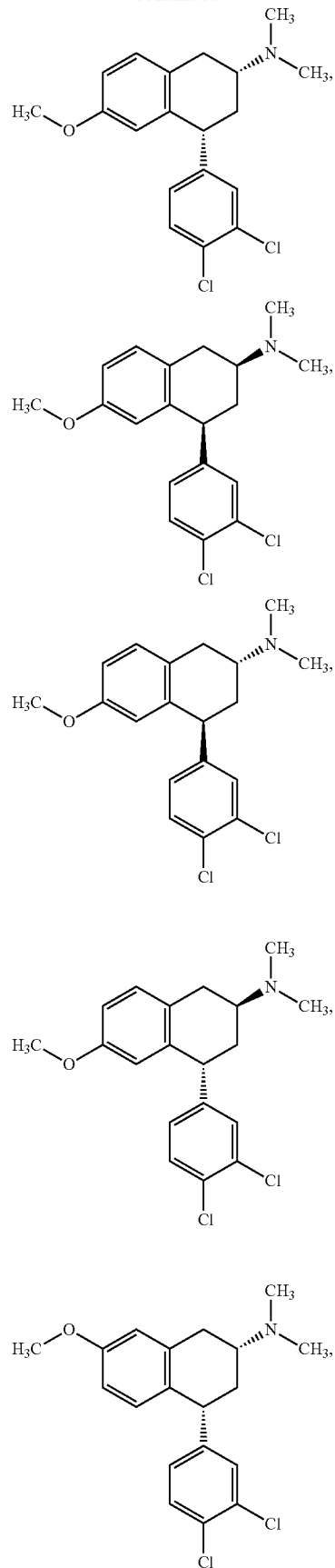

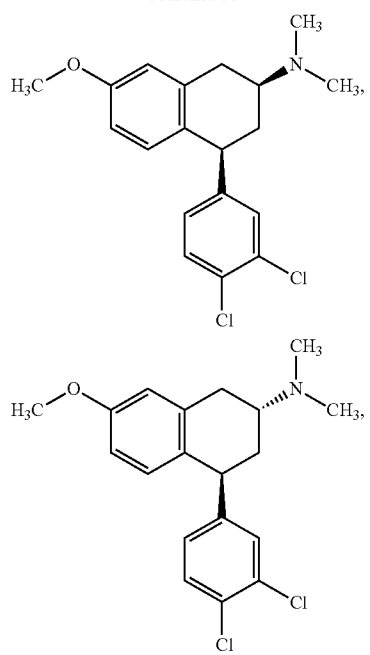
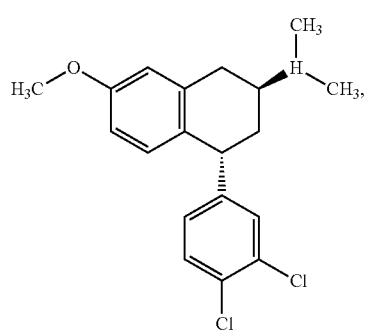
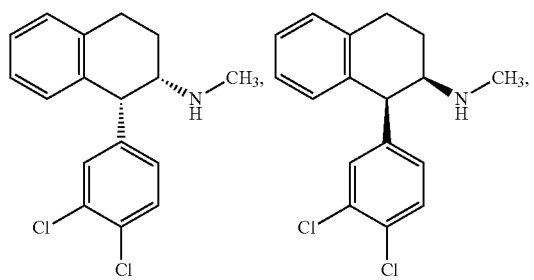
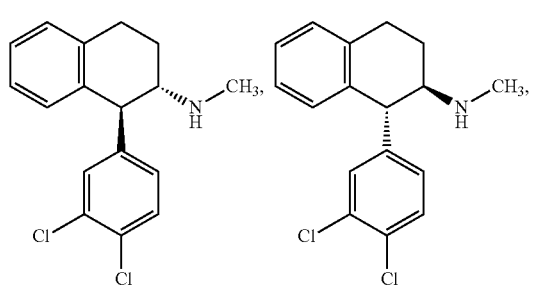
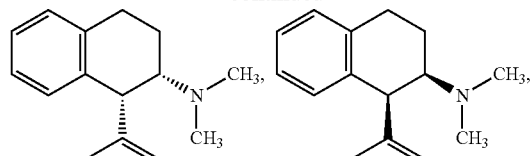
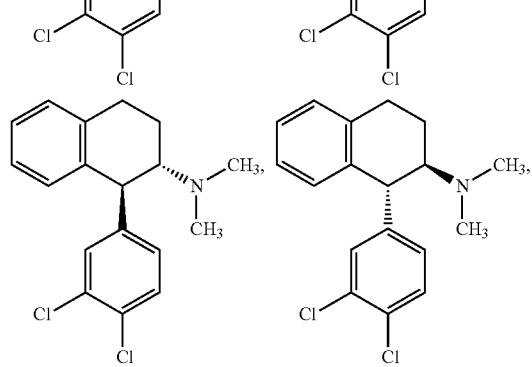
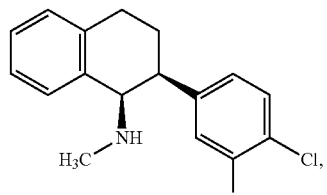
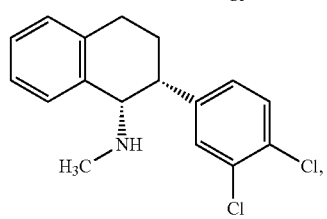
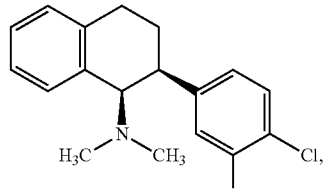
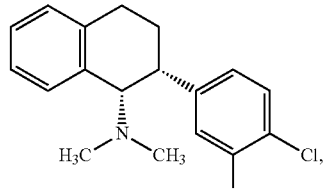
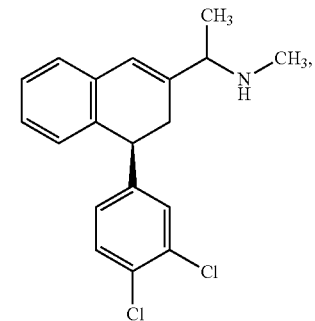

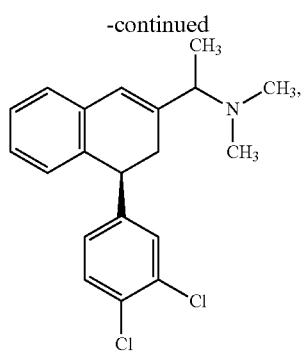
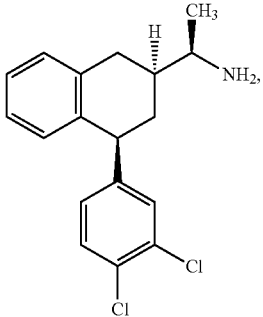
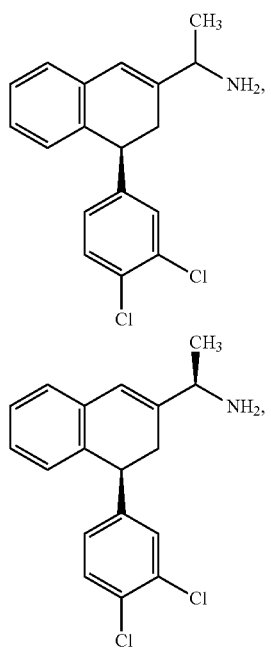
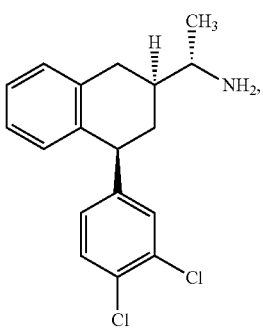
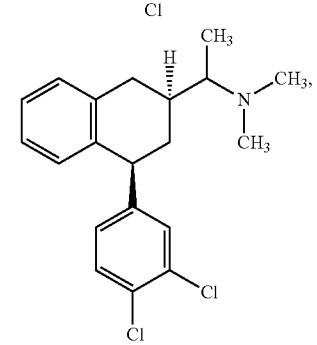
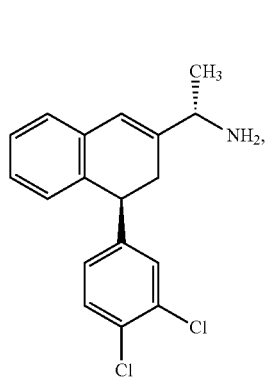
or
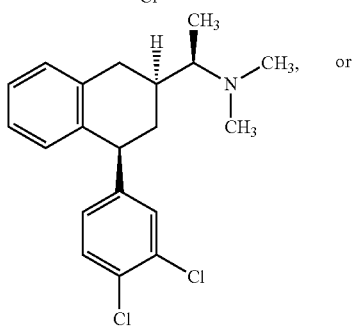
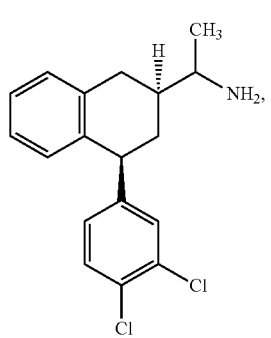
and any enantiomer, diastereoisomer, racemic mixture, enantiomerically enriched mixture, and enantiomerically pure form thereof.

20. A pharmaceutical composition comprising a compound of claim 19, or a pharmaceutically acceptable salt thereof, and a pharmaceutically acceptable carrier, vehicle or diluent.

21. The compound of claim 3, wherein Y and Z are both Cl.

22. The compound of claim 21, wherein m is 1, X is H or $OR^5$, and $R^3$ and $R^4$ are independently H or substituted or unsubstituted $C_1$-$C_4$ alkyl.

23. The compound of claim 22, wherein $R^5$ is H.

* * * * *

UNITED STATES PATENT AND TRADEMARK OFFICE
CERTIFICATE OF CORRECTION

PATENT NO. : 8,053,603 B2  
APPLICATION NO. : 11/643190  
DATED : November 8, 2011  
INVENTOR(S) : Liming Shao et al.

Page 1 of 1

It is certified that error appears in the above-identified patent and that said Letters Patent is hereby corrected as shown below:

Column 1, line 9, under the item [60] entitled Cross Reference to Related Applications, replace the priority application filing date to read:

-- This application claims priority under 35 U.S.C. §119(e) to

U.S. Provisional Patent Application No. 60/756,555, filed Jan. 6, 2006 [...]. --

Signed and Sealed this  
Twenty-first Day of February, 2012

David J. Kappos  
*Director of the United States Patent and Trademark Office*